US012735412B2

(12) United States Patent
Jin et al.

(10) Patent No.: US 12,735,412 B2
(45) Date of Patent: Sep. 15, 2026

(54) SMALL MOLECULE ANTAGONISTS FOR THE RELAXIN-3/RXFP3 SYSTEM

(71) Applicant: RESEARCH TRIANGLE INSTITUTE, Research Triangle Park, NC (US)

(72) Inventors: Chunyang Jin, Apex, NC (US); Elaine Gay, Chapel Hill, NC (US)

(73) Assignee: RESEARCH TRIANGLE INSTITUTE, Durham, NC (US)

( * ) Notice: Subject to any disclaimer, the term of this patent is extended or adjusted under 35 U.S.C. 154(b) by 405 days.

(21) Appl. No.: 18/280,794

(22) PCT Filed: Mar. 7, 2022

(86) PCT No.: PCT/US2022/019115
§ 371 (c)(1),
(2) Date: Sep. 7, 2023

(87) PCT Pub. No.: WO2022/192126
PCT Pub. Date: Sep. 15, 2022

(65) Prior Publication Data

US 2024/0208955 A1 Jun. 27, 2024

Related U.S. Application Data

(60) Provisional application No. 63/158,045, filed on Mar. 8, 2021.

(51) Int. Cl.

| | |
|---|---|
| ***C07D 413/14*** | (2006.01) |
| ***A61K 31/4245*** | (2006.01) |
| ***A61K 31/4439*** | (2006.01) |
| ***A61K 31/444*** | (2006.01) |
| ***C07D 413/12*** | (2006.01) |

(52) U.S. Cl.
CPC ........ *C07D 413/14* (2013.01); *A61K 31/4245* (2013.01); *A61K 31/4439* (2013.01); *A61K 31/444* (2013.01); *C07D 413/12* (2013.01)

(58) Field of Classification Search
CPC .................................................... C07D 413/14
See application file for complete search history.

(56) References Cited

U.S. PATENT DOCUMENTS

| | | | | |
|---|---|---|---|---|
| 6,573,283 | B2 * | 6/2003 | Stack | C07D 491/04 546/273.1 |
| 2005/0032683 | A1 | 2/2005 | Amento et al. | |
| 2006/0247163 | A1 | 11/2006 | Unemori | |
| 2012/0289495 | A1 * | 11/2012 | Baloglu | A61P 25/24 546/276.7 |
| 2014/0038895 | A1 | 2/2014 | Rosengren et al. | |

FOREIGN PATENT DOCUMENTS

| | | | |
|---|---|---|---|
| WO | 2012031328 | A1 | 3/2012 |
| WO | 2020231337 | A1 | 11/2020 |

OTHER PUBLICATIONS

Schiemann et al. CAS: 161: 955036, 2014.*
Baloglu et al. CAS: 155: 182084, 2012.*
Calvez, Juliane, et al. "Role of relaxin-3/RXFP3 system in stress-induced binge-like eating in female rats." Neuropharmacology 102 (2016): 207-215.
EESR issued Dec. 17, 2024 in corresponding EP Application No. 22767725.9.
Guan, Dongliang, et al. "Development of Diphenyl-1, 2, 4-Oxadiazole Analogues as Allosteric Modulators of the RXFP3 Receptor: Evaluation of Importance of the N-Substituted-2-Pyrrolidone Moiety in RLX-33." Journal of Medicinal Chemistry 68.7 (2025): 7751-7766.
Conole, Daniel, et al. "Synthesis and methemoglobinemia-inducing properties of benzocaine isosteres designed as humane rodenticides." Bioorganic & Medicinal Chemistry 22.7 (2014): 2220-2235.
Ganella, D. E., et al. "Modulation of feeding by chronic rAAV expression of a relaxin-3 peptide agonist in rat hypothalamus." Gene therapy 20.7 (2013): 703-716.
Haugaard-Kedstrom, Linda M., et al. "Design, synthesis, and characterization of a single-chain peptide antagonist for the relaxin-3 receptor RXFP3." Journal of the American Chemical Society 133. 13 (2011): 4965-4974.
Kumar, Jigna Rajesh, et al. "Relaxin'the brain: a case for targeting the nucleus incertus network and relaxin-3/RXFP3 system in neuropsychiatric disorders." British journal of pharmacology 174. 10 (2017): 1061-1076.
Liu, Changlu, et al. "Identification of relaxin-3/INSL7 as a ligand for GPCR142." Journal of Biological Chemistry 278.50 (2003): 50765-50770.
Ma, Sherie, et al. "Distribution, physiology and pharmacology of relaxin-3/RXFP3 systems in brain." British Journal of Pharmacology 174.10 (2017): 1034-1048.
Pubmed Compound Record for CID 39835335, '(3S)-1-((4-methylphenyl)methyl)-5-oxo-N-[4-(3-phenyl-1,2,4-oxadiazol-5-yl)phenyl]pyrrolidine-3-carboxamide', U.S. National Library of Medicine, May 29, 2009 (May 29, 2009), pp. 1-7 (https://pubchem.ncbi.nlm.nih.gov/compound/39835335); p. 2.
Ryan, P. J., et al. "Relaxin-3 mRNA levels in nucleus incertus correlate with alcohol and sucrose intake in rats." Drug and alcohol dependence 140 (2014): 8-16.
Ryan, Philip J., et al. "Central relaxin-3 receptor (RXFP3) activation decreases anxiety-and depressive-like behaviours in the rat." Behavioural brain research 244 (2013): 142-151.
Ryan, Philip J., et al. "Relaxin-3/RXFP3 system regulates alcohol-seeking." Proceedings of the National Academy of Sciences 110.51 (2013): 20789-20794.
Smith, Craig M., et al. "Central injection of relaxin-3 receptor (RXFP3) antagonist peptides reduces motivated food seeking and consumption in C57BL/6J mice." Behavioural brain research 268 (2014): 117-126.

(Continued)

*Primary Examiner* — Rei Tsang Shiao
(74) *Attorney, Agent, or Firm* — Barnes & Thornburg LLP

(57) ABSTRACT

Non-peptide, small molecule antagonists of the relaxin family peptide 3 receptor (RXPP3) that can inhibit relaxin-3 activity are described. The compounds can include a pyrrolidone or piperidone substituted with an aryl amide. Also described are methods of preparing the antagonists and methods of using the antagonists to treat diseases, disorders and conditions, such as obesity, alcoholism and other substance abuse and/or addiction-related conditions.

16 Claims, 2 Drawing Sheets

(56) References Cited

OTHER PUBLICATIONS

Van Der Westhuizen, Emma T., et al. "The relaxin family peptide receptor 3 activates extracellular signal-regulated kinase ½ through a protein kinase C-dependent mechanism." Molecular pharmacology 71.6 (2007): 1618-1629.
Walker, Andrew W., et al. "Relaxin-3 receptor (RXFP3) signalling mediates stress-related alcohol preference in mice." PLoS One 10.4 (2015): e0122504.
Zorrilla, Eric P., Marian L. Logrip, and George F. Koob. "Corticotropin releasing factor: a key role in the neurobiology of addiction." Frontiers in neuroendocrinology 35.2 (2014): 234-244.
International Search Report dated May 23, 2022, prepared in International Application No. PCT/US2022/019115.
International Preliminary Report on Patentability dated Sep. 12, 2023, prepared in International Application No. PCT/US2022/019115.
Gay, Elaine A., et al. "Discovery and characterization of the first nonpeptide antagonists for the relaxin-3/RXFP3 system." Journal of Medicinal Chemistry 65.11 (2022): 7959-7974.
Van Voorhies, Kalynn J., et al. "Novel RXFP3 negative allosteric modulator RLX-33 reduces alcohol self-administration in rats." Journal of Neurochemistry 167.2 (2023): 204-217.

* cited by examiner

SMALL MOLECULE ANTAGONISTS FOR THE RELAXIN-3/RXFP3 SYSTEM

RELATED APPLICATIONS

This application is a National Stage application of International Application No. PCT/US2022/019115, filed Mar. 7, 2022, which claims the benefit of U.S. Provisional Patent Application No. 63/158,045 filed Mar. 8, 2021.

TECHNICAL FIELD

The presently disclosed subject matter relates to small molecule antagonists for the relaxin-3/RXFP3 system. The presently disclosed subject matter further relates to the preparation of the small molecule antagonists and to methods of treating diseases, such as alcoholism, obesity, and drug addiction using the antagonists.

BACKGROUND

Alcoholism remains a significant clinical problem and extracts great emotional, social, and economic costs. In the United States, alcohol is the third leading preventable cause of death. According to the Centers for Disease Control, the cost of alcoholism reached 249 billion dollars in 2010. Current pharmacotherapies for alcoholism, such as naltrexone and acamprosate, are inadequate due to medication compliance issues, low efficacy, and serious side effects. Therefore, there is a need for additional therapeutic agents for treating alcoholism, such as for agents based on additional biological targets and/or that can prevent relapse.

Relaxin-3 and its cognate G protein-coupled receptor (GPCR), relaxin family peptide receptor 3 (RXFP3), are a newly identified neuropeptide system implicated in a range of physiological functions, including response to stress, feeding, motivation for reward, and circadian rhythm. See Ma et al., Br. J. Pharmacol. 2017, 174, 1034; and Kumar et al., Br. J. Pharmacol. 2017, 174, 1061. Thus, compounds that can modulate relaxin-3/RXFP3 activity have potential in treating a number of diseases and conditions, such as anxiety, obesity, and drug addiction. Studies using RXFP3-specific peptide antagonists and genetically modified animal models support the use of RXFP3 antagonists as a therapeutic tool to treat alcoholism and related disorders. However, peptide antagonists are metabolically unstable and do not cross the bood-brain barrier. Thus, they must be administered via central injection, limiting their research and therapeutic potential.

Accordingly, there is an ongoing need for additional compounds that can modulate relaxin-3/RXFP3, particularly non-peptide and/or small molecule RXFP3 antagonists.

SUMMARY

In some embodiments, the presently disclosed subject matter provides a compound having inhibitory activity for the relaxin family peptide 3 receptor (RXFP3), wherein said compound is a non-peptidyl small molecule compound, optionally wherein the compound has a half maximal inhibitory concentration $IC_{50}$ for RXFP3 in the presence of relaxin-3 of about 10 micromolar (μM) or less, further optionally wherein said compound is an aryl amide-substituted. N-substituted gamma (γ) or delta (δ) lactam. In some embodiments, the compound has a structure of Formula (I):

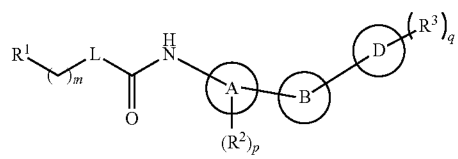

wherein: L is

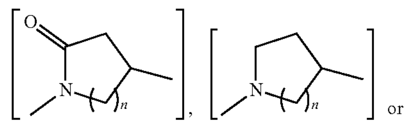

or

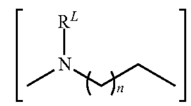

;

n is an integer between 1 and 3; $R^L$ is selected from the group comprising hydrogen, C1-C6 substituted or unsubstituted alkyl, C2-C6 substituted or unsubstituted alkenyl, C3-C6 substituted or unsubstituted cycloalkyl, substituted or unsubstituted heterocyclo, substituted or unsubstituted aryl, and substituted or unsubstituted heteroaryl; m is an integer between 0 and 3; p is an integer between 0 and 3; q is an integer between 0 and 3; A is selected from phenyl and pyridinyl; B is a five-membered heterocyclic group; D is present or absent, and when present is selected from substituted or unsubstituted aryl and substituted or unsubstituted heteroaryl; $R^1$ is selected from the group comprising hydrogen, C1-C6 substituted or unsubstituted alkyl, C2-C6 substituted or unsubstituted alkenyl, C3-C6 substituted or unsubstituted cycloalkyl, substituted or unsubstituted heterocyclo, substituted or unsubstituted aryl, and substituted or unsubstituted heteroaryl; each $R^2$ is independently selected from the group comprising substituted or unsubstituted C1-C6 alkyl, substituted or unsubstituted C3-C6 alkenyl, C1-C6 substituted or unsubstituted cycloalkyl, C1-C6 alkoxy; substituted or unsubstituted heterocyclo, halo, nitro, cyano, amino, alkylsulfonyl, ester and amide; and each $R^3$ is independently selected from C1-C6 substituted or unsubstituted alkyl, C2-C6 substituted or unsubstituted alkenyl, C3-C6 substituted or unsubstituted cycloalkyl, C1-C6 alkoxy, substituted or unsubstituted heterocyclo, halo, nitro, cyano, amino, alkylsulfonyl, ester, and amide; or a pharmaceutically acceptable salt thereof. In some embodiments, B is 1,2,4-oxadiazole.

In some embodiments, m is 1, 2, or 3; and $R^1$ is selected from a substituted or unsubstituted phenyl, a substituted or unsubstituted five-membered heteroaryl, and a substituted or unsubstituted six-membered heteroaryl. In some embodiments, $R^1$ is phenyl, a five-membered heteroaryl, or a six-membered heteroaryl, and wherein said phenyl, five-membered heteroaryl, or six-membered heteroaryl is substituted with one or more of the group comprising C1-C6 alkyl, C2-C6 alkenyl, C1-C6 alkoxy, C3-C6 cycloalkyl, heterocyclo, halo, nitro, cyano, amino, alkylsulfonyl, ester, and amide.

In some embodiments, L is

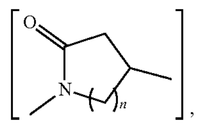

n is 2. In some embodiments, the compound is:

RLX-34

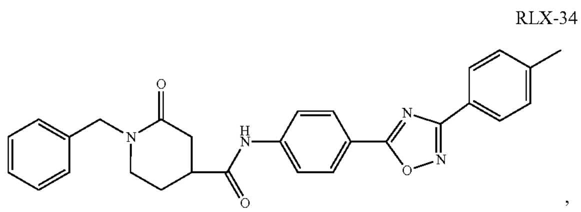 [SMILES: Cc1ccc(-c2noc(-c3ccc(NC(=O)C4CCN(Cc5ccccc5)C(=O)C4)cc3)n2)cc1]

or a pharmaceutically acceptable salt thereof.

In some embodiments, n is 1. In some embodiments, the compound is:

RLX-36

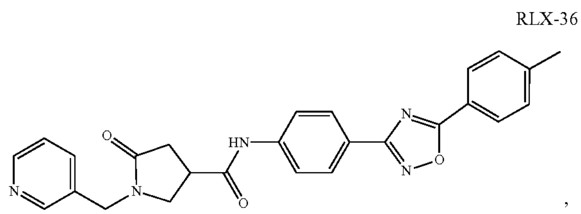 [SMILES: Cc1ccc(-c2nc(-c3ccc(NC(=O)C4CC(=O)N(Cc5cccnc5)C4)cc3)no2)cc1]

or a pharmaceutically acceptable salt thereof.

In some embodiments, the compound has a structure of Formula (II):

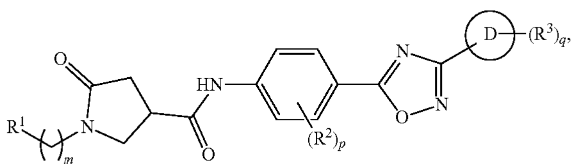

wherein: m is an integer between 0 and 3; p is an integer between 0 and 3; q is an integer between 0 and 3; D is present or absent, and when present is selected from substituted or unsubstituted aryl and substituted or unsubstituted heteroaryl; $R^1$ is selected from the group comprising hydrogen. C1-C6 substituted or unsubstituted alkyl, C2-C6 substituted or unsubstituted alkenyl. C3-C6 substituted or unsubstituted cycloalkyl, substituted or unsubstituted heterocyclo, substituted or unsubstituted aryl, and substituted or unsubstituted heteroaryl; each $R^2$ is independently selected from the group comprising substituted or unsubstituted C1-C6 alkyl, substituted or unsubstituted C3-C6 alkenyl, C3-C6 substituted or unsubstituted cycloalkyl. C1-C6 alkoxy; substituted or unsubstituted heterocyclo, halo, nitro, cyano, amino, alkylsulfonyl, ester and amide; and each $R^3$ is independently selected from C1-C6 substituted or unsubstituted alkyl, C2-C6 substituted or unsubstituted alkenyl, C3-C6 substituted or unsubstituted cycloalkyl, C1-C6 alkoxy, substituted or unsubstituted heterocyclo, halo, nitro, cyano, amino, alkylsulfonyl, ester, and amide; or a pharmaceutically acceptable salt thereof.

In some embodiments. D is absent and $R^3$ is C1-C6 unsubstituted alkyl or C1-C6 substituted alkyl, optionally wherein when $R^3$ is C1-C6 substituted alkyl, the C1-C6 alkyl is substituted by phenyl or substituted phenyl. In some embodiments, m is 1, $R^1$ is pyridinyl, and the compound is selected from:

RLX-31

RLX-35

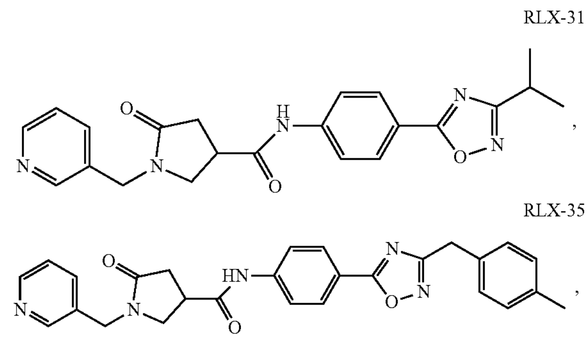

and pharmaceutically acceptable salts thereof.

In some embodiments, D is present and selected from the group comprising phenyl and pyridinyl. In some embodiments, $R^1$ is selected from the group comprising methyl, phenyl, substituted phenyl, pyridinyl, thiophenyl, and furanyl.

In some embodiments, $R^1$ is pyridinyl and D is pyridinyl, optionally wherein q is 0. In some embodiments, the compound is selected from:

RLX-28

RLX-29

RLX-30

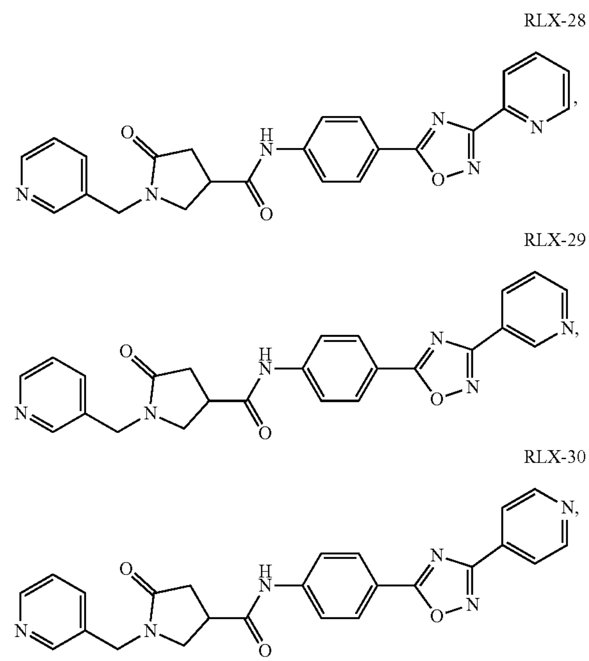

and pharmaceutically acceptable salts thereof.

In some embodiments, D is phenyl. In some embodiments, q is 0 or 1, and wherein $R^3$ is selected from C1-C6 substituted or unsubstituted alkyl, balo, C1-C6 alkoxy, and amino, optionally wherein $R^3$ is selected from methyl, ethyl, isopropyl, fluoro, chloro, bromo, trifluoromethyl, methoxy, and dimethylamino.

In some embodiments, $R^1$ is phenyl or substituted phenyl. In some embodiments, the compound is selected from the group comprising:

RLX-1

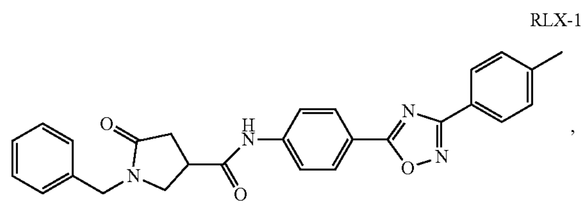

,

RLX-2

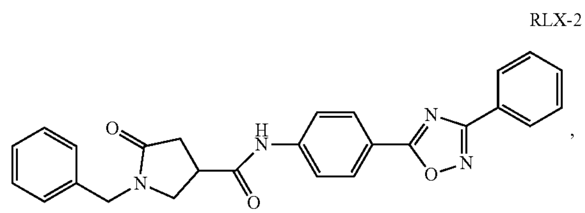

,

RLX-3

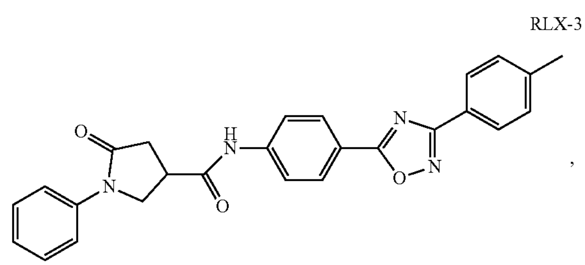

,

RLX-4

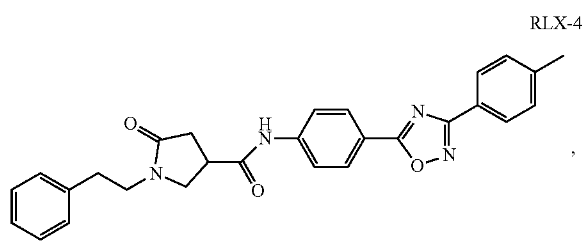

,

RLX-5

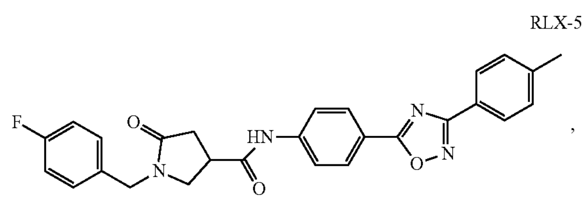

,

RLX-6

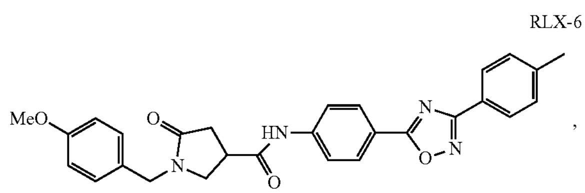

,

RLX-7

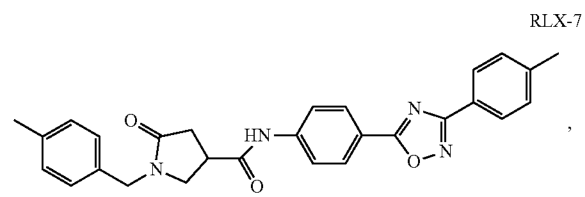

,

-continued

RLX-8

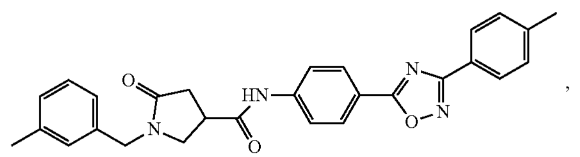

, and pharmaceutically acceptable salts thereof.

In some embodiments, $R^1$ is C1-C6 alkyl. In some embodiments, the compound is:

RLX-15

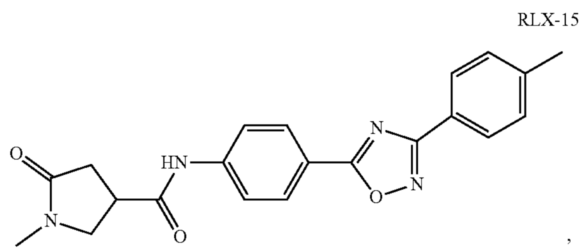

, or a pharmaceutically acceptable salt thereof.

In some embodiments, m is 1 and $R^1$ is heteroaryl. In some embodiments, $R^1$ is selected from pyridinyl, thiophenyl, and furanyl. In some embodiments, $R^1$ is furan-2-yl, thiophen-2-yl, or thiophen-3-yl, q is 1, and $R^3$ is C1-C6 alkyl, optionally methyl. In some embodiments, the compound is selected from the group comprising:

RLX-12

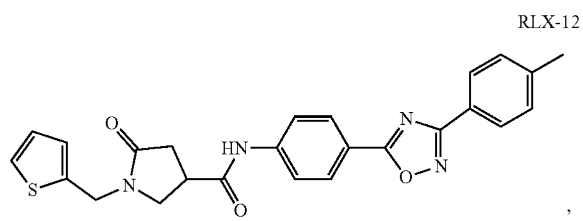

,

RLX-13

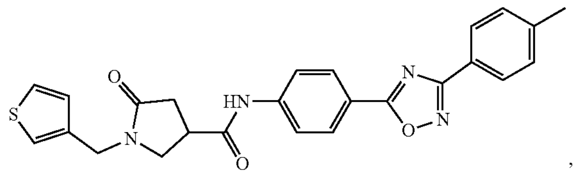

,

RLX-14

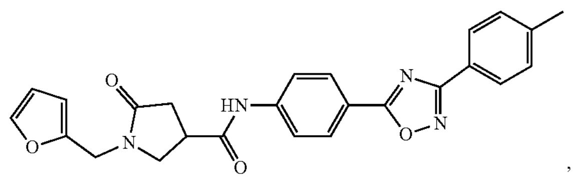

, and pharmaceutically acceptable salts thereof.

In some embodiments, $R^1$ is furan-2-yl, q is 1, and $R^3$ is halo or substituted C1-C6 alkyl. In some embodiments, the compound is selected from:

RLX-32

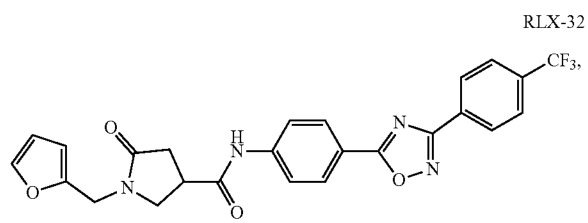

RLX-33

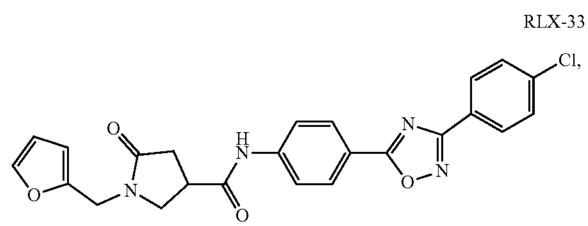

and pharmaceutically acceptable salts thereof.

In some embodiments, $R^1$ is pyridinyl, optionally 3-pyridinyl. In some embodiments, q is 1 and $R^3$ is selected from C1-C6 substituted alkyl or halo, optionally wherein $R^1$ is selected from $CF_3$, chloro, or bromo. In some embodiments, the compound is selected from the group comprising:

RLX-9

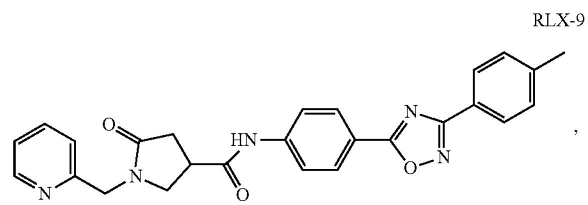

RLX-10

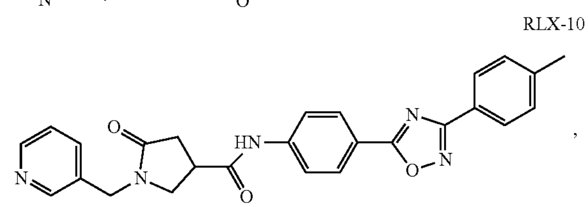

RLX-11

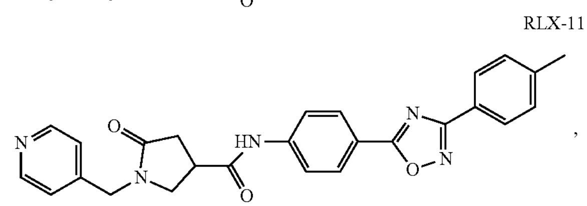

RLX-16

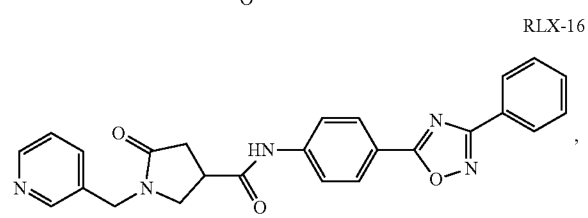

RLX-17

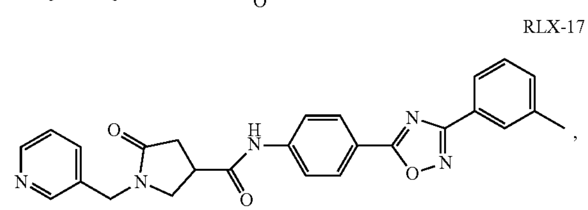

-continued

RLX-18

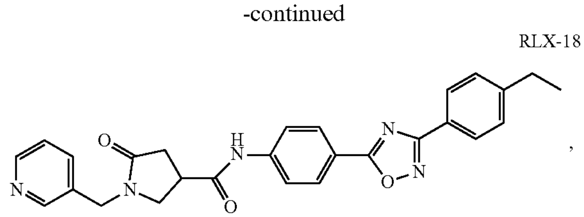

RLX-19

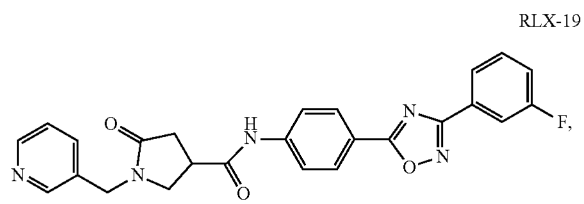

RLX-20

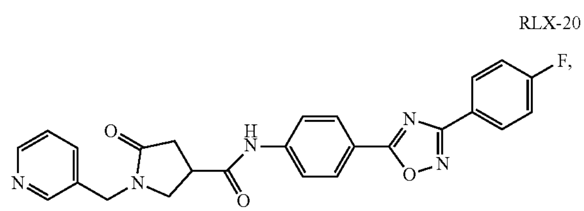

RLX-21

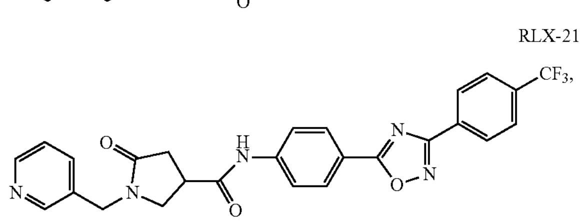

RLX-22

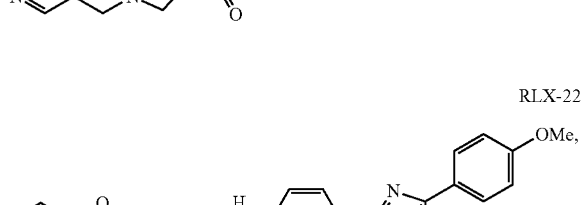

RLX-23

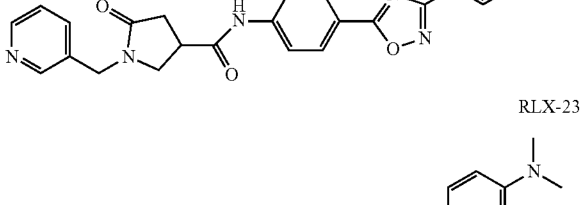

RLX-24

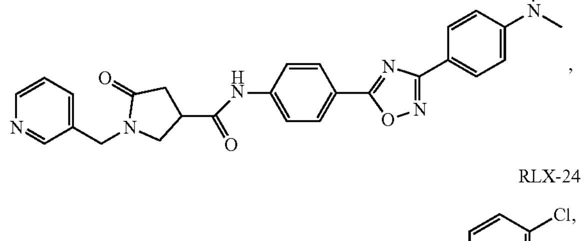

RLX-25

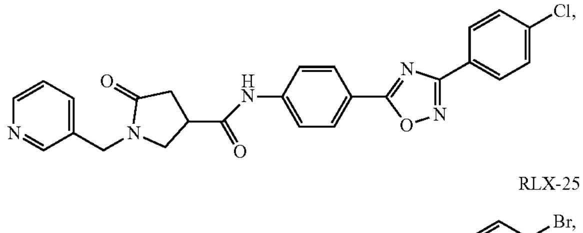

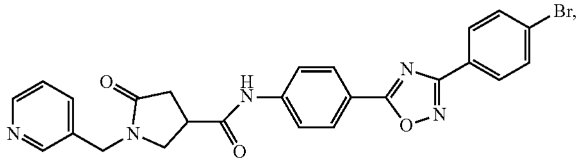

-continued

RLX-26

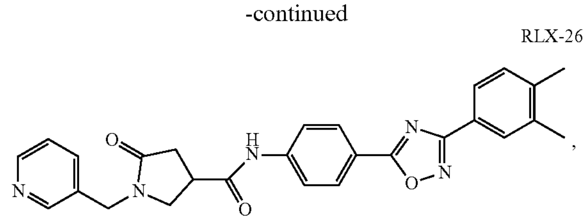

RLX-27

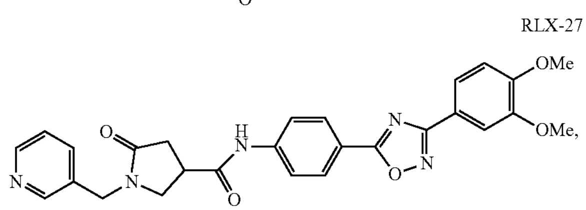

and pharmaceutically acceptable salts thereof.

In some embodiments, the compound has a structure of Formula (III):

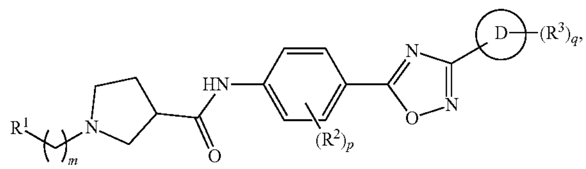

wherein: m is an integer between 0 and 3; p is an integer between 0 and 3; q is an integer between 0 and 3; D is present or absent, and when present is selected from substituted or unsubstituted aryl and substituted or unsubstituted heteroaryl; $R^1$ is selected from the group comprising hydrogen, C1-C6 substituted or unsubstituted alkyl, C2-C6 substituted or unsubstituted alkenyl, C3-C6 substituted or unsubstituted cycloalkyl, substituted or unsubstituted heterocyclo, substituted or unsubstituted aryl, and substituted or unsubstituted heteroaryl; each $R^2$ is independently selected from the group comprising substituted or unsubstituted C1-C6 alkyl, substituted or unsubstituted C3-C6 alkenyl, C3-C6 substituted or unsubstituted cycloalkyl, C1-C6 alkoxy; substituted or unsubstituted heterocyclo, halo, nitro, cyano, amino, alkylsulfonyl, ester and amide; and each $R^3$ is independently selected from C1-C6 substituted or unsubstituted alkyl, C2-C6 substituted or unsubstituted alkenyl, C3-C6 substituted or unsubstituted cycloalkyl, C1-C6 alkoxy, substituted or unsubstituted heterocyclo, halo, nitro, cyano, amino, alkylsulfonyl, ester, and amide; or a pharmaceutically acceptable salt thereof.

In some embodiments, $R^1$ is phenyl and D is phenyl. In some embodiments, the compound is:

RLX-37

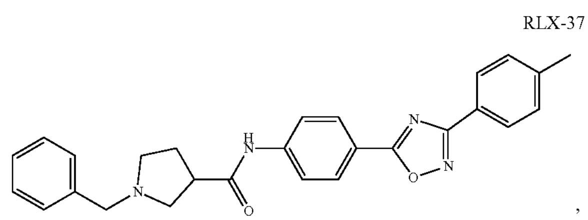 [SMILES: Cc1ccc(-c2noc(-c3ccc(NC(=O)C4CCN(Cc5ccccc5)C4)cc3)n2)cc1]

and pharmaceutically acceptable salts thereof.

In some embodiments, the compound has a structure of Formula (IV):

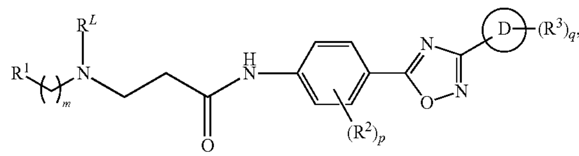

wherein: m is an integer between 0 and 3; p is an integer between 0 and 3; q is an integer between 0 and 3; D is present or absent, and when present is selected from substituted or unsubstituted aryl and substituted or unsubstituted heteroaryl; $R^1$ is selected from the group comprising hydrogen. C1-C6 substituted or unsubstituted alkyl, C2-C6 substituted or unsubstituted alkenyl, C3-C6 substituted or unsubstituted cycloalkyl, substituted or unsubstituted heterocyclo, substituted or unsubstituted aryl, and substituted or unsubstituted heteroaryl; $R^L$ is selected from the group comprising hydrogen, C1-C6 substituted or unsubstituted alkyl. C2-C6 substituted or unsubstituted alkenyl, C3-C6 substituted or unsubstituted cycloalkyl, substituted or unsubstituted heterocyclo, substituted or unsubstituted aryl, and substituted or unsubstituted heteroaryl; each $R^2$ is independently selected from the group comprising substituted or unsubstituted C1-C6 alkyl, substituted or unsubstituted C3-C6 alkenyl, C3-C6 substituted or unsubstituted cycloalkyl. C1-C6 alkoxy; substituted or unsubstituted heterocyclo, halo, nitro, cyano, amino, alkylsulfonyl, ester and amide; and each $R^3$ is independently selected from C1-C6 substituted or unsubstituted alkyl, C2-C6 substituted or unsubstituted alkenyl, C3-C6 substituted or unsubstituted cycloalkyl. C1-C6 alkoxy, substituted or unsubstituted heterocyclo, halo, nitro, cyano, amino, alkylsulfonyl, ester, and amide; or a pharmaceutically acceptable salt thereof.

In some embodiments, $R^1$ is phenyl and D is phenyl. In some embodiments, $R^L$ is methyl or hydrogen, and the compound is selected from:

RLX-38

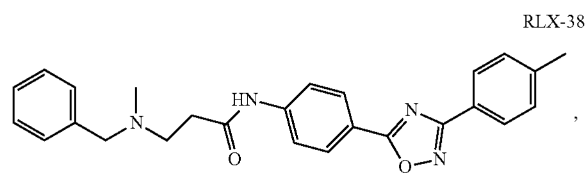

RLX-39

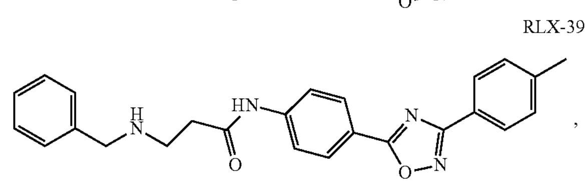

and pharmaceutically acceptable salts thereof.

In some embodiments, the compound selectively inhibits RXFP3 compared to relaxin family peptide receptor 1 (RXFP1) and/or relaxin family peptide receptor 4 (RXFP4). In some embodiments, the compound has a half maximal inhibitory concentration $IC_{50}$ for RXFP3 that is at least about 10 times lower than its $IC_{50}$ for RXFP1, optionally wherein the compound has an $IC_{50}$ for RXFP3 that is at least about 100 times lower than its $IC_{50}$ for RXFP1.

In some embodiments, the presently disclosed subject matter provides a pharmaceutical composition comprising a non-peptidyl small molecule compound having inhibitory activity for RXFP3 and a pharmaceutically acceptable carrier.

In some embodiments, the presently disclosed subject matter provides a method of treating a disease or condition wherein inhibition of biological activity at or signalling via the RXFP3 receptor is desirable in a subject in need thereof, the method comprising administering to said subject an effective amount of a non-peptidyl small molecule compound having inhibitory activity for RXFP3 or of a pharmaceutical composition thereof. In some embodiments, the disease or condition is selected from obesity, antipsychotic drug-induced weight gain, hyperphagia associated with depression, alcoholism, and other substance abuse and/or addiction-related disorders. In some embodiments, the subject is a human.

In some embodiments, the presently disclosed subject matter provides a method for the prevention or inhibition of substance abuse and/or addiction, addictive behavior, or of a symptom, behavior, or condition associated with substance abuse and/or addiction, the method comprising administering to a subject in need thereof an effective amount of a non-peptidyl small molecule compound having inhibitory activity for RXFP3 or of a pharmaceutical composition thereof. In some embodiments, the behavior associated with substance abuse and/or addiction comprises substance use (self-administration) and/or substance seeking behavior. In some embodiments, the substance abuse and/or addiction comprises alcohol abuse and/or addiction. In some embodiments, the subject is a human.

It is an object of the presently disclosed subject matter to provide non-peptidyl small molecule antagonists of RXFP3, as well as pharmaceutical compositions comprising the antagonists and methods of treating diseases, such as alcoholism, using the antagonists.

Certain objects of the presently disclosed subject matter having been stated hereinabove, which are addressed in whole or in part by the presently disclosed subject matter, other objects and aspects will become evident as the description proceeds when taken in connection with the accompanying Examples as best described herein below.

BRIEF DESCRIPTION OF THE DRAWINGS

The presently disclosed subject matter can be better understood by referring to the following figures. The components in the figures are not necessarily to scale, emphasis instead being placed upon illustrating the principles of the presently disclosed subject matter. A further understanding of the presently disclosed subject matter can be obtained by reference to an embodiment set forth in the illustrations of the accompanying drawings. Although the illustrated embodiment is merely exemplary of systems for carrying out the presently disclosed subject matter, both the organization and method of operation of the presently disclosed subject matter, in general, together with further objectives and advantages thereof, may be more easily understood by reference to the drawings and the following description. The drawings are not intended to limit the scope of this presently disclosed subject matter, which is set forth with particularity in the claims as appended or as subsequently amended, but merely to clarify and exemplify the presently disclosed subject matter.

For a more complete understanding of the presently disclosed subject matter, reference is now made to the following drawings in which.

DETAILED DESCRIPTION

Figure 1:
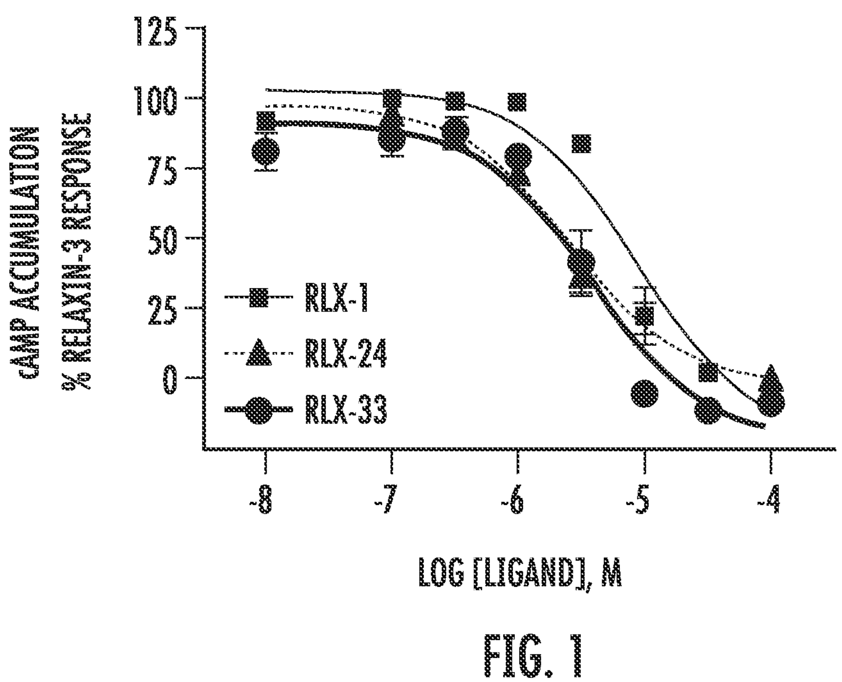
FIG. 1 displays the concentration-response curves of representative compounds (RLX-1, RLX-24, and RLX-33) for inhibition of relaxin-3 activity in RXFP3 cAMP accumulation assays.

The presently disclosed subject matter will now be described more fully hereinafter with reference to the accompanying Examples, in which representative embodiments are shown. The presently disclosed subject matter can, however, be embodied in different forms and should not be construed as limited to the embodiments set forth herein. Rather, these embodiments are provided so that this disclosure will be thorough and complete, and will fully convey the scope of the embodiments to those skilled in the art.

Unless otherwise defined, all technical and scientific terms used herein have the same meaning as commonly understood by one of ordinary skill in the art to which this presently described subject matter belongs. All publications, patent applications, patents, and other references mentioned herein are incorporated by reference in their entirety.

Throughout the specification and claims, a given chemical formula or name shall encompass all optical and stereoisomers, as well as racemic mixtures where such isomers and mixtures exist, unless as otherwise specifically indicated.

I. Definitions

Following long-standing patent law convention, the terms "a", "an", and "the" refer to "one or more" when used in this application, including the claims. Thus, for example, reference to "a solvent" includes mixtures of one or more solvents, two or more solvents, and the like.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in the present specification and attached claims are approximations that can vary depending upon the desired properties sought to be obtained by the presently disclosed subject matter.

The term "about", as used herein when referring to a measurable value such as an amount of weight, molar equivalents, time, temperature, etc. is meant to encompass in one example variations of ±20% or ±10%, in another example ±5%, in another example ±1%, and in yet another example ±0.1% from the specified amount, as such variations are appropriate to perform the disclosed methods.

The term "and/or" when used to describe two or more activities, conditions, or outcomes refers to situations wherein both of the listed conditions are included or wherein only one of the two listed conditions are included.

The term "comprising", which is synonymous with "including," "containing," or "characterized by" is inclusive or open-ended and does not exclude additional, unrecited elements or method steps. “Comprising” is a term of art used in claim language, which means that the named elements are essential, but other elements can be added and still form a construct within the scope of the claim.

As used herein, the phrase “consisting of” excludes any element, step, or ingredient not specified in the claim. When the phrase “consists of” appears in a clause of the body of a claim, rather than immediately following the preamble, it limits only the element set forth in that clause; other elements are not excluded from the claim as a whole.

As used herein, the phrase “consisting essentially of” limits the scope of a claim to the specified materials or steps, plus those that do not materially affect the basic and novel characteristic(s) of the claimed subject matter.

With respect to the terms “comprising”, “consisting of”, and “consisting essentially of”, where one of these three terms is used herein, the presently disclosed and claimed subject matter can include the use of either of the other two terms.

As used herein the term “alkyl” refers to $C_{1-20}$ inclusive, linear (i.e., “straight-chain”), branched, or cyclic, saturated, or at least partially and in some cases fully unsaturated (i.e., alkenyl and alkynyl) hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. “Branched” refers to an alkyl group in which a lower alkyl group, such as methyl, ethyl, or propyl, is attached to a linear alkyl chain. “Lower alkyl” refers to an alkyl group having 1 to about 8 carbon atoms (i.e., a $C_{1-8}$ alkyl), e.g., 1, 2, 3, 4, 5, 6, 7, or 8 carbon atoms. In some embodiments, “lower alkyl” can refer to $C_{1-6}$ or $C_{1-5}$ alkyl groups, “Higher alkyl” refers to an alkyl group having about 10 to about 20 carbon atoms, e.g., 10, 11, 12, 13, 14, 15, 16, 17, 18, 19, or 20 carbon atoms. In certain embodiments, “alkyl” refers, in particular, to $C_{1-8}$ straight-chain alkyls. In other embodiments, “alkyl” refers, in particular, to $C_{1-8}$ branched-chain alkyls.

Alkyl groups can optionally be substituted (a “substituted alkyl”) with one or more alkyl group substituents, which can be the same or different. The term “alkyl group substituent” includes but is not limited to alkyl, substituted alkyl, halo, nitro, cyano, amino, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as “alkylaminoalkyl”), or aryl.

Thus, as used herein, the term “substituted alkyl” includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, cyano, amino, alkylamino, dialkylamino, ester, acyl, amide, sulfonyl, sulfate, and mercapto.

The term “alkenyl” refers to an alkyl group as defined above including at least one carbon-carbon double bond. Exemplary alkenyl groups include, but are not limited to, ethenyl, propenyl, butenyl, pentenyl, hexenyl, octenyl, butadienyl, and allenyl groups. Alkenyl groups can optionally be substituted with one or more alkyl group substituents, which can be the same or different, including, but not limited to alkyl (saturated or unsaturated), substituted alkyl (e.g., halo-substituted and perhalo-substituted alkyl, such as but not limited to, $—CF_3$), cycloalkyl, halo, nitro, hydroxyl, carbonyl, carboxyl, acyl, alkoxyl, aryloxyl, aralkoxyl, thioalkyl, thioaryl, thioaralkyl, amino (e.g., aminoalkyl, aminodialkyl, aminoaryl, etc.), sulfonyl, and sulfinyl.

“Cyclic” and “cycloalkyl” refer to a non-aromatic mono- or multicyclic ring system of about 3 to about 10 carbon atoms, e.g., 3, 4, 5, 6, 7, 8, 9, or 10 carbon atoms. In some embodiments, the cycloalkyl ring system comprises between 3 and 6 carbon atoms. The cycloalkyl group can be optionally partially unsaturated. The cycloalkyl group also can be optionally substituted with an alkyl group substituent as defined herein. There can be optionally inserted along the cyclic alkyl chain one or more oxygen, sulfur or substituted or unsubstituted nitrogen atoms, wherein the nitrogen substituent is hydrogen, alkyl, substituted alkyl, aryl, or substituted aryl, thus providing a heterocyclic group. Representative monocyclic cycloalkyl rings include, but are not limited to, cyclopropyl, cyclobutyl, cyclopentyl, cyclohexyl, cycloheptyl, and the like. Further, the cycloalkyl group can be optionally substituted with a linking group, such as an alkylene group as defined hereinabove, for example, methylene, ethylene, propylene, and the like. In such cases, the cycloalkyl group can be referred to as, for example, cyclopropylmethyl, cyclobutylmethyl, and the like. Additionally, multicyclic cycloalkyl rings include adamantyl, octahydronaphthyl, decalin, camphor, camphane, and noradamantyl.

The term “aryl” is used herein to refer to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. The term “aryl” specifically encompasses heterocyclic aromatic compounds (i.e., “heteroaryl”). The aromatic ring(s) can comprise phenyl, naphthyl, biphenyl, diphenylether, diphenylamine and benzophenone, among others. In particular embodiments, the term “aryl” means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings.

The aryl group can be optionally substituted (a “substituted aryl”) with one or more aryl group substituents, which can be the same or different, wherein “aryl group substituent” includes alkyl, substituted alkyl, aryl, substituted aryl, aralkyl, hydroxyl, alkoxyl, aryloxyl, aralkyloxyl, carboxyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —NR'R", wherein R' and R" can each be independently hydrogen, alkyl, substituted alkyl, aryl, substituted aryl, and aralkyl.

Thus, as used herein, the term “substituted aryl” includes aryl groups, as defined herein, in which one or more atoms or functional groups of the aryl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

Specific examples of aryl groups include, but are not limited to, cyclopentadienyl, phenyl, furan, thiophene, pyrrole, pyridine, imidazole, benzimidazole, isothiazole, isoxazole, pyrazole, pyrazine, triazine, pyrimidine, quinoline, isoquinoline, indole, carbazole, napthyl, and the like.

“Heterocyclic”, “heterocycle”, or “heterocyclo” as used herein alone or as part of another group, refers to an aliphatic (e.g., fully or partially saturated heterocyclo) or aromatic (e.g., heteroaryl) monocyclic- or a bicyclic-ring system comprising one or more heteroatoms (e.g., 1, 2, or 3 heteroatoms selected from oxygen, sulfur, and substituted or unsubstituted nitroten) inserted along the cyclic alkyl or aryl carbon chain. Monocyclic ring systems are exemplified by any 5- or 6-membered ring containing 1, 2, 3, or 4 heteroatoms independently selected from oxygen, nitrogen, and sulfur. The 5 membered ring has from 0-2 double bonds and the 6 membered ring has from 0-3 double bonds. Representative examples of monocyclic ring systems include, but are not limited to, ethylene oxide, azetidine, azepine, aziridine, diazepine, 1,3-dioxolane, dioxane, dithiane, furan, imidazole, imidazoline, imidazolidine, isothiazole, isothiazoline, isothiazolidine, isoxazole, isoxazoline, isoxazolidine, morpholine, oxadiazole, oxadiazoline, oxadiazolidine, oxazole, oxazoline, oxazolidine, piperazine, piperidine, pyran, pyrazine, pyrazole, pyrazoline, pyrazolidine, pyridine, pyrimidine, pyridazine, pyrrole, pyrroline, pyrrolidine, tetrahydrofuran, tetrahydropyran, tetrahydrothiophene (also known as thiolane), tetrazine, tetrazole, thiadiazole, thiadiazoline, thiadiazolidine, thiazole, thiazoline, thiazolidine, thiophene, thiomorpholine, thiomorpholine sulfone, thiopyran, triazine, triazole, trithiane, and the like. Bicyclic ring systems are exemplified by any of the above monocyclic ring systems fused to an aryl group as defined herein, a cycloalkyl group as defined herein, or another monocyclic ring system as defined herein. Representative examples of bicyclic ring systems include but are not limited to, for example, benzimidazole, benzothiazole, benzothiadiazole, benzothiophene, benzoxadiazole, benzoxazole, benzofuran, benzopyran, benzothiopyran, benzodioxine, 1,3-benzodioxole, carbazole, cinnoline, indazole, indole, indoline, indolizine, naphthyridine, isobenzofuran, isobenzothiophene, isoindole, isoindoline, isoquinoline, phthalazine, purine, pyranopyridine, quinoline, quinolizine, quinoxaline, quinazoline, tetrahydroisoquinoline, tetrahydroquinoline, thiopyranopyridine, and the like. These rings include quaternized derivatives thereof and may be optionally substituted with one or more alkyl and/or aryl group substituents.

The term "aralkyl" refers to an -alkyl-aryl group, optionally wherein the alkyl and/or aryl group comprises one or more alkyl and/or aryl group substituents.

"Alkylene" can refer to a straight or branched bivalent aliphatic hydrocarbon group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched, or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene ($—CH_2—$); ethylene ($—CH_2—CH_2—$); propylene ($—(CH_2)_3—$); cyclohexylene ($—C_6H_{10}—$); —CH═CH—CH═CH—; —CH═CH—$CH_2$—; $—(CH_2)_q—N(R)—(CH_2)_r—$, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl ($—O—CH_2—O—$); and ethylenedioxyl ($—O—(CH_2)_2—O—$). An alkylene group can have about 2 to about 3 carbon atoms and can further have 6-20 carbons.

"Arylene" refers to a bivalent aryl group, which can be substituted or unsubstituted.

The term "aralkylene" refers to a bivalent group that comprises a combination of alkylene and arylene groups (e.g., -arylene-alkylene-, alkylene-arylene-alkylene-, arylene-alkylene-arylene-, etc.).

As used herein, the term "acyl" refers to an organic carboxylic acid group wherein the —OH of the carboxylic acid group has been replaced with another substituent. Thus, an acyl group can be represented by RC(═O)—, wherein R is an alkyl, substituted alkyl, aralkyl, substituted aralkyl, aryl or substituted aryl group as defined herein. As such, the term "acyl" specifically includes arylacyl groups, such as a phenacyl group. Specific examples of acyl groups include acetyl and benzoyl.

"Alkoxyl" refers to an alkyl-O— group wherein alkyl is as previously described, including substituted alkyl. The term "alkoxyl" as used herein can refer to, for example, methoxyl, ethoxyl, propoxyl, isopropoxyl, butoxyl, t-butoxyl, and pentoxyl. The term "oxyalkyl" can be used interchangably with "alkoxyl".

"Aryloxyl" refers to an aryl-O— group wherein the aryl group is as previously described, including a substituted aryl. The term "aryloxyl" as used herein can refer to phenyloxyl or hexyloxyl, and to alkyl, substituted alkyl, or alkoxyl substituted phenyloxyl or hexyloxyl.

"Aralkyl" refers to an aryl-alkyl- or an -alkyl-aryl group wherein aryl and alkyl are as previously described and can include substituted aryl and substituted alkyl. Thus, "substituted aralkyl" can refer to an aralkyl group comprising one or more alkyl or aryl group substituents. Exemplary aralkyl groups include benzyl, phenylethyl, and naphthylmethyl.

"Aralkyloxyl" or "aralkoxyl" refer to an aralkyl-O— group wherein the aralkyl group is as previously described. An exemplary aralkyloxyl group is benzyloxyl.

The term "carbonyl" refers to the group —C(═O)—. The term "carbonyl carbon" refers to a carbon atom of a carbonyl group. Other groups such as, but not limited to, acyl groups, anhydrides, aldehydes, esters, lactones, amides, ketones, carbonates, and carboxylic acids, include a carbonyl group.

The term "carboxyl" refers to the —C(═O)OH or $—C(═O)O^-$ group.

The term "acid chloride" can refer to the —C(═O)Cl group.

The terms "halo" or "halogen" as used herein refer to fluoro, chloro, bromo, and iodo groups.

The term "sulfonyl" refers to the $—S(═O)_2R$ group, wherein R is alkyl, substituted alkyl, aralkyl, substituted aralkyl, aryl, or substituted aryl. The term "alkylsulfonyl" refers to the $—S(═O)_2R$ group, wherein R is alkyl or substituted alkyl.

The term "sulfinyl" refers to the —S(═O)R group, wherein R is alkyl, substituted alkyl, aralkyl, substituted aralkyl, aryl, or substituted aryl.

The term "ester" refers to the R'—O—C(═O)— group, wherein the carbonyl carbon is attached to another carbon atom and wherein R' is alkyl, cycloalkyl, aralkyl, or aryl, wherein the alkyl, cycloalkyl, aralkyl, or aryl are optionally substituted. The term "esterifying" can refer to forming an ester by contacting a compound containing a carboxylic acid or derivative thereof (e.g., an acid chloride) and a compound containing a hydroxyl group (e.g., an alcohol or a phenol).

The term "amide" refers to the R'—NR"—C(═O)— group, wherein the carbonyl carbon is attached to another carbon atom and wherein R' and R" are independently hydrogen, alkyl, cycloalkyl, aralkyl, or aryl, wherein the alkyl, cycloalkyl, aralkyl, or aryl are optionally substituted.

A structure represented generally by a formula such as:

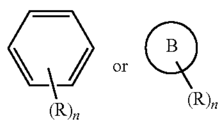

as used herein refers to a ring structure, for example, but not limited to a 3-carbon, a 4-carbon, a 5-carbon, a 6-carbon, and the like, aliphatic and/or aromatic cyclic compound comprising a substituent R group, wherein the R group can be present or absent, and when present, one or more R groups can each be substituted on one or more available carbon atoms of the ring structure. The presence or absence of the R group and number of R groups is determined by the value of the integer n. Each R group, if more than one, is substituted on an available carbon of the ring structure rather than on another R group. For example, the structure:

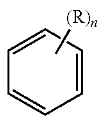

wherein n is an integer from 0 to 2 comprises compound groups including, but not limited to:

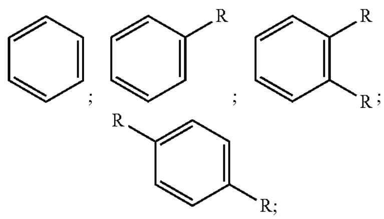

and the like.

When a named atom of an aromatic ring or a heterocyclic aromatic ring is defined as being "absent," the named atom is replaced by a direct bond. When the linking group or spacer group is defined as being absent, the linking group or spacer group is replaced by a direct bond.

The term "amine" refers to a molecule having the formula $N(R)_3$, or a protonated form thereof, wherein each R is independently H, alkyl, substituted alkyl, aryl, substituted aryl, aralkyl, substituted aralkyl, or wherein two R groups together form an alkylene or arylene group. The term "primary amine" refers to an amine wherein at least two R groups are H. The term "secondary amine" refers to an amine wherein only one R group is H. The term "alkylamine" can refer to an amine wherein two R groups are H and the other R group is alkyl or substituted alkyl. "Dialkylamine" can refer to an amine where two R groups are alkyl. "Arylamine" can refer to an amine wherein one R group is aryl. Amines can also be protonated, i.e., have the formula $[NH(R)_3]^+$.

The term "amino" refers to the group $—N(R)_2$ wherein each R is independently H, alkyl, substituted alkyl, aryl, substituted aryl, aralkyl, or substituted aralkyl. The terms "aminoalkyl" and "alkylamino" can refer to the group $—N(R)_2$ wherein each R is H, alkyl or substituted alkyl, and wherein at least one R is alkyl or substituted alkyl.

The term "cyano" refers to the —C≡N group.

The terms "halo", "halide", or "halogen" as used herein refer to fluoro, chloro, bromo, and iodo groups.

The terms "hydroxyl" and "hydroxy" refer to the —OH group.

The terms "mercapto" and "thiol" refer to the —SH group.

The term "oxo" refers to a compound described previously herein wherein a carbon atom is replaced by an oxygen atom.

The term "nitro" refers to the $—NO_2$ group.

The term "thioalkyl" can refer to the group —SR, wherein R is selected from H, alkyl, substituted alkyl, aralkyl, substituted aralkyl, aryl, and substituted aryl. Similarly, the terms "thioaralkyl" and "thioaryl" refer to —SR groups wherein R is aralkyl and aryl, respectively.

When the term "independently selected" is used, the substituents being referred to (e.g., R groups, such as groups $R_1$ and $R_2$ or groups X and Y), can be identical or different. For example, both $R_1$ and $R_2$ can be substituted alkyls, or $R_1$ can be hydrogen and $R_2$ can be a substituted alkyl, and the like.

A named "R", "R'," "X," "Y," "Y'", "A," "A'", "B," "L," or "Z" group will generally have the structure that is recognized in the art as corresponding to a group having that name, unless specified otherwise herein. For the purposes of illustration, certain representative "R," "X," and "Y" groups as set forth above are defined below. These definitions are intended to supplement and illustrate, not preclude, the definitions that would be apparent to one of ordinary skill in the art upon review of the present disclosure.

The terms "treatment" and "treating" and the like as used herein refers to any treatment of a disease and/or condition in an animal or mammal, particularly a human, and includes: (i) preventing a disease, disorder and/or condition from occurring in a person which can be predisposed to the disease, disorder and/or condition, or at risk for being exposed to an agent that can cause the disease, disorder, and/or condition; but, has not yet been diagnosed as having it; (ii) inhibiting the disease, disorder and/or condition. i.e., arresting its development; and (iii) relieving the disease, disorder and/or condition. i.e., causing regression of the disease, disorder and/or condition.

"Protecting group" as used herein includes any suitable protecting group; "protected form" refers to a substituent in which an atom such as hydrogen has been removed and replaced with a corresponding protecting group. Protecting groups are known. See generally T. H. Greene and P. G. M. Wuts. Protective Groups in Organic Synthesis, 3rd edition, John Wiley & Sons. New York (1999). Examples include but are not limited to: hydroxy protecting groups (for producing the protected form of hydroxy); carboxy protecting groups (for producing the protected form of carboxylic acid); amino-protecting groups (for producing the protected form of amino); sulfhydryl protecting groups (for producing the protected form of sulfhydryl); etc. Particular examples include but are not limited to: benzyloxycarbonyl, 4-nitrobenzyloxycarbonyl, 4-bromobenzyloxycarbonyl, 4-methoxybenzyloxycarbonyl, methoxycarbonyl, tert-butoxycarbonyl, isopropoxycarbonyl, diphenylmethoxycarbonyl, 2,2,2-trichloroethoxycarbonyl, 2-(trimethylsilyl) ethoxycarbonyl, 2-furfuryloxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, 1,1-dimethyl-2-propenyl. 3-methyl-3-butenyl, allyl, benzyl, para-methoxybenzyldiphenylmethyl, triphenylmethyl (trityl), tetrahydrofuryl, methoxymethyl, methylthiomethyl, benzyloxymethyl, 2,2, 2-triehloroethoxymethyl, 2-(trimethylsilyl)ethoxymethyl, methanesulfonyl, para-toluenesulfonyl, trimethylsilyl, triethylsilyl, triisopropylsilyl, acetyl (Ac), benzoyl (Bn), and trimethylsilyl (TMS), and the like; formyl, acetyl, benzoyl, pivaloyl, t-butylacetyl, phenylsulfonyl, benzyl, t-butyloxycarbonyl (Boc), and benzyloxycarbonyl (Cbz) and the like; and hemithioacetals such as 1-ethoxyethyl and methoxymethyl, thioesters, or thiocarbonates and the like.

The term "small molecule" refers to a compound having a molecular weight of less than about 900 daltons. In some embodiments, the molecular weight is less than about 850 daltons, less than about 800 daltons, less than about 750 daltons, less than about 700 daltons, less than about 650 daltons, less than about 600 daltons, or less than about 550 daltons.

The term "non-peptidyl" refers to a compound that does not comprise a polyamide compound comprising residues of amino acids.

II. General Considerations

Relaxin-3 is a newly identified neuropeptide, belonging to the relaxin/insulin superfamily. See Ma et al., Br. J. Pharmacol. 2017, 174, 1034; and Kumar et al., Br. J. Pharmacol. 2017, 174, 1061. The cognate receptor of relaxin-3 is RXFP3 (formally GPR135), a $G\alpha_{i/o}$ protein-coupled receptor (GPCR). Relaxin-3 binds and activates RXFP3 leading to inhibition of adenylyl cyclase and stimulation of extracellular signal-regulated kinase (ERK) 1/2 phosphorylation. Relaxin-3 is expressed predominantly in the brainstem nucleus incertus (NI) GABAergic neurons that project to a broad range of RXFP3-rich forebrain areas, including the lateral hypothalamus (LH), the paraventricular hypothalamic nucleus (PVN), amygdala (Amy), the bed nucleus of the stria terminalis (BNST), and hippocampus. Multiple lines of evidence suggest that the relaxin-3/RXFP3 neural network modulates a range of interrelated functions including responses to stress, feeding and metabolism, motivation for reward, and circadian rhythm. See Ma et al., Br. J. Pharmacol. 2017, 174, 1034; and Kumar et al., Br. J. Pharmacol. 2017, 174, 1061. Thus, compounds that can modulate the relaxin-3/RXFP3 system have the therapeutic potential to treat several diseases such as stress-associated disorders, obesity, and drug addiction. See Ma et al., Br. J. Pharmacol. 2017, 174, 1034; and Kumar et al., Br. J. Pharmacol. 2017, 174, 1061.

II.A. Relaxin-3 and Stress Response

The relaxin-3/RXFP3 system is implicated in the regulation of the stress response. The relaxin-3-containing neurons in the NI express corticotropin-releasing factor (CRF) and its receptors. See Ma et al., Br. J. Pharmacol. 2017, 174, 1034. In rats, relaxin-3 neurons are activated by CRF administration, and expression of relaxin-3 in the NI is increased in response to swim stress. See Banerjee et al., Neuropharmacology 2010, 58, 145. Similarly, repeat forced swim has been demonstrated to increase relaxin-3 expression while pretreatment with the CRF receptor-1 antagonist antalarmin attenuates the response. In a more relevant set of behavioral studies, central administration (i.c.v.) of relaxin-3 demonstrated an anxiolytic effect in the elevated plus maze test and the shock probe-burying test in rats. See Ryan et al., Behav. Brain Res. 2013, 244, 142. Similarly, i.c.v, infusion of a specific RXFP3 agonist peptide reduced anxiety-like behavior in the light-dark box and elevated plus maze. Notably, in the repeat forced swim test. RXFP3 agonist administration decreased immobility in rats that had been subjected to the 'stress' of former exposure to the anxiety tests, but not in experimentally naive rats. Taken together, these studies suggest a potential for RXFP3 agonists as anxiolytic and anti-depressant agents.

II.B. Relaxin-3 and Food Intake

Pharmacological studies consistently demonstrated that relaxin-3 and selective RXFP3 agonist peptides are potently orexigenic in rats following acute delivery into the lateral cerebral ventricle and various hypothalamic regions. See Kumar et al., Br. J. Pharmacol. 2017, 174, 1061. In addition, chronic delivery of RXFP3 agonists also increased food consumption and body weight. See Ganella et al., Gene Ther. 2013, 20, 703. Moreover, co-administration of RXFP3 antagonist peptides was able to prevent the increases in feeding induced by acute RXFP3 agonist injections. See Smith et al., Behav. Brain Res. 2014, 268, 117; and Haugaard-Kedstrom et al., J. Am. Chem. Soc. 2011, 133, 4965. These findings demonstrate therapeutic potential for RXFP3 antagonists in treating eating disorders including management of antipsychotic drug-induced weight gain and hyperphagia associated with depression.

II.C. Relaxin-3 and Drug Addiction

The relationship between stress systems and addiction has been the focus of considerable research in recent years, particularly because of the central role of CRF in both. See Zorrilla et al., Front. Neuroendocrinol. 2014, 35, 234. Recent studies have demonstrated a potential role of the relaxin-3/RXFP3 signalling in behavior related to substance use and abuse. A positive correlation between the expression of relaxin-3 mRNA and alcohol intake has been observed in alcohol-preferring rats. See Ryan et al., Drug Alcohol Depend. 2014, 140, 8. In addition, RXFP3 knockout mice displayed attenuated stress-induced alcohol preference. See Walker et al., PloS one 2015, 10 e0122504. Further, central administration of a specific RXFP3 antagonist peptide to rats decreased alcohol self-administration and attenuated both cue- and stress-induced reinstatement of alcohol-seeking. See Ryan et al., Proc. Natl. Acad. Sci., USA 2013, 110, 20789. In contrast, the RXFP3 antagonist peptide had no effects on self-administration or reinstatement of sucrose-seeking, suggesting a specific effect for alcohol. These findings support using relaxin-3/RXFP3 antagonists as a novel therapeutic tool for treating alcohol use disorders.

III. Small Molecule Antagonists for the Relaxin-3/RXFP3 System

Despite the emerging pharmacological implications of the relaxin-3/RXFP3 system, small molecule antagonists of RXFP3 have not been previously described. The currently described RXFP3 peptide antagonists have limitations as potential therapeutics as they are metabolically unstable and require administration via central injection. Relaxin-3 binds and activates its endogenous receptor RXFP3 as well as RXFP1 and RXFP4, two receptor subtypes in the relaxin family. This cross-activity, together with an overlapping expression profile of RXFP3 and RXFP1 in the brain (RXFP4 is not expressed in the brain of rodents), make a selective RXFP3 ligand critical for precise elucidation of RXFP3 functions. In order to expedite the development of small molecule ligands, a stable RXFP3-CHO cell-based cAMP functional assay for high throughput screening has been developed. See Example 2, below. A 19,000-member chemical library with a focus on GPCR pharmacophore features was screened and identified three hits belonging to one structural family, RLX-1, having the structure:

RLX-1

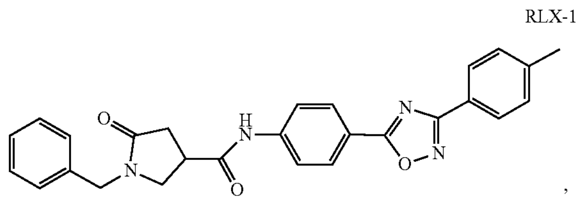 [SMILES: Cc1ccc(-c2noc(-c3ccc(NC(=O)C4CC(=O)N(Cc5ccccc5)C4)cc3)n2)cc1]

was identified as a functional RXFP3 antagonist with an $IC_{50}$ of 5.3 μM. RLX-1 had no effects on either promotion or inhibition of cAMP levels at concentrations up to 100 μM in parental CHO cells, indicating that its inhibition of relaxin-3 activity is mediated by the RXFP3 receptor. In addition, RLX-1 had no RXFP3 agonist activity.

Focused structure-activity relationship (SAR) studies have produced several analogs of RLX-1 with potencies in the submicromolar range. The potency of the compounds to inhibit relaxin-3 activity ($IC_{50}$) was determined by running a single concentration of the relaxin-3 peptide in the presence of a concentration-response curve of the test compound. The $IC_{50}$ values of select compounds are shown below in Table 1 of Example 2. It is believed that these compounds represent the first series of small molecule RXFP3 antagonists to be described. As shown in Table 1 of Example 2, RLX-19, RLX-24, and RLX-33 with $IC_{50}$ values of 1.3 μM, 1.2 μM and 2.9 μM, respectively, are among the most potent compounds. RLX-33 is highly selective for RXFP3 relative to RXFP1, as it has no activity at RXFP1 at all concentrations tested up to 30 μM.

Accordingly, in some embodiments, the presently disclosed subject matter provides a non-peptidyl small molecule compound that has antagonist activity toward RXFP3. In some embodiments, the compound can have an $IC_{50}$ for RXFP3 in the presence of relaxin-3 of less than about 10 micromolar (μM). In some embodiments, the compound has an $IC_{50}$ of less than about 5 μM or less than about 2 μM. In some embodiments, the compound has an $IC_{50}$ of about 1 μM.

In some embodiments, the compound selectively inhibits RXFP3 compared to RXFP1 and/or RXFP4. In some embodiments, the compound has an $IC_{50}$ for RXFP3 that is at least about 5 times lower than its $IC_{50}$ for RXFP1. In some embodiments, the compound has an $IC_{50}$ for RXFP3 that is at least about 10 times lower (e.g., at least about 10 times lower, at least about 25 times lower, or at least about 50 times lower) than its $IC_{50}$ for RXFP1. In some embodiments, the compound has an $IC_{50}$ for RXFP3 that is at least about 100 times lower than its $IC_{50}$ for RXPF1.

The presently disclosed small molecule compounds can have a molecular weight of less than about 900 daltons (e.g., less than about 850, less than about 800, less than about 750, less than about 700, less than about 650, less than about 600, or less than about 550 daltons). In some embodiments, the compounds can comprise a N-substituted gamma (γ) or delta (δ) lactam (i.e., a N-substituted 2-pyrrolidone or N-substituted 2-piperidinone) further comprising an acyl substituent attached to a carbon atom of the lactam ring. In some embodiments, the acyl substituent is an amide. In some embodiments, the acyl substituent is an N-aryl amide. For example, the N-aryl amide can comprise a phenyl or pyridine group attached to the amide nitrogen atom, wherein the phenyl or pyridine group can be further substituted with one or more substituents, optionally including at least one 5-membered heterocycle, wherein the 5-membered heterocycle can also be further substituted. In some embodiments, the 5-membered heterocycle comprises at least one nitrogen atom and at least one oxygen atom.

In some embodiments, the compound has a structure of Formula (I):

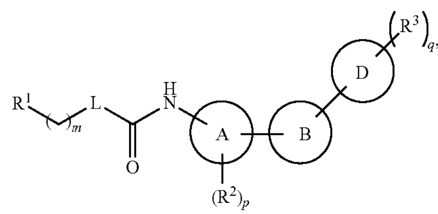

Wherein: L is

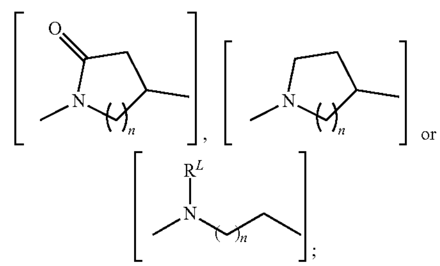

or n is an integer between 1 and 3; $R^L$ is selected from the group comprising hydrogen, C1-C6 substituted or unsubstituted alkyl, C2-C6 substituted or unsubstituted alkenyl, C3-C6 substituted or unsubstituted cycloalkyl, substituted or unsubstituted heterocyclo, substituted or unsubstituted aryl, and substituted or unsubstituted heteroaryl; m is an integer between 0 and 3; p is an integer between 0 and 3; q is an integer between 0 and 3; A is selected from phenyl and pyridinyl; B is a five-membered heterocyclic group; D is present or absent and when present is selected from substituted or unsubstituted aryl and substituted or unsubstituted heteroaryl; $R^1$ is selected from the group comprising hydrogen, alkyl (e.g., C1-C6 substituted or unsubstituted alkyl), alkenyl (e.g., C2-C6 substituted or unsubstituted alkenyl), cycloalkyl (e.g., C3-C6 substituted or unsubstituted cycloalkyl), substituted or unsubstituted heterocyclo, substituted or unsubstituted aryl, and substituted or unsubstituted heteroaryl; each $R^2$ is independently selected from the group comprising alkyl (e.g., substituted or unsubstituted C1-C6 alkyl), alkenyl (e.g., substituted or unsubstituted C3-C6 alkenyl), cycloalkyl (e.g., C1-C6 substituted or unsubstituted cycloalkyl), alkoxy (e.g., C1-C6 alkoxy); substituted or unsubstituted heterocyclo, halo, nitro, cyano, amino, alkylsulfonyl, ester and amide; and each $R^3$ is independently selected from the group comprising alkyl (e.g., C1-C6 substituted or unsubstituted alkyl), alkenyl (e.g., C2-C6 substituted or unsubstituted alkenyl), cycloalkyl (e.g., C3-C6 substituted or unsubstituted cycloalkyl), alkoxy (e.g., C1-C6 alkoxy), substituted or unsubstituted heterocyclo, halo, nitro, cyano, amino, alkylsulfonyl, ester, and amide; or a pharmaceutically acceptable salt thereof.

The five-membered heterocycle B can be any suitable five-membered heterocycle comprising 1, 2, or 3 heteroatoms. In some embodiments, B can be selected from the group including, but not limited to, furan, thiophene, pyrrole, oxazole, thiazole, imidazole, isoxazole, isothiazole, pyrazole, oxadiazole, thiadiazole, and triazole. In some embodiments, B includes at least one or two nitrogen atoms. In some embodiments, B is an oxadiazole. In some embodiments, B is 1,2,4-oxadiazole In some embodiments, m is 1, 2, or 3. In some embodiments, m is 1.

In some embodiments, $R^1$ is a substituted or unsubstituted aryl or heteroaryl group. In some embodiments, $R^1$ is substituted or unsubstituted phenyl. In some embodiments, $R^1$ is a substituted or unsubstituted five-membered or six-membered heteroaryl group (e.g., pyridinyl, thiophenyl, or furanyl). In some embodiments, m is 1, 2, or 3 and $R^1$ is selected from a substituted or unsubstituted phenyl, a substituted or unsubstituted five-membered heteroaryl, and a substituted or unsubstituted six-membered heteroaryl. In some embodiments, the $R^1$ phenyl, five-membered heteroaryl, or six-membered heteroaryl group is further substituted with one or more aryl group substituents, including, but not limited to alkyl (e.g., C1-C6 alkyl), alkenyl (e.g., C2-C6 alkenyl), alkoxy (e.g., C1-C6 alkoxy), cycloalkyl (e.g., C3-C6 cycloalkyl), heterocyclo, halo, nitro, cyano, amino, alkylsulfonyl, ester, and amide.

In some embodiments, n is 2 and the compound comprises a piperidinone. In some embodiments, the piperidinone is a N-benzyl substituted piperidinone. In some embodiments, A is phenyl. In some embodiments, D is phenyl. In some embodiments, the compound is:

RLX-34

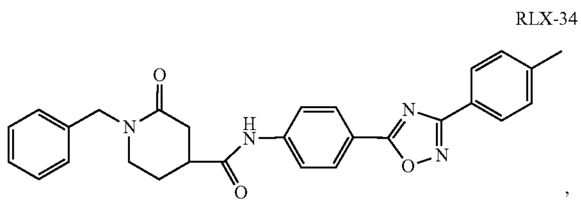 [SMILES: Cc1ccc(-c2noc(-c3ccc(NC(=O)C4CCN(Cc5ccccc5)C(=O)C4)cc3)n2)cc1]

, or a pharmaceutically acceptable salt thereof.

In some embodiments, n is 1 and the compound comprises a pyrrolidone. In some embodiments, the pyrrolidone is a N-substituted pyrrolidone. In some embodiments, the phenyl or pyridine group A is bonded to the carbon at the 3-position of 1,2,4-oxadiazole. In some embodiments, the compound is:

RLX-36

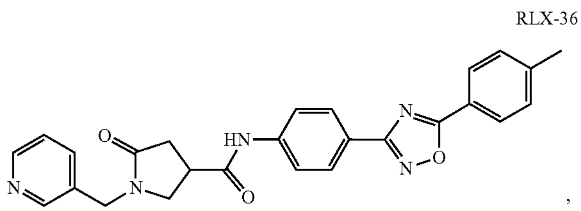 [SMILES: Cc1ccc(-c2nc(-c3ccc(NC(=O)C4CC(=O)N(Cc5cccnc5)C4)cc3)no2)cc1]

, or a pharmaceutically acceptable salt thereof.

In some embodiments, the phenyl or pyridine group A is bonded to the carbon at the 5-position of 1,2,4-oxadiazole. In some embodiments, the compound has a structure of Formula (II):

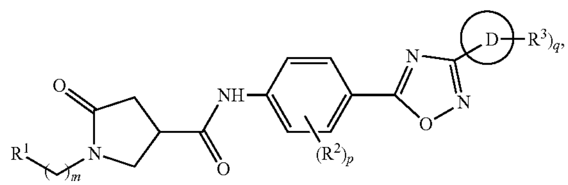

wherein: m is an integer between 0 and 3; p is an integer between 0 and 3; q is an integer between 0 and 3; D is present or absent, and when present is selected from substituted or unsubstituted aryl and substituted or unsubstituted heteroaryl; $R^1$ is selected from the group comprising hydrogen, alkyl (e.g., C1-C6 substituted or unsubstituted alkyl), alkenyl (e.g., C2-C6 substituted or unsubstituted alkenyl), cycloalkyl (e.g., C3-C6 substituted or unsubstituted cycloalkyl), substituted or unsubstituted heterocyclo, substituted or unsubstituted aryl, and substituted or unsubstituted heteroaryl; each $R^2$ is independently selected from the group comprising alkyl (e.g., C1-C6 substituted or unsubstituted alkyl), alkenyl (e.g., C3-C6 substituted or unsubstituted alkenyl), cycloalkyl (C1-C6 substituted or unsubstituted cycloalkyl), alkoxy (C1-C6 alkoxy); substituted or unsubstituted heterocyclo, halo, nitro, cyano, amino, alkylsulfonyl, ester, and amide; and each $R^3$ is independently selected from the group comprising alkyl (e.g., C1-C6 substituted or unsubstituted alkyl), alkenyl (e.g., C2-C6 substituted or unsubstituted alkenyl), cycloalkyl (e.g., C3-C6 substituted or unsubstituted cycloalkyl), alkoxy (e.g., C1-C6 alkoxy), substituted or unsubstituted heterocyclo, halo, nitro, cyano, amino, alkylsulfonyl, ester, and amide; or a pharmaceutically acceptable salt thereof. In some embodiments, p is 0.

In some embodiments, D is absent, and q is 1. Thus, in some embodiments, an $R^3$ group is directly attached to B. In some embodiments. D is absent, q is 1 and $R^3$ is substituted or unsubstituted alkyl (e.g., C1-C6 unsubstituted alkyl or C1-C6 substituted alkyl). In some embodiments, $R^3$ is substituted alkyl (i.e., C1-C6 substituted alkyl), wherein the alkyl group is substituted by phenyl or substituted phenyl. Thus, in some embodiments, the 1,2,4-oxadiazole group is substituted by benzyl or substituted benzyl. In some embodiments, m is 1 and $R^1$ is aryl or heteroaryl. In some embodiments $R^1$ is pyridinyl. In some embodiments, the compound is selected from:

RLX-31

RLX-35

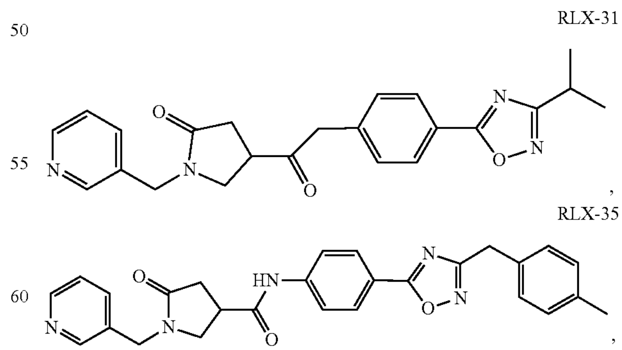

,

, and pharmaceutically acceptable salts thereof.

In some embodiments D is present. D can be, for example, phenyl, a five-membered heteroaryl group, or a six-membered heteroaryl group. In some embodiments, D is a six-membered heteroaryl group comprising at least one nitrogen. In some embodiments, D is phenyl or pyridinyl. In some embodiments, m is 1 and $R^1$ is selected from alkyl (e.g., C1-C6 alkyl), aryl, substituted aryl, and heteroaryl. In some embodiments, $R^1$ is selected from methyl, phenyl, substituted phenyl, pyridinyl, thiophenyl, and furanyl.

In some embodiments, m is 1, $R^1$ is pyridinyl, D is pyridinyl, and q is 0. In some embodiments, the compound is selected from:

RLX-28

RLX-29

RLX-30

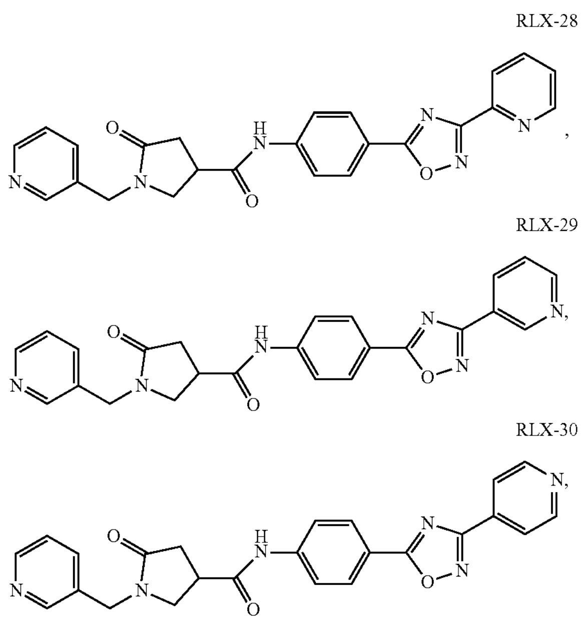

and pharmaceutically acceptable salts thereof.

In some embodiments, D is phenyl. In some embodiments, q is 1 or 2 and $R^3$ is selected from alkyl (e.g., C1-C6 substituted or unsubstituted alkyl), alkoxy (e.g., C1-C6 alkoxy), halo, and amino. In some embodiments, $R^3$ is selected from methyl, ethyl, isopropyl, fluoro, chloro, bromo, trifluoromethyl, methoxy, and dimethylamino. In some embodiments, q is 0.

In some embodiments, $R^1$ is phenyl or substituted phenyl, optionally wherein said substituted phenyl is phenyl substituted by one or more alkyl (e.g., C1-C6 alkyl), halo, or alkoxy (e.g., C1-C6 alkoxy). In some embodiments, the compound is selected from the group comprising:

RLX-1

RLX-2

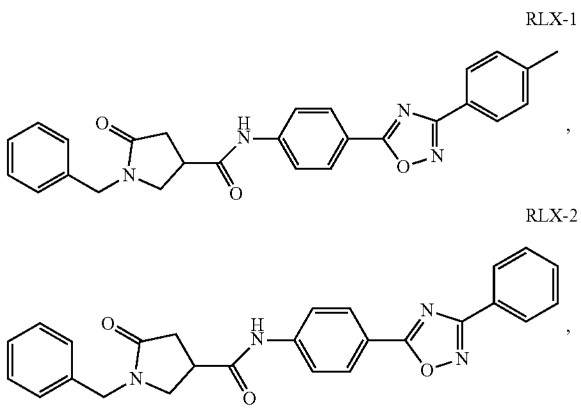

-continued

RLX-3

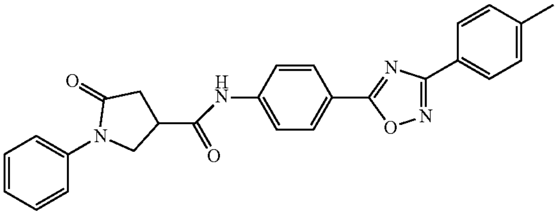

,

RLX-4

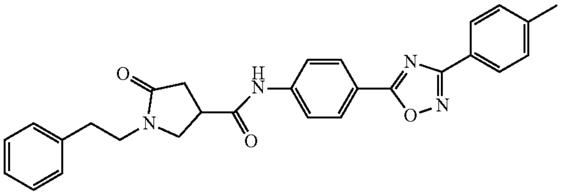

,

RLX-5

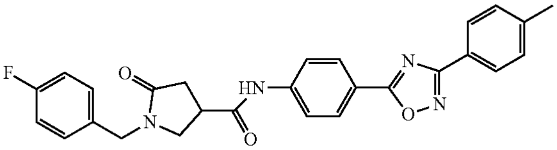

,

RLX-6

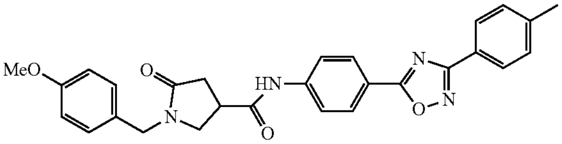

,

RLX-7

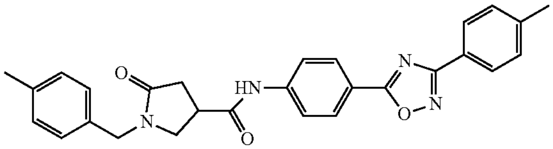

,

RLX-8

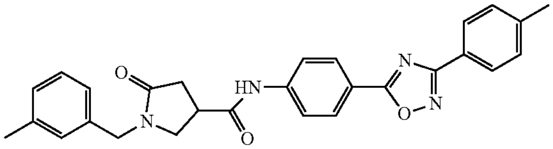

, and pharmaceutically acceptable salts thereof.

In some embodiments, $R^1$ is alkyl (e.g., C1-C6 unsubstituted alkyl, such as methyl, ethyl, n-propyl, isopropyl, n-butyl, isobutyl, sec-butyl, tert-butyl, etc.). In some embodiments, R' is methyl. In some embodiments, m is 1. In some embodiments, the compound is:

RLX-15

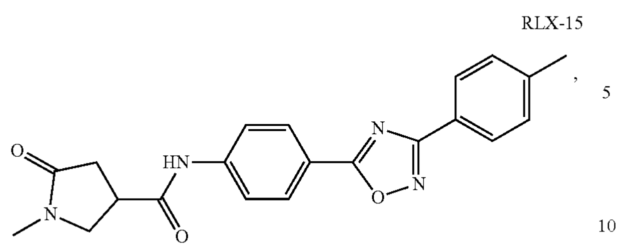

, or a pharmaceutically acceptable salt thereof.

In some embodiments, m is 1 and $R^1$ is heteroaryl. In some embodiments, $R^1$ is selected from pyridinyl, thiophenyl, or furanyl. In some embodiments, $R^1$ is furan-2-yl, thiophen-2-yl, or thiophen-3-yl. In some embodiments, q is 1 and $R^3$ is alkyl (e.g., C1-C6 alkyl), optionally methyl. In some embodiments, the compound is selected from the group comprising, but not limited to:

RLX-12

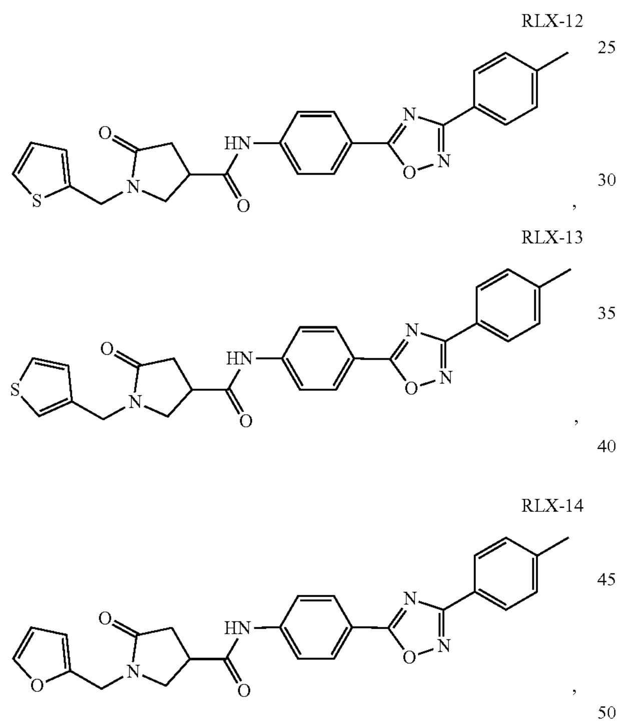

, RLX-13

, RLX-14

, and pharmaceutically acceptable salts thereof.

In some embodiments, $R^1$ is furan-2-yl. In some embodiments, q is 1 and $R^3$ is halo or substituted alkyl (e.g., C1-C6 substituted alkyl, optionally perhaloalkyl). In some embodiments, the compound is selected from:

RLX-32

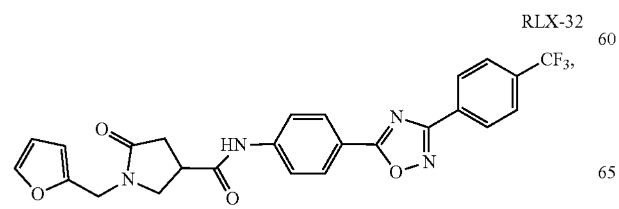

-continued

RLX-33

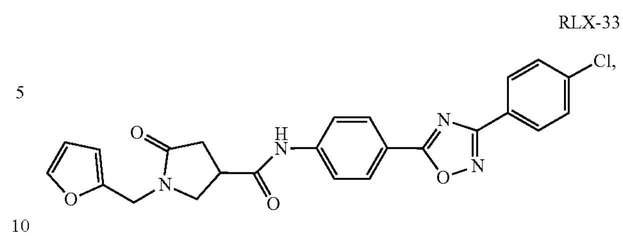

and pharmaceutically acceptable salts thereof.

In some embodiments, $R^1$ is pyridinyl. In some embodiments, $R^1$ is 3-pyridinyl. In some embodiments, q is 0. In some embodiments, q is 1 or 2 and $R^3$ is selected from halo, alkyl (e.g., C1-C6 alkyl), substituted alkyl (e.g., substituted C1-C6 alkyl), alkoxy (e.g., C1-C6 alkyl), and amino (e.g., dialkylamino). In some embodiments, $R^3$ is —$CF_3$, chloro, or bromo. In some embodiments, $R^3$ is methyl, ethyl, or isopropyl. In some embodiments, $R^3$ is methoxy. In some embodiments, $R^3$ is dimethylamino. In some embodiments, the compound is selected from the group comprising:

RLX-9

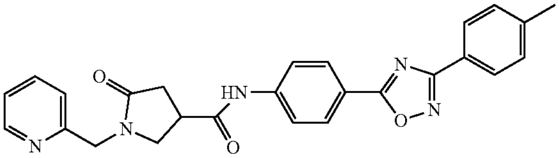

,

RLX-10

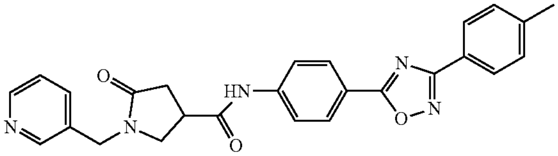

,

RLX-11

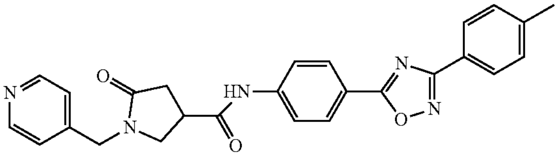

,

RLX-16

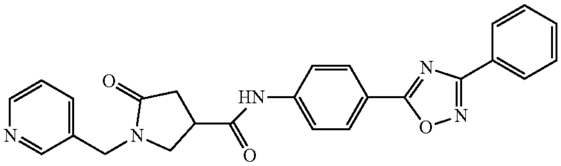

,

RLX-17

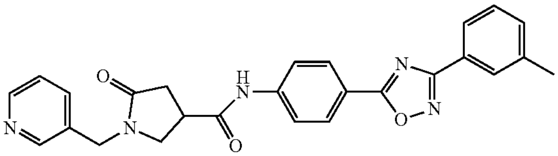

,

-continued

RLX-18

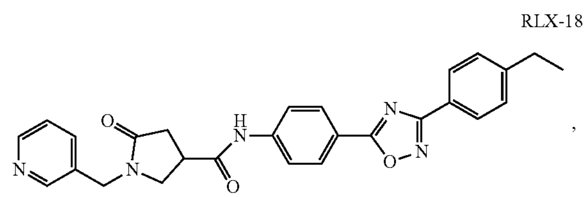

,

RLX-19

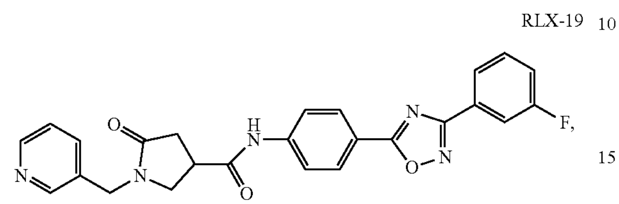

RLX-20

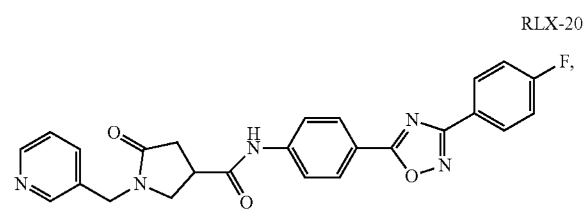

RLX-21

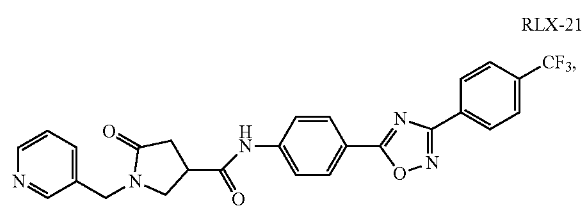

RLX-22

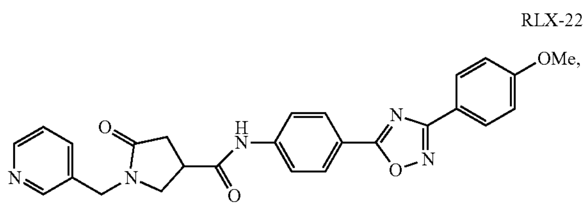

RLX-23

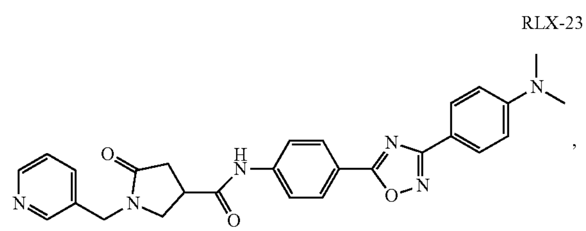

,

RLX-24

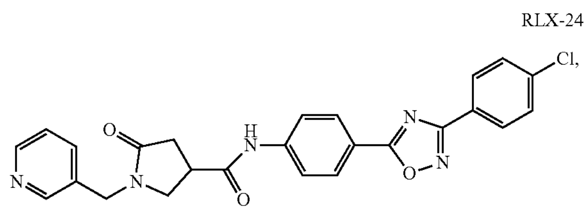

RLX-25

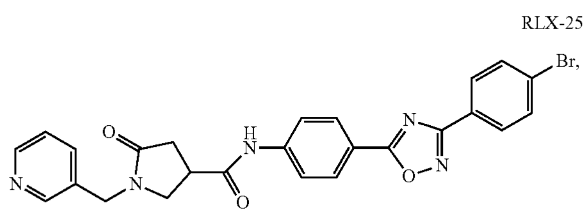

-continued

RLX-26

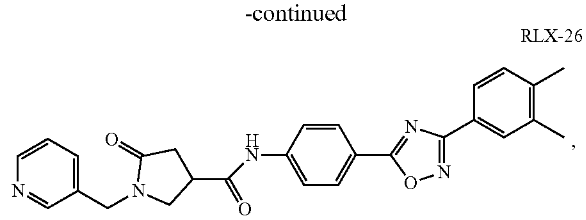

,

RLX-27

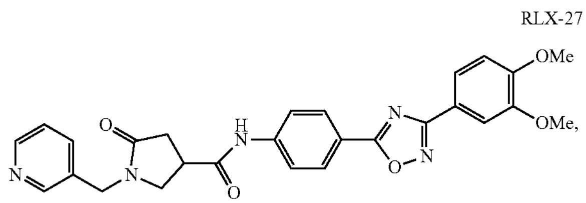

and pharmaceutically acceptable salts thereof.

In some embodiments, the compound has a structure of Formula (III):

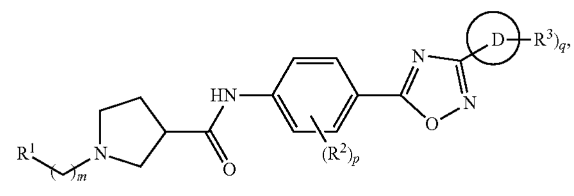

wherein: m is an integer between 0 and 3; p is an integer between 0 and 3; q is an integer between 0 and 3; D is present or absent, and when present is selected from substituted or unsubstituted aryl and substituted or unsubstituted heteroaryl; $R^1$ is selected from the group comprising hydrogen, C1-C6 substituted or unsubstituted alkyl, C2-C6 substituted or unsubstituted alkenyl, C3-C6 substituted or unsubstituted cycloalkyl, substituted or unsubstituted heterocyclo, substituted or unsubstituted aryl, and substituted or unsubstituted heteroaryl; each $R^2$ is independently selected from the group comprising substituted or unsubstituted C1-C6 alkyl, substituted or unsubstituted C3-C6 alkenyl, C3-C6 substituted or unsubstituted cycloalkyl, C1-C6 alkoxy; substituted or unsubstituted heterocyclo, halo, nitro, cyano, amino, alkylsulfonyl, ester and amide; and each $R^3$ is independently selected from C1-C6 substituted or unsubstituted alkyl, C2-C6 substituted or unsubstituted alkenyl, C3-C6 substituted or unsubstituted cycloalkyl, C1-C6 alkoxy, substituted or unsubstituted heterocyclo, halo, nitro, cyano, amino, alkylsulfonyl, ester, and amide; or a pharmaceutically acceptable salt thereof.

In some embodiments, $R^1$ is phenyl and D is phenyl. In some embodiments, the compound is:

RLX-37

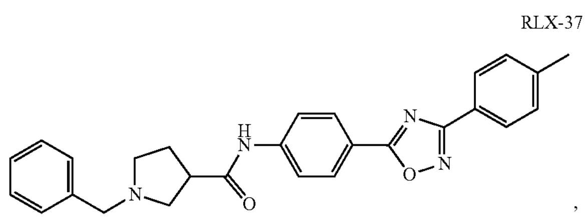 [SMILES: Cc1ccc(-c2noc(-c3ccc(NC(=O)C4CCN(Cc5ccccc5)C4)cc3)n2)cc1]

, and pharmaceutically acceptable salts thereof.

In some embodiments, the compound has a structure of Formula (IV):

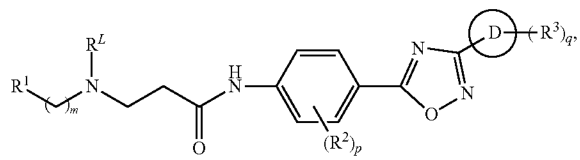

wherein: m is an integer between 0 and 3; p is an integer between 0 and 3; q is an integer between 0 and 3; D is present or absent, and when present is selected from substituted or unsubstituted aryl and substituted or unsubstituted heteroaryl; $R^1$ is selected from the group comprising hydrogen. C1-C6 substituted or unsubstituted alkyl, C2-C6 substituted or unsubstituted alkenyl, C3-C6 substituted or unsubstituted cycloalkyl, substituted or unsubstituted heterocyclo, substituted or unsubstituted aryl, and substituted or unsubstituted heteroaryl; $R^L$ is selected from the group comprising hydrogen, C1-C6 substituted or unsubstituted alkyl, C2-C6 substituted or unsubstituted alkenyl, C3-C6 substituted or unsubstituted cycloalkyl, substituted or unsubstituted heterocyclo, substituted or unsubstituted aryl, and substituted or unsubstituted heteroaryl; each $R^2$ is independently selected from the group comprising substituted or unsubstituted C1-C6 alkyl, substituted or unsubstituted C3-C6 alkenyl, C3-C6 substituted or unsubstituted cycloalkyl, C1-C6 alkoxy; substituted or unsubstituted heterocyclo, halo, nitro, cyano, amino, alkylsulfonyl, ester and amide; and each $R^3$ is independently selected from C1-C6 substituted or unsubstituted alkyl, C2-C6 substituted or unsubstituted alkenyl, C3-C6 substituted or unsubstituted cycloalkyl, C1-C6 alkoxy, substituted or unsubstituted heterocyclo, halo, nitro, cyano, amino, alkylsulfonyl, ester, and amide; or a pharmaceutically acceptable salt thereof.

In some embodiments, $R^1$ is phenyl and D is phenyl. In some embodiments, $R^L$ is methyl or hydrogen, and the compound is selected from:

RLX-38

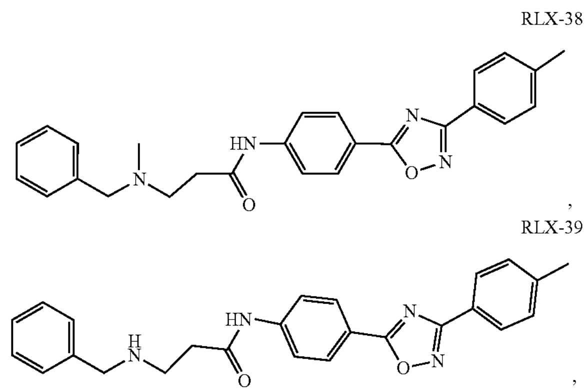

,

RLX-39

, and pharmaceutically acceptable salts thereof.

As indicated above, it is to be understood that the disclosed compounds can comprise pharmaceutically acceptable salts. Such salts include, but are not limited to, pharmaceutically acceptable acid addition salts, pharmaceutically acceptable base addition salts, pharmaceutically acceptable metal salts, ammonium and alkylated ammonium salts, and combinations thereof.

Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, sulphates, nitrates, phosphates, perchlorates, borates, acetates, benzoates, hydroxynaphthoates, glycerophosphates, ketoglutarates and the like.

Base addition salts include but are not limited to, ethylenediamine, N-methyl-glucamine, lysine, arginine, ornithine, choline, N, N'-dibenzylethylenediamine, chloroprocaine, diethanolamine, procaine, N-benzylphenethylamine, diethylamine, piperazine, tris (hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e. g., lysine and arginine dicyclohexylamine and the like.

Examples of metal salts include lithium, sodium, potassium, magnesium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like. Examples of organic bases include lysine, arginine, guanidine, diethanolamine, choline and the like.

IV. Pharmaceutical Compositions

The compounds disclosed herein can be formulated in accordance with the routine procedures adapted for a desired administration route. Accordingly, in some embodiments, the presently disclosed subject matter provides a pharmaceutical composition comprising a therapeutically effective amount of a compound as disclosed hereinabove (e.g., a compound of Formula (I) or Formula (II)) and a pharmaceutically acceptable carrier. The therapeutically effective amount can be determined by testing the compounds in an in vitro or in vivo model and then extrapolating therefrom for dosages in subjects of interest, e.g., humans. The therapeutically effective amount should be enough to exert a therapeutically useful effect in the absence of undesirable side effects in the subject to be treated with the composition.

Pharmaceutically acceptable carriers are well known to those skilled in the art and include, but are not limited to, from about 0.01 to about 0.1M and preferably 0.05M phosphate buffer or 0.8% saline. Such pharmaceutically acceptable carriers can be aqueous or non-aqueous solutions, suspensions, and emulsions. Examples of non-aqueous solvents suitable for use in the presently disclosed subject matter include, but are not limited to, propylene glycol, polyethylene glycol, vegetable oils such as olive oil, and injectable organic esters such as ethyl oleate. Aqueous carriers suitable for use in the presently disclosed subject matter include, but are not limited to, water, ethanol, alcoholic/aqueous solutions, glycerol, emulsions, or suspensions, including saline and buffered media. Oral carriers can be elixirs, syrups, capsules, tablets, and the like.

Liquid carriers suitable for use in the presently disclosed subject matter can be used in preparing solutions, suspensions, emulsions, syrups, elixirs, and pressurized compounds. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers, or osmo-regulators.

Liquid carriers suitable for use in the presently disclosed subject matter include, but are not limited to, water (partially containing additives as above, e.g., cellulose derivatives, preferably sodium carboxymethyl cellulose solution), alcohols (including monohydric alcohols and polyhydric alcohols, e.g., glycols) and their derivatives, and oils (e.g., fractionated coconut oil and arachis oil). For parenteral administration, the carrier can also include an oily ester such as ethyl oleate and isopropyl myristate. Sterile liquid carriers are useful in sterile liquid form comprising compounds for parenteral administration. The liquid carrier for pressurized compounds disclosed herein can be halogenated hydrocarbon or other pharmaceutically acceptable propellent.

Solid carriers suitable for use in the presently disclosed subject matter include, but are not limited to, inert substances such as lactose, starch, glucose, methyl-cellulose, magnesium stearate, dicalcium phosphate, mannitol and the like. A solid carrier can further include one or more substances acting as flavoring agents, lubricants, solubilizers, suspending agents, fillers, glidants, compression aids, binders, or tablet-disintegrating agents; it can also be an encapsulating material. In powders, the carrier can be a finely divided solid which is in admixture with the finely divided active compound. In tablets, the active compound is mixed with a carrier having the necessary compression properties in suitable proportions and compacted in the shape and size desired. The powders and tablets preferably contain up to 99% of the active compound. Suitable solid carriers include, for example, calcium phosphate, magnesium stearate, talc, sugars, lactose, dextrin, starch, gelatin, cellulose, polyvinylpyrrolidine, low melting waxes and ion exchange resins.

Parenteral carriers suitable for use in the presently disclosed subject matter include, but are not limited to, sodium chloride solution, Ringer's dextrose, dextrose and sodium chloride, lactated Ringer's and fixed oils. Intravenous carriers include fluid and nutrient replenishers, electrolyte replenishers such as those based on Ringer's dextrose and the like. Preservatives and other additives can also be present, such as, for example, antimicrobials, antioxidants, chelating agents, inert gases, and the like.

Carriers suitable for use in the presently disclosed subject matter can be mixed as needed with disintegrants, diluents, granulating agents, lubricants, binders, and the like using conventional techniques known in the art. The carriers can also be sterilized using methods that do not deleteriously react with the compounds, as is generally known in the art. The compounds disclosed herein can take such forms as suspensions, solutions, or emulsions in oily or aqueous vehicles, and can contain formulatory agents such as suspending, stabilizing and/or dispersing agents. The compounds disclosed herein can also be formulated as a preparation for implantation or injection. Thus, for example, the compounds can be formulated with suitable polymeric or hydrophobic materials (e.g., as an emulsion in an acceptable oil) or ion exchange resins, or as sparingly soluble derivatives (e.g., as a sparingly soluble salt). Alternatively, the active ingredient can be in powder form for constitution with a suitable vehicle, e.g., sterile pyrogen-free water, before use. Suitable formulations for each of these methods of administration can be found, for example, in *Remington: The Science and Practice of Pharmacy*, A. Gennaro, ed., 20th edition, Lippincott, Williams & Wilkins, Philadelphia, Pa.

For example, formulations for parenteral administration can contain as common excipients sterile water or saline, polyalkylene glycols such as polyethylene glycol, oils of vegetable origin, hydrogenated naphthalenes and the like. In particular, biocompatible, biodegradable lactide polymer, lactide/glycolide copolymer, or polyoxyethylene-polyoxypropylene copolymers can be useful excipients to control the release of active compounds. Other potentially useful parenteral delivery systems include ethylene-vinyl acetate copolymer particles, osmotic pumps, implantable infusion systems, and liposomes. Formulations for inhalation administration contain as excipients, for example, lactose, or can be aqueous solutions containing, for example, polyoxyethylene-9-auryl ether, glycocholate and deoxycholate, or oily solutions for administration in the form of nasal drops, or as a gel to be applied intranasally. Formulations for parenteral administration can also include glycocholate for buccal administration, methoxysalicylate for rectal administration, or citric acid for vaginal administration.

Further, formulations for intravenous administration can comprise solutions in sterile isotonic aqueous buffer. Where necessary, the formulations can also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachet indicating the quantity of active agent. Where the compound is to be administered by infusion, it can be dispensed in a formulation with an infusion bottle containing sterile pharmaceutical grade water, saline, or dextrose/water. Where the compound is administered by injection, an ampule of sterile water for injection or saline can be provided so that the ingredients can be mixed prior to administration.

Suitable formulations further include aqueous and non-aqueous sterile injection solutions that can contain antioxidants, buffers, bacteriostats, bactericidal antibiotics and solutes that render the formulation isotonic with the bodily fluids of the intended recipient; and aqueous and non-aqueous sterile suspensions, which can include suspending agents and thickening agents.

The compounds can further be formulated for topical administration. Suitable topical formulations include one or more compounds in the form of a liquid, lotion, cream, or gel. Topical administration can be accomplished by application directly on the treatment area. For example, such application can be accomplished by rubbing the formulation (such as a lotion or gel) onto the skin of the treatment area, or by spray application of a liquid formulation onto the treatment area.

In some formulations, bioimplant materials can be coated with the compounds so as to improve interaction between cells and the implant.

Formulations of the compounds can contain minor amounts of wetting or emulsifying agents, or pH buffering agents. The formulations comprising the compound can be a liquid solution, suspension, emulsion, tablet, pill, capsule, sustained release formulation, or powder.

The compounds can be formulated as a suppository, with traditional binders and carriers such as triglycerides.

Oral formulations can include standard carriers such as pharmaceutical grades of mannitol, lactose, starch, magnesium stearate, polyvinyl pyrollidone, sodium saccharine, cellulose, magnesium carbonate, etc.

In some embodiments, the pharmaceutical composition comprising the compound of the presently disclosed subject matter can include an agent which controls release of the compound, thereby providing a timed or sustained release compound.

V. Methods of Treatment

Without wishing to be bound by theory or mechanism of action, it is believed that "normal" relaxin-3 signalling in the brain is advantageous in survival and is thought to broadly increase arousal, attention, motivation and promote learning and memory, for example. However, in pathological situations, when the stress system is hyperactive and dysfunctional, relaxin-3 signaling might be overstimulated. If this is chronic, ongoing hyperactive relaxin-3 signalling (i.e., ongoing elevated levels of relaxin-3 in the brain) becomes detrimental to health, and an antagonist thus becomes therapeutically useful. It is believed that G-protein coupled receptors such as RXFP3 can be altered, in expression and or activation, in a variety of disease states and hence themselves represent targets for the development of therapeutics.

Accordingly, in some embodiments, the presently disclosed subject matter provides a method of treating a disease or condition associated with aberrant expression and/or activity or relaxin-3 or associated with aberrant expression and/or activity of the RXFP3 receptor in a subject in need thereof, the method comprising administering to said subject an effective amount of a small molecule RXFP3 antagonist compound as described above or a pharmaceutical composition comprising such a compound. In some embodiments, the disease or condition is a disease or condition wherein inhibition of biological activity at, or signalling via, the RXFP3 receptor is desirable.

With respect to the methods of the presently disclosed subject matter, a preferred subject is a vertebrate subject. A preferred vertebrate is warm-blooded; a preferred warm-blooded vertebrate is a mammal. The subject treated by the presently disclosed methods is desirably a human, although it is to be understood that the principles of the presently disclosed subject matter indicate effectiveness with respect to all vertebrate species which are to be included in the term "subject." In this context, a vertebrate is understood to be any vertebrate species in which treatment of a relaxin-3- and/or RXFP3-associated disease or condition is desirable. As used herein, the term "subject" includes both human and animal subjects. Thus, veterinary therapeutic uses are provided in accordance with the presently disclosed subject matter.

As such, the presently disclosed subject matter provides for the treatment of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economical importance to humans. Thus, also provided is the treatment of livestock, including, but not limited to, domesticated swine, ruminants, ungulates, horses (including race horses), poultry, and the like. In some embodiments, the subject is a human.

Diseases and conditions associated with aberrant expression and/or activity of relaxin-3 or the RXFP3 receptor include, for instance, anxiety disorders, obesity and/or eating disorders, mood disorders, cognitive disorders, neurodevelopmental disorders, personality disorders, psychotic disorders, alcoholism, and other substance abuse-related disorders. Anxiety disorders treatable according to the presently disclosed methods include, for example, generalized anxiety disorder (GAD), post-traumatic stress disorder (PTSD), obsessive-compulsive disorder (OCD), panic disorder, social phobia, agoraphobia, or other more particular phobias. Eating disorders include, but are not limited to, anorexia, bulimia, and binge eating. Mood disorders include, but are not limited to, manic depression (bipolar disorder), major depression, and post-partum depression. Cognitive disorders include, for example, dementia, Attention Deficit Hyperactivity Disorder (ADHD), autism and Autism Spectrum Disorders (ASD), Down's Syndrome, traumatic brain injury (TBI), dyslexia, and the like. Personality disorders include, for example, borderline personality disorders. Psychotic disorders include but are not limited to schizophrenia and delusional disorders. Alcoholism and substance abuse-related disorders can include abuse and/or addiction to alcohol, nicotine, or other drugs (e.g., opiates, cannabinoids, inhalants, and psychostimulants such as cocaine, amphetamine, and methamphetamine). Additional conditions include medication-related hyperactivity or hyper-arousal conditions.

More particularly, diseases or conditions wherein inhibition of biological activity at, or signalling via, the RXFP3 receptor is desirable include, but are not limited to obesity, alcoholism, and other substance abuse and/or addiction-related disorders. In some embodiments, the obesity is related to antipsychotic drug-induced weight gain or hyperphagia associated with depression. For instance, the weight gain can be associated with the use of first- or second-generation antipsychotic drugs such as, but not limited to, amisulpride, asenapine, benperidol, chlorpromazine, clozapine, flupentixol, haloperidol, iloperidone, loxapine, olanzapine, paliperidone, risperidone, perphenazine, pimozide, pipothiazine, promazine, quetiapine, sertindole, sulpiride, trifluoperazine, and zuclopenthioxol.

By way of further example, the presently disclosed RXFP3 antagonists can find application in the treatment of substance use, abuse and/or addiction (including drug, alcohol, and nicotine addiction), addictive behavior and symptoms and conditions associated with substance abuse and addiction, as exemplified herein. One problem with alcoholism, as with substance addiction in general, is the chronically relapsing nature of the disorder. This behavior pattern can be effectively modelled in rodents, where numerous studies have demonstrated the ability of drug priming, psychological stress or the re-presentation of cues previously associated with drug availability to reinstate drug-seeking behavior following extinction, even in the absence of subsequent drug rewards.

Addiction to substances such as alcohol, opiates, cannabinoids, nicotine, and psychostimulants is typically associated with a number of adverse or negative behaviors exhibited by addicts, which behaviors can serve to exacerbate, prolong, or induce relapse into use or abuse of the substance, reinforce or exacerbate the addiction, or induce relapse into addiction and addictive behavior patterns. Other examples of negative behaviors associated with substance use or addiction include anxiety, dysphoria, stress reactivity, and cue reactivity.

In some embodiments, the presently disclosed subject matter provides a method for the prevention or inhibition of substance abuse and/or addiction, an addictive behavior, or of a symptom, behavior, or condition associated with substance abuse and/or addiction, the method comprising administering to a subject in need thereof an effective amount of a small molecule RXFP3 compound as disclosed herein or a pharmaceutically acceptable composition comprising such a compound. In some embodiments, the subject is a human.

In some embodiments, the behavior associated with substance abuse and/or addiction comprises substance use (i.e., self-administration) and/or substance seeking behavior. In some embodiments, the substance abuse and/or addiction comprises alcohol abuse and/or addition (i.e., alcoholism). In some embodiments, the substance abuse and/or addiction comprises nicotine abuse and/or addition. In some embodiments, the substance abuse and/or addiction comprises opiate abuse and/or addition.

An effective amount of the compounds disclosed herein comprise amounts sufficient to produce a noticible effect, such as, but not limited to, a reduction or cessation of self-administration of alcohol or another substance of abuse, weight loss, lack of weight gain, etc.). Actual dosage levels of active ingredients in a therapeutic compound of the presently disclosed subject matter can be varied so as to administer an amount of the active compound that is effective to achieve the desired therapeutic response for a particular subject and/or application. Preferably, a minimal dose is administered, and the dose is escalated in the absence of dose-limiting toxicity to a minimally effective amount. Determination and adjustment of a therapeutically effective dose, as well as evaluation of when and how to make such adjustments, are known to those of ordinary skill in the art.

VI. Methods of Preparing Small Molecule Antagonists for the Relaxin-3/RXFP3 System The presently disclosed antagonists can be prepared using standard synthetic methodology known in the art. For example, the compounds can be made by the methods described herein below or variations thereof that will be apparent to persons skilled in the art based on the present disclosure. As necessary, protecting groups known in the art can be utilized during the synthesis of the compounds.

In some embodiments, the antagonists are prepared by contacting a substituted analine or aminopyridine with the acid chloride of a N-substituted lactam (i.e., a N-substituted pyrrolidone or a N-substituted piperidinone) to form an amide. However, other approaches to the preparation of the amide bond can also be used. For example, in some embodiments, the acid chloride can be substituted by a carboxylic acid, an anhydride, or an activated ester (e.g., a N-hydroxysuccinimidyl (NHS) ester, an ester of hydroxybenzotriazole (HOBt), an ester of a nitrophenol, or an ester of a pentafluorophenol). Coupling agents, such as carbodiimides, typically used in the art of organic synthesis and/or peptide synthesis can also be used.

Scheme 1.

General Synthesis of Aniline Intermediates for Preparation of RXFP3 Antagonists.

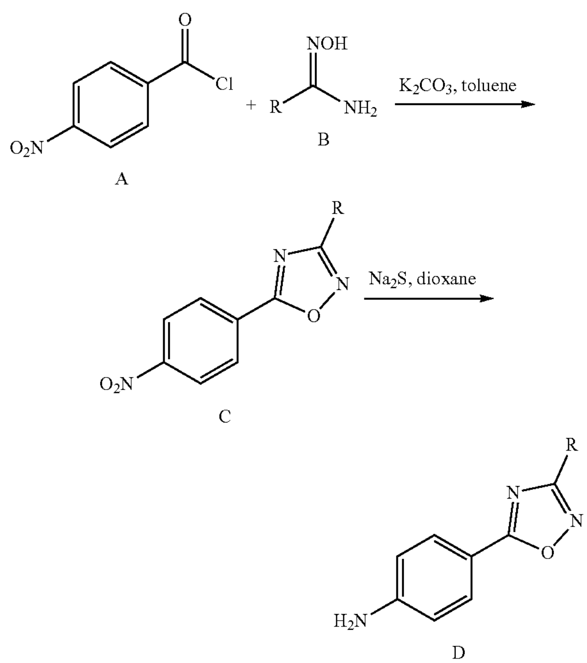

In some embodiments, the synthesis of the antagonists comprises the synthesis of a suitable substituted aniline or aminopyridine. For example, 4-(3-substituted 1,2,4-oxadiazol-5-yl)aniline intermediates for use in the synthesis of the presently disclosed antagonists were prepared as shown in Scheme 1, above. See Conole et al., Bioorg. Med. Chem. 2014, 22, 2220. More particularly, coupling of 4-nitrobenzoyl chloride (A) with an appropriate N-hydroxyl imidamide B using potassium carbonate ($K_2CO_3$) in refluxing toluene afforded 1,2,4-oxadiazole C. Reduction of the nitro group with sodium sulfide ($Na_2S$) provided 4-(3-substituted 1,2,4-oxadiazol-5-yl)aniline D.

Scheme 2.

General Synthesis Route to RLX-1-33 and RLX-35.

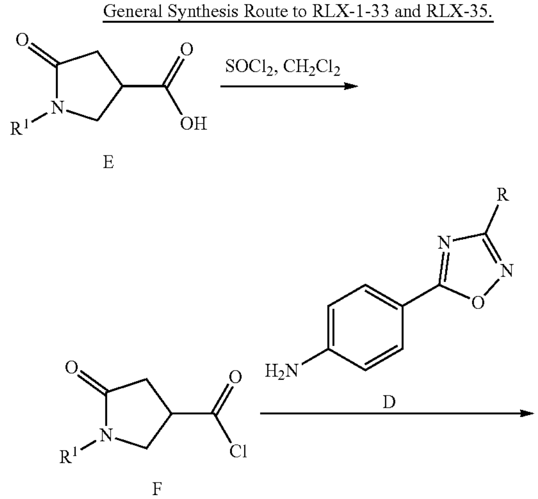

-continued

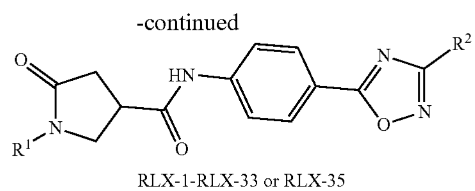

RLX-1-RLX-33 or RLX-35

Pyrrolidone-containing acid chloride intermediates and pyrrolidone-containing antagonist compounds, such as RLX-1-33 and RLX-35, were synthesized in accordance with the route shown in Scheme 2, above. More particularly, reaction of 5-oxo-1-substituted pyrrolidine-3-carboxylic acid E with thionyl chloride ($SOCl_2$) in dichloromethane ($CH_2Cl_2$) afforded acid chloride F. Condensation of F with aniline D from Scheme 1 provided the target compounds. Additional details regarding the synthesis of several exemplary pyrrolidone-containing antagonists of the presently disclosed subject matter, RLX compounds 1-33 and RLX-35 are described below in Example 1.

Scheme 3.
Synthesis of RLX-34.

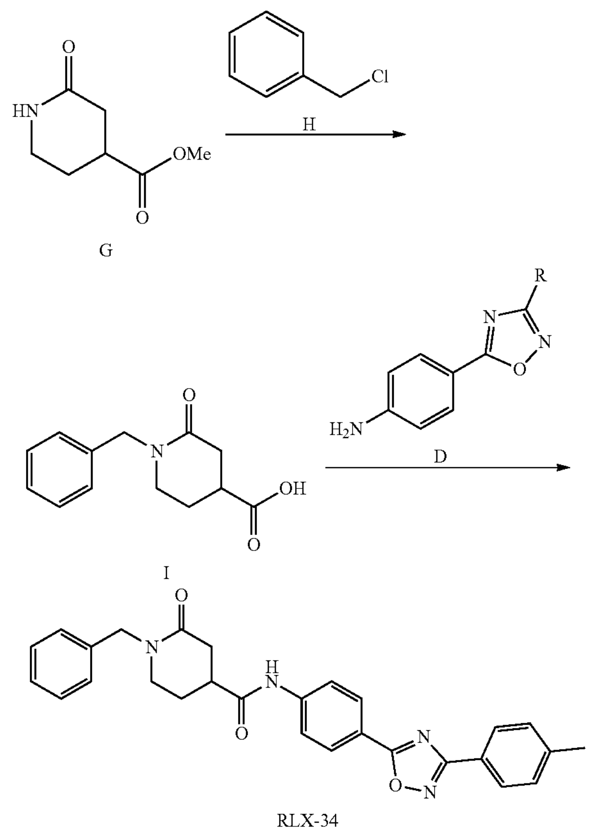

G

I

RLX-34

Piperidinone-containing antagonists, such as exemplary piperidinone-containing antagonist RLX-34, can be synthesized as shown in Scheme 3, above. As shown in Scheme 3, reaction of methyl 2-oxopiperidine-4-carboxylate (G) with benzyl chloride (H) using potassium hydroxide in dimethyl sulfoxide (DMSO) afforded carboxylic acid I after acidic workup. Converting the carboxylic acid I to the acid chloride (e.g., using thionyl chloride) followed by coupling with aniline D from Scheme 1 above comprising a 4-methylphenyl group as R provided the target compound, RLX-34. Additional piperidinone-containing antagonists can be prepared by the same route using anilines with other R groups or using various substituted benzyl chlorides or other halides in place of I. Additional details regarding the synthesis of RLX-34 are described below in Example 1.

Scheme 4.
Synthesis of RLX-36.

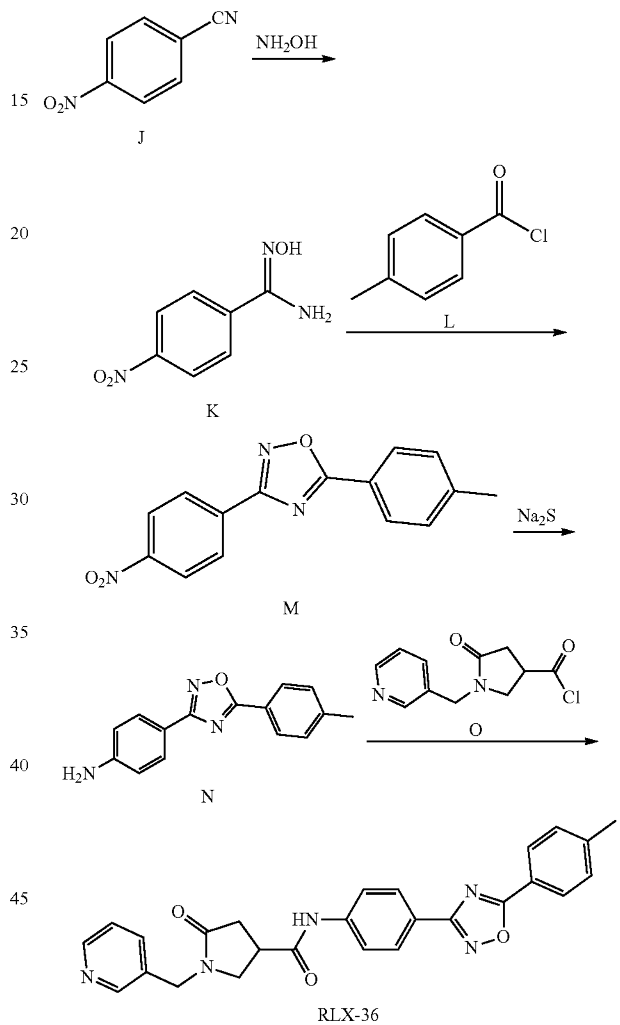

J

K

M

N

RLX-36

Compounds having a different orientation of the oxadiazole, such as RLX-36, can be prepared according to the synthetic route shown in Scheme 4, above. As shown in Scheme 4, reaction of 4-nitrophenylacetonitrile (J) with hydroxylamine hydrochloride afforded N-hydroxyl imidamide K. Condensation of imidamide K with 4-methylbenzoyl chloride (L) followed by reduction of the nitro group of the resulting oxadiazole (M) provided aniline N. See Conole et al., Bioorg. Med. Chem. 2014, 22, 2220. Coupling of aniline N with acid chloride O yielded the target compound, RLX-36. Additional compounds can be prepared by using benzoyl chlorides with other substituents other than methyl in place of L and/or by using acid chlorides with different nitrogen substituents (other than —$CH_2$-pyridinyl) in place of O.

Scheme 5.
Synthesis of RLX-37-39.

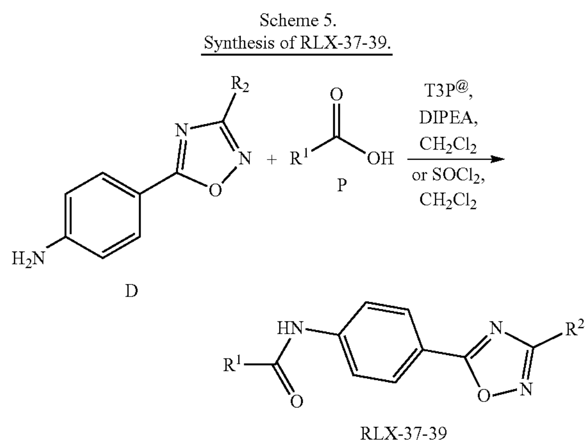

D

P

RLX-37-39

Benzylpyrrolidine-containing antagonist compounds, such as RLX-37, and benzylamine-containing antagonist compounds, such as RLX-38 and RLX-39, can be synthesized in accordance with the route shown in Scheme 5, above. Aniline D comprising a 4-methylphenyl group as $R^2$ was coupled with an appropriate acid P using standard amide coupling reagents, such as propylphosphonic anhydride ($T3P^{@}$) and N,N-diisopropylethylamine (DIPEA) or by forming an acid chloride (e.g., using thionyl chloride) to provide the target compounds, RLX-37-39. Additional details regarding the synthesis of RLX compounds 37-39 are described below in Example 1.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Example 1

Synthesis of RXFP3 Antagonists

All solvents and chemicals were reagent grade. Unless otherwise mentioned, all reagents and solvents were purchased from commercial vendors and used as received. Flash column chromatography was carried out on a Teledyne ISCO CombiFlash Rf system (Teledyne ISCO Inc., Lincoln, Nebraska, United States of America) using prepacked columns. Solvents used include hexane, ethyl acetate (EtOAc), dichloromethane, and methanol. Purity and characterization of compounds were established by a combination of nuclear magnetic resonance (NMR) spectrometery, mass spectrometry, thin layer chromatograph (TLC), and high-performance liquid chromatograph (HPLC) analyses. $^1H$ and $^{13}C$ NMR spectra were recorded on a Bruker Avance DPX-300 (300 MHz) spectrometer (Bruker Corporation. Billerica. Massachusetts. United States of America) and were determined in $CDCl_3$. DMSO-$d_6$, or $CD_3OD$ with tetramethylsilane (TMS) (0.00 parts-per-million (ppm)) or solvent peaks as the internal reference. Chemical shifts are reported in ppm relative to the reference signal and coupling constant (J) values are reported in hertz (Hz). Nominal mass spectra were obtained using an Agilent InfinityLab MSD single quadrupole mass spectrometer system (ESI) (Agilent Technologies. Santa Clara, California, United States of America). High resolution mass spectra (HRMS) were obtained using Agilent 1290 Infinity UHPLC-6230 time-of-flight (TOF) mass spectrometer (ESI) (Agilent Technologies, Santa Clara, California. United States of America). Thin layer chromatography (TLC) was performed on EMD precoated silica gel 60 F254 plates (MilliporeSigma, Merck KGH, Darmstadt, Germany), and spots were visualized with ultraviolet (UV) light or iodine staining. All final compounds were greater than 95% pure as determined by HPLC on a Waters 2695 Separation Module equipped with a Waters 2996 Photodiode Array Detector (Waters Corporation, Milford. Massachusetts. United States of America) and a Phenomenex SYNGERGI™ 4 mm Hydro-RP 80A C18 250×4.6 mm column (Phenomenex, Torrence, California. United States of Amercia) using a flow rate of 1 milliliter per minute (mL/min) starting with 1 min at 5% solvent B, followed by a 15 min gradient of 5-95% solvent B, followed by 9 min at 95% solvent B (solvent A, water with 0.1% trifluoroacetic acid (TFA); solvent B, acetonitrile with 0.1% TFA and 5% water; absorbance monitored at 280 nm).

Synthesis of RLX 1-39

RLX-1

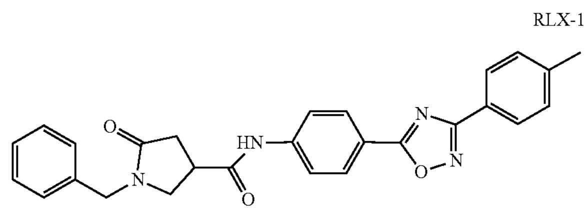 [SMILES: Cc1ccc(-c2noc(-c3ccc(NC(=O)C4CC(=O)N(Cc5ccccc5)C4)cc3)n2)cc1]

1-Benzyl-N-{4-[3-(4-methylphenyl)-1,2,4-oxadiazol-5-yl]phenyl}-5-oxopyrrolidine-3-carboxamide (RLX-1). To a stirred solution of 1-benzyl-5-oxopyrrolidine-3-carboxylic acid (110 mg, 0.5 mmol) in $CH_2Cl_2$ (5 mL) under nitrogen at room temperature was added $SOCl_2$ (0.36 mL, 50 mmol). The reaction mixture was stirred at 40° C. overnight, then concentrated under reduced pressure. The resulting acid chloride was dissolved in $CH_2Cl_2$ (5 mL), followed by addition of 4-[3-(4-methylphenyl)-1,2,4-oxadizaol-5-yl]aniline (126 mg, 0.5 mmol) and $Et_3N$ (0.14 mL, 1 mmol). After stirring at room temperature overnight, the reaction mixture was diluted with EtOAc (30 mL), washed with saturated $NaHCO_3$ (10 mL) and brine (10 mL). The organic layer was dried ($Na_2SO_4$) and concentrated. Flash column chromatography of the crude product on silica gel using 0-5% MeOH in $CH_2Cl_2$ gave the target compound RLX-1 (140 mg, 62% yield) as a white powder. $^1H$ NMR (300 MHz, $CDCl_3$) δ 8.87; (s, 1H), 8.10; (d, J=9.0 Hz, 2H), 8.02; (d, J=9.0 Hz, 2H), 7.74; (d, J=9.0 Hz, 2H), 7.40-7.20; (m, 7H), 4.53; (d, J=15.0 Hz, 1H), 4.42; (d, J=15.0 Hz, 1H), 3.75-3.60; (m, 1H), 3.50; (t, J=9.0 Hz, 1H), 3.35-3.20; (m, 1H), 2.90; (dd, J=18.0, 9.0 Hz, 1H), 2.72; (dd, J=18.0, 9.0 Hz, 1H), 2.41; (s, 3H); $^{13}C$ NMR (75 MHZ, $CDCl_3$) δ 174.99, 172.69, 170.80, 168.95, 141.89, 141.54, 135.56, 129.57, 129.26, 128.92, 127.94, 127.42, 124.10, 120.07, 119.75, 49.29, 46.76, 38.40, 35.02, 21.56; HRMS (ESI) m/z calcd for $C_{27}H_{24}N_4O_3$ $[M+H]^+$ 453.1921, m/z found 453.1939.

RLX-2

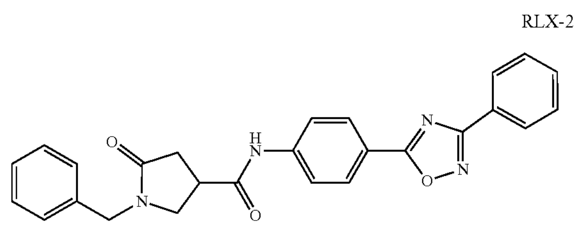 [SMILES: O=C(Nc1ccc(-c2nc(-c3ccccc3)no2)cc1)C1CC(=O)N(Cc2ccccc2)C1]

1-Benzyl-N-[4-(3-phenyl-1,2,4-oxadiazol-5-yl)phenyl]-5-oxopyrrolidine-3-carboxamide (RLX-2). The procedure for RLX-1 was followed using 1-benzyl-5-oxopyrrolidine-3-carboxylic acid and 4-(3-phenyl-1,2,4-oxadizaol-5-yl)aniline to give the target compound RLX-2 (42% yield) as an off-white powder. $^1$H NMR (300 MHZ, $CDCl_3$) δ 8.54; (s, 1H), 8.25-8.05; (m, 4H), 7.80-7.65; (m, 2H), 7.55-7.40; (m, 3H), 7.35-7.15; (m, 5H), 4.55; (d, J=13.5 Hz, 1H), 4.43; (d, J=13.5 Hz, 1H), 3.75-3.65; (m, 1H), 3.52; (t, J=9.0 Hz, 1H), 3.35-3.20; (m, 1H), 2.91; (dd, J=18.0, 9.0 Hz, 1H), 2.75; (dd, J=18.0, 9.0 Hz, 1H); $^{13}$C NMR (75 MHz, $CDCl_3$) δ 175.13, 172.50, 170.66, 168.96, 141.77, 135.60, 131.19, 129.32, 128.92, 128.85, 128.02, 127.95, 127.51, 126.96, 119.75, 49.18, 46.76, 38.56, 35.01; HRMS (ESI) m/z calcd for $C_{26}H_{22}N_4O_3$ $[M+H]^+$ 439.1765, m/z found 439.1786.

RLX-3

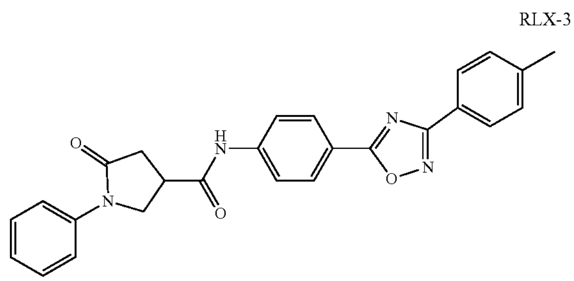 [SMILES: Cc1ccc(-c2noc(-c3ccc(NC(=O)C4CC(=O)N(c5ccccc5)C4)cc3)n2)cc1]

N-{4-[3-(4-Methylphenyl)-1,2,4-oxadiazol-5-yl]phenyl}-5-oxo-1-phenylpyrrolidine-3-carboxamide (RLX-3). The procedure for RLX-1 was followed using 5-oxo-1-phenylpyrrolidine-3-carboxylic acid and 4-[3-(4-methylphenyl)-1,2,4-oxadizaol-5-yl]aniline to give the target compound RLX-3 (49% yield) as a white powder. $^1$H NMR (300 MHz, DMSO-$d_6$) δ 10.64; (s, 1H), 8.15; (d, J=9.0 Hz, 2H), 7.97; (d, J=9.0 Hz, 2H). 7.90; (d, J=9.0 Hz, 2H), 7.68; (d, J=6.0 Hz, 2H), 7.45-7.33; (m, 4H), 7.15; (t, J=7.5 Hz, 1H), 4.19-3.98; (m, 2H), 3.59-3.45; (m, 1H), 2.94-2.72; (m, 2H), 2.39; (s, 3H); $^{13}$C NMR (75 MHz, DMSO-$d_6$) δ 174.91, 171.73, 171.66, 168.07, 143.27, 141.46, 139.11, 129.72, 128.95, 128.64, 126.95, 124.02, 123.45, 119.45, 119.38, 117.96, 50.43, 36.90, 35.68, 21.02; HRMS (ESI) m/z calcd for $C_{26}H_{22}N_4O_3$ $[M+H]^+$ 439.1765, m/z found 439.1785.

RLX-4

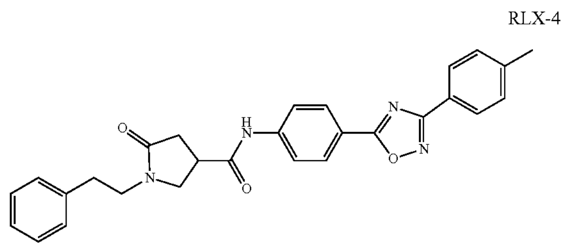 [SMILES: Cc1ccc(-c2noc(-c3ccc(NC(=O)C4CC(=O)N(CCc5ccccc5)C4)cc3)n2)cc1]

N-{4-[3-(4-Methylphenyl)-1,2,4-oxadiazol-5-yl]phenyl}-5-oxo-1-(2-phenylethyl)pyrrolidine-3-carboxamide (RLX-4). The procedure for RLX-1 was followed using 5-oxo-1-(2-phenylethyl)pyrrolidine-3-carboxylic acid and 4-[3-(4-methylphenyl)-1,2,4-oxadizaol-5-yl]aniline to give the target compound RLX-4 (43% yield) as a white powder. $^1$H NMR (300 MHz, $CDCl_3$) δ 9.54; (s, 1H), 8.13; (d, J=7.5 Hz, 2H), 8.02; (d, J=7.5 Hz, 2H), 7.78; (d, J=9.0 Hz, 2H), 7.40-7.20; (m, 7H), 3.74; (dd, J=10.5, 7.5 Hz, 1H), 3.56; (t, J=7.5 Hz, 2H), 3.46; (t, J=9.0 Hz, 1H), 3.33-3.18; (m, 1H). 2.87; (t, J=7.5 Hz, 2H), 2.80-2.60; (m, 2H), 2.42; (s, 3H); $^{13}$C NMR (75 MHz, $CDCl_3$) δ 175.15, 172.89, 170.94, 168.90, 142.29, 141.56, 138.35, 129.56, 129.20, 128.60, 127.39, 126.60, 124.02, 119.69, 119.64, 49.80, 44.18, 38.25, 35.00, 33.60, 21.50; HRMS (ESI) m/z calcd for $C_{28}H_{26}N_4O_3$ $[M+H]^+$ 467.2078, m/z found 467.2092.

RLX-5

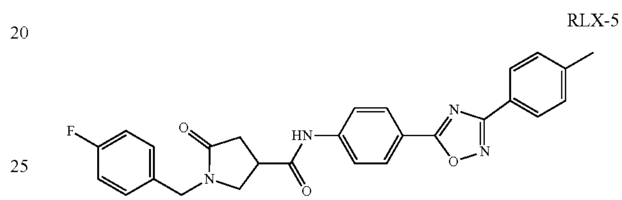

1-[(4-Fluorophenyl)methyl]-N-{4-[3-(4-methylphenyl)-1,2,4-oxadiazol-5-yl]phenyl}-5-oxopyrrolidine-3-carboxamide (RLX-5). The procedure for RLX-1 was followed using 1-[(4-fluorophenyl)methyl]-5-oxopyrrolidine-3-carboxylic acid and 4-[3-(4-methylphenyl)-1,2,4-oxadizaol-5-yl]aniline to give the target compound RLX-5 (49% yield) as a white powder. $^1$H NMR (300 MHz, $CDCl_3$) δ 8.06; (d, J=9.0 Hz, 2H), 7.95; (d, J=9.0 Hz, 2H), 7.88; (d, J=9.0 Hz, 2H), 7.23; (d, J=9.0 Hz, 2H), 7.18-7.12; (m, 2H), 6.95; (t, J=9.0 Hz, 2H), 4.32; (d, J=15.0 Hz, 1H), 4.32; (d, J=15.0 Hz, 1H), 3.59; (dd, J=10.5, 7.5 Hz, 1H), 3.38; (t, J=9.0 Hz, 1H), 3.28-3.15; (m, 1H), 2.82-2.62; (m, 2H), 2.34; (s, 3H); $^{13}$C NMR (75 MHz, $CDCl_3$) δ 174.14, 171.98, 169.95, 167.94, 161.44; (d, $J_{C-F}$=245.3 Hz), 141.19, 140.63, 130.51, 128.83 (d, $J_{C-F}$=7.5 Hz), 128.60, 128.25, 126.43, 123.05, 118.79; (d, $J_{C-F}$=4.5 Hz), 118.68, 114.77; (d, $J_{C-F}$=21.8 Hz), 48.00, 45.01, 37.10, 33.96, 20.55; HRMS (ESI) m/z calcd for $C_{27}H_{23}FN_4O_3$ $[M+H]^+$ 471.1827, m/z found 471.1846.

RLX-6

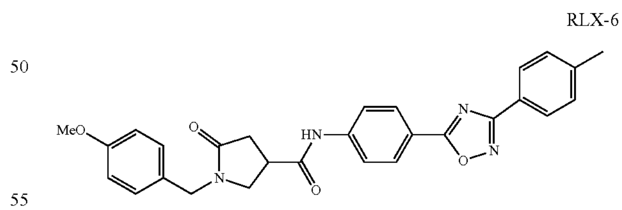

1-[(4-Methoxyphenyl)methyl]-N-{4-[3-(4-methylphenyl)-1,2,4-oxadiazol-5-yl]phenyl}-5-oxopyrrolidine-3-carboxamide (RLX-6). The procedure for RLX-1 was followed using 1-[(4-methoxyphenyl)methyl]-5-oxopyrrolidine-3-carboxylic acid and 4-[3-(4-methylphenyl)-1,2,4-oxadizaol-5-yl]aniline to give the target compound RLX-6 (60% yield) as a white powder. H NMR (300 MHz, DMSO-$d_6$) δ 10.5; (s, 1H), 8.14; (d, J=9.0 Hz, 2H), 7.98; (d, J=9.0 Hz, 2H), 7.86; (d, J=9.0 Hz, 2H), 7.41; (d, J=9.0 Hz, 2H), 7.19; (d, J=9.0 Hz, 2H), 6.92; (t, J=9.0 Hz, 2H), 4.34; (s, 2H), 3.74; (s, 3H), 3.55-3.45; (m, 1H), 3.42-3.32; (m, 2H), 2.65-2.57;

(m, 2H), 2.40; (s, 3H); $^{13}C$ NMR (75 MHz, DMSO-$d_6$) δ 174.95, 171.87, 171.84, 168.11, 158.55, 143.32, 141.52, 129.77, 129.05, 128.97, 128.56, 127.00, 123.47, 119.41, 117.91, 113.97, 55.05, 48.66, 44.74, 37.12, 33.85, 21.07; HRMS (ESI) m/z calcd for $C_{28}H_{26}N_4O_4$ [M+H]$^+$ 483.2027, m/z found 483.2018.

RLX-7

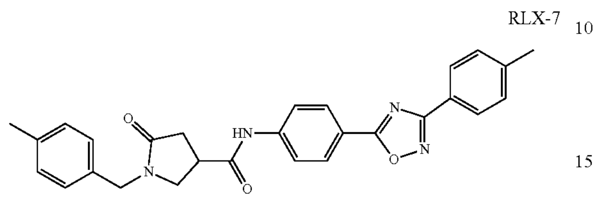

1-[(4-Methylphenyl)methyl]-N-{4-[3-(4-methylphenyl)-1,2,4-oxadiazol-5-yl]phenyl}-5-oxopyrrolidine-3-carboxamide (RLX-7). The procedure for RLX-1 was followed using 1-[(4-methylphenyl)methyl]-5-oxopyrrolidine-3-carboxylic acid and 4-[3-(4-methylphenyl)-1,2,4-oxadizaol-5-yl]aniline to give the target compound RLX-7 (45% yield) as a white powder. $^1H$ NMR (300 MHz, $CDCl_3$) δ 9.53; (s, 1H), 8.14; (d, J=9.0 Hz, 2H), 8.03; (d, J=9.0 Hz, 2H), 7.76; (d, J=9.0 Hz, 2H), 7.31; (d, J=9.0 Hz, 2H), 7.14; (s, 4H), 4.51; (d, J=15.0 Hz, 1H), 4.38; (d, J=15.0 Hz, 1H), 3.66; (dd, J=9.0, 6.0 Hz, 1H), 3.46; (t, J=9.0 Hz, 1H), 3.35-3.22; (m, 1H), 2.90-2.68; (m, 2H), 2.42; (s, 3H), 2.33; (s, 3H); $^{13}C$ NMR (75 MHZ, $CDCl_3$) δ 175.16, 172.93, 171.00, 168.88, 141.55, 137.60, 132.52, 129.55, 129.47, 129.17, 128.06, 127.38, 124.01, 119.63, 48.95, 46.42, 38.09, 34.95, 21.48, 21.01; HRMS (ESI) m/z calcd for $C_{28}H_{26}N_4O_3$ [M+H]$^+$ 467.2078, m/z found 467.2099.

RLX-8

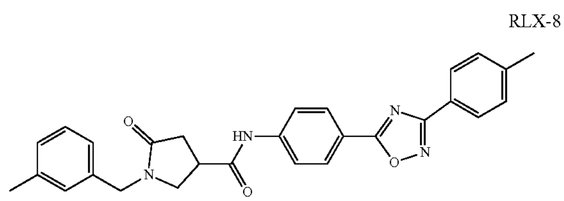

1-[(3-Methylphenyl)methyl]-N-{4-[3-(4-methylphenyl)-1,2,4-oxadiazol-5-yl]phenyl}-5-oxopyrrolidine-3-carboxamide (RLX-8). The procedure for RLX-1 was followed using 1-[(3-methylphenyl)methyl]-5-oxopyrrolidine-3-carboxylic acid and 4-[3-(4-methylphenyl)-1,2,4-oxadizaol-5-yl]aniline to give the target compound RLX-8 (46% yield) as a white powder. $^1H$ NMR (300 MHz, $CDCl_3$) δ 8.75; (s, 1H), 8.12; (d, J=9.0 Hz, 2H), 8.03; (d, J=9.0 Hz, 2H), 7.73; (d, J=9.0 Hz, 2H), 7.29; (d, J=9.0 Hz, 2H), 7.23-7.16; (m, 1H), 7.12-6.98; (m, 3H), 4.49; (d, J=15.0 Hz, 1H), 4.39; (d, J=15.0 Hz, 1H), 3.66; (dd, J=9.0, 6.0 Hz, 1H), 3.51; (t, J=9.0 Hz, 1H), 3.36-3.24; (m, 1H), 2.95-2.85; (m, 1H), 2.78-2.66; (m, 1H), 2.42; (s, 3H), 2.31; (s, 3H); $^{13}C$ NMR (75 MHz, $CDCl_3$) δ 174.99, 172.55, 170.78, 168.95, 141.87, 141.52, 138.67, 135.53, 129.56, 129.26, 128.77, 128.68, 127.43, 125.01, 124.13, 120.08, 119.73, 49.24, 46.72, 38.48, 35.02, 21.56, 21.36; HRMS (ESI) m/z calcd for $C_{28}H_{26}N_4O_3$ [M+H]$^+$ 467.2078, m/z found 467.2095.

RLX-9

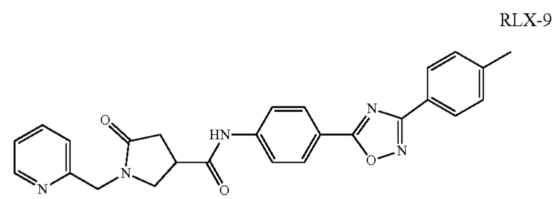 [SMILES: Cc1ccc(-c2noc(-c3ccc(NC(=O)C4CC(=O)N(Cc5ccccn5)C4)cc3)n2)cc1]

N-{4-[3-(4-Methylphenyl)-1,2,4-oxadiazol-5-yl]phenyl}-5-oxo-1-[(pyridin-2-yl)methyl]-pyrrolidine-3-carboxamide (RLX-9). The procedure for RLX-1 was followed using 5-oxo-1-[(pyridin-2-yl)methyl]pyrrolidine-3-carboxylic acid and 4-[3-(4-methylphenyl)-1,2,4-oxadizaol-5-yl] aniline to give the target compound RLX-9 (64% yield) as a white powder. $^1H$ NMR (300 MHZ, $CDCl_3$) δ 9.83; (s, 1H), 8.51-8.46; (m, 1H), 8.13; (d, J=9.0 Hz, 2H), 8.03; (d, J=9.0 Hz, 2H), 7.80-7.68; (m, 3H), 7.35-7.20; (m, 4H), 4.77; (d, J=16.5 Hz, 1H), 4.53; (d, J=16.5 Hz, 1H), 3.76; (dd, J=9.0, 6.0 Hz, 1H), 3.66; (t, J=9.0 Hz, 1H), 3.48-3.35; (m, 1H), 2.94-2.75; (m, 2H), 2.42; (s, 3H); $^{13}C$ NMR (75 MHz, $CDCl_3$) δ 175.12, 173.48, 171.32, 168.88, 155.53, 149.09, 142.32, 141.52, 137.59, 129.54, 129.14, 127.38, 124.04, 122.92, 122.58, 119.94, 119.75, 49.71, 47.78, 38.50, 34.83, 21.51; HRMS (ESI) m/z calcd for $C_{26}H_{23}N_5O_3$ [M+H]$^+$ 454.1874, m/z found 454.1893.

RLX-10

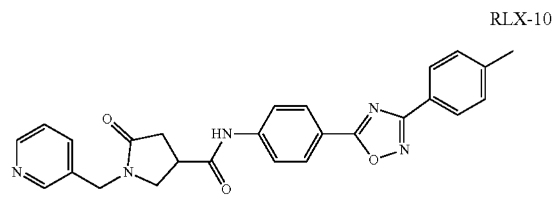 [SMILES: Cc1ccc(-c2noc(-c3ccc(NC(=O)C4CC(=O)N(Cc5cccnc5)C4)cc3)n2)cc1]

N-{4-[3-(4-Methylphenyl)-1,2,4-oxadiazol-5-yl]phenyl}-5-oxo-1-[(pyridin-3-yl)methyl]-pyrrolidine-3-carboxamide (RLX-10). The procedure for RLX-1 was followed using 5-oxo-1-[(pyridin-3-yl)methyl]pyrrolidine-3-carboxylic acid and 4-[3-(4-methylphenyl)-1,2,4-oxadizaol-5-yl] aniline to give the target compound RLX-10 (66% yield) as a white powder. $^1H$ NMR (300 MHz, $CDCl_3$) δ 9.21; (s, 1H), 8.61-8.54; (m, 2H), 8.12; (d, J=9.0 Hz, 2H), 8.02; (d, J=9.0 Hz, 2H), 7.80-7.66; (m, 3H), 7.40-7.25; (m, 3H), 4.64; (d, J=15.0 Hz, 1H), 4.43; (d, J=15.0 Hz, 1H), 3.71; (dd, J=9.0, 6.0 Hz, 1H), 3.52; (t, J=9.0 Hz, 1H), 3.40-3.28; (m, 1H), 2.90; (dd, J=18.0, 6.0 Hz, 1H), 2.71; (dd, J=16.5, 10.5 Hz, 1H), 2.42; (s, 3H); $^{13}C$ NMR (75 MHz, $CDCl_3$) δ 174.96, 172.76, 170.59, 168.98, 148.74, 148.68, 141.92, 141.55, 136.69, 132.23, 129.57, 129.30, 127.45, 124.25, 124.13, 120.20, 119.77, 49.16, 44.18, 38.47, 34.82, 21.58; HRMS (ESI) m/z calcd for $C_{26}H_{23}N_5O_3$ [M+H]$^+$ 454.1874, m/z found 454.1889.

RLX-11

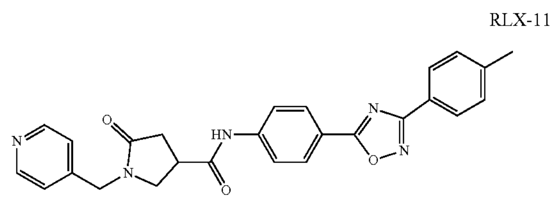

N-{4-[3-(4-Methylphenyl)-1,2,4-oxadiazol-5-yl]phenyl}-5-oxo-1-[(pyridin-4-yl)methyl]-pyrrolidine-3-carboxamide (RLX-11). The procedure for RLX-1 was followed using 5-oxo-1-[(pyridin-4-yl)methyl]pyrrolidine-3-carboxylic acid and 4-[3-(4-methylphenyl)-1,2,4-oxadizaol-5-yl]aniline to give the target compound RLX-11 (71% yield) as a white powder. $^1$H NMR (300 MHz, DMSO-$d_6$) δ 10.82; (s, 1H), 8.65-8.55; (m, 2H), 8.15; (d, J=9.0 Hz, 2H), 7.78; (d, J=6.0 Hz, 2H), 7.89; (d, J=9.0 Hz, 2H), 7.45-7.35; (m, 4H), 4.54; (d, J=18.0 Hz, 1H), 4.47; (d, J=18.0 Hz, 1H), 3.66-3.56; (m, 1H). 3.52-3.42; (m, 2H), 2.80-2.57; (m, 2H), 2.02; (s, 3H); $^{13}$C NMR (75 MHz, DMSO-$d_6$) δ 174.92, 172.58, 172.03, 168.08, 148.49, 147.71, 143.30, 141.48, 129.73, 128.95, 126.96, 123.44, 122.73, 119.41, 117.90, 49.13, 44.43, 37.14, 33.64, 21.03; HRMS (ESI) m/z calcd for $C_{26}H_{23}N_5O_3$ [M+H]$^+$ 454.1874, m/z found 454.1895.

RLX-12

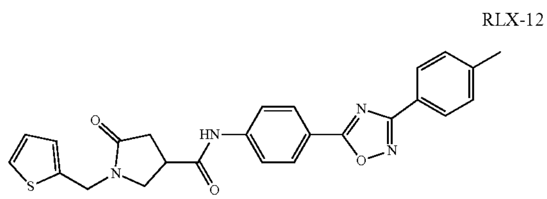 [SMILES: Cc1ccc(-c2noc(-c3ccc(NC(=O)C4CC(=O)N(Cc5cccs5)C4)cc3)n2)cc1]

N-{4-[3-(4-Methylphenyl)-1,2,4-oxadiazol-5-yl]phenyl}-5-oxo-1-[(thiophen-2-yl)methyl]-pyrrolidine-3-carboxamide (RLX-12). The procedure for RLX-1 was followed using 5-oxo-1-[(thiophen-2-yl)methyl]pyrrolidine-3-carboxylic acid and 4-[3-(4-methylphenyl)-1,2,4-oxadizaol-5-yl]aniline to give the target compound RLX-12 (55% yield) as an off-white powder. $^1$H NMR (300 MHz, $CDCl_3$) δ 9.10; (s, 1H), 8.03; (d, J=9.0 Hz, 2H), 7.93; (d, J=9.0 Hz, 2H), 7.69; (d, J=9.0 Hz, 2H), 7.20; (d, J=9.0 Hz, 2H), 7.13; (dd, J=6.0, 3.0 Hz, 1H), 6.90-6.82; (m, 2H), 4.63; (d, J=16.5 Hz, 1H), 4.47; (d, J=16.5 Hz, 1H), 3.66; (dd, J=9.0, 6.0 Hz, 1H), 3.53; (t, J=9.0 Hz, 1H), 3.35-3.20; (m, 1H), 2.79; (dd, J=16.5, 7.5 Hz, 1H), 2.61; (dd, J=16.5, 10.5 Hz, 1H), 2.33 (s, 3H); $^{13}$C NMR (75 MHZ, $CDCl_3$) δ 174.98, 172.52, 170.74, 168.91, 142.00, 141.50, 137.83, 129.52, 129.20, 127.37, 127.09, 127.01, 125.80, 124.04, 119.95, 119.73, 49.10, 41.21, 38.27, 34.97, 21.51; HRMS (ESI) m/z calcd for $C_{25}H_{22}N_4O_3S$ [M+H]$^+$ 459.1485, m/z found 459.1504.

RLX-13

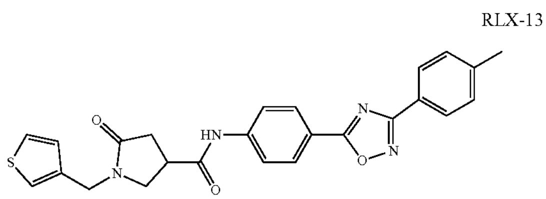 [SMILES: Cc1ccc(-c2noc(-c3ccc(NC(=O)C4CC(=O)N(Cc5ccsc5)C4)cc3)n2)cc1]

N-{4-[3-(4-Methylphenyl)-1,2,4-oxadiazol-5-yl]phenyl}-5-oxo-1-[(thiophen-3-yl)methyl]-pyrrolidine-3-carboxamide (RLX-13). The procedure for RLX-1 was followed using 5-oxo-1-[(thiophen-3-yl)methyl]pyrrolidine-3-carboxylic acid and 4-[3-(4-methylphenyl)-1,2,4-oxadizaol-5-yl]aniline to give the target compound RLX-13; (55% yield) as an off-white powder. $^1$H NMR (300 MHz, $CDCl_3$) δ 9.18; (s, 1H), 8.10; (d, J=9.0 Hz, 2H), 8.01; (d, J=9.0 Hz, 2H), 7.75; (d, J=9.0 Hz, 2H), 7.30-7.24; (m, 3H). 7.16-7.12; (m, 1H), 6.97-6.92; (m, 1H), 4.49; (d, J=16.5 Hz, 1H), 4.44; (d, J=16.5 Hz, 1H), 3.68; (dd, J=12.0, 6.0 Hz, 1H), 3.54; (t, J=9.0 Hz, 1H), 3.38-3.22; (m, 1H), 2.86; (dd, J=16.5, 7.5 Hz, 1H), 2.70; (dd, J=16.5, 9.0 Hz, 1H). 2.40; (s, 3H); $^{13}$C NMR (75 MHz, $CDCl_3$) δ 174.95, 172.64, 171.01, 168.90, 142.00, 141.51, 136.24, 129.52, 129.18, 127.35, 127.10, 126.86, 124.01, 123.01, 119.92, 119.72, 49.42, 41.74, 38.09, 34.97, 21.50; HRMS (ESI) m/z calcd for $C_{25}H_{22}N_4O_3S$ [M+H]$^+$ 459.1485, m/z found 459.1501.

RLX-14

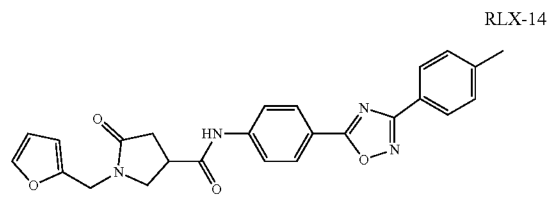 [SMILES: Cc1ccc(-c2noc(-c3ccc(NC(=O)C4CC(=O)N(Cc5ccco5)C4)cc3)n2)cc1]

1-[(Furan-2-yl)methyl]-N-{4-[3-(4-methylphenyl)-1,2,4-oxadiazol-5-yl]phenyl}-5-oxopyrrolidine-3-carboxamide (RLX-14). The procedure for RLX-1 was followed using 1-[(furan-2-yl)methyl]-5-oxopyrrolidine-3-carboxylic acid and 4-[3-(4-methylphenyl)-1,2,4-oxadizaol-5-yl]aniline to give the target compound RLX-14 (61% yield) as a pale yellow powder. $^1$H NMR (300 MHz, $CDCl_3$) δ 8.18; (d, J=9.0 Hz, 2H), 8.08; (s, 1H), 8.05; (d, J=9.0 Hz, 2H), 7.75; (d, J=9.0 Hz, 2H), 7.38-7.28; (m, 3H), 6.35-6.27; (m, 2H), 4.58; (d, J=15.0 Hz, 1H), 4.44; (d, J=15.0 Hz, 1H), 3.75; (dd, J=9.0, 6.0 Hz, 1H), 3.63; (t, J=9.0 Hz, 1H), 3.35-3.22; (m, 1H), 2.88; (dd, J=18.0, 9.0 Hz, 1H), 2.74; (dd, J=16.5, 10.5 Hz, 1H), 2.43; (s, 3H); $^{13}$C NMR (75 MHz, $CDCl_3$) δ 174.97, 172.39, 170.64, 168.95, 149.18, 142.77, 141.81, 141.52, 129.55, 129.27, 127.41, 124.09, 120.14, 119.73, 110.53, 108.87, 49.30, 39.38, 38.50, 34.93, 21.55; HRMS (ESI) m/z calcd for $C_{25}H_{22}N_4O_4$ [M+H]$^+$ 443.1714, m/z found 443.1727.

RLX-15

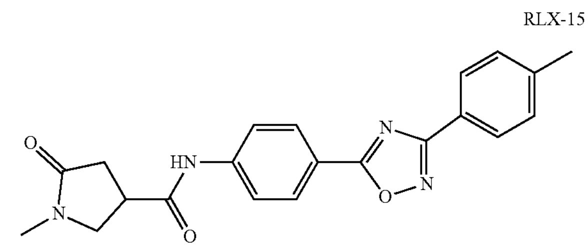

1-Methyl-N-{4-[3-(4-methylphenyl)-1,2,4-oxadiazol-5-yl]phenyl}-5-oxopyrrolidine-3-carboxamide (RLX-15). The procedure for RLX-1 was followed using 1-methyl-5-oxopyrrolidine-3-carboxylic acid and 4-[3-(4-methylphenyl)-1,2,4-oxadizaol-5-yl]aniline to give the target compound RLX-15 (46% yield) as a white powder. $^1$H NMR (300 MHz, DMSO-$d_6$) δ 10.56; (s, 1H), 8.15; (d, J=9.0 Hz, 2H), 7.98; (d, J=9.0 Hz, 2H), 7.89; (d, J=9.0 Hz, 2H), 7.41; (d, J=9.0 Hz, 2H), 3.63; (t, J=9.0 Hz, 1H), 3.55-3.47; (m, 1H), 3.44-3.33; (m, 1H), 2.75; (s, 3H), 2.60-2.50; (m, 2H), 2.40; (s, 3H); $^{13}$C NMR (75 MHz, DMSO-$d_6$) δ 174.91, 172.03, 171.74, 168.06, 143.33, 141.45, 129.72, 128.93, 126.95, 123.45, 119.37, 117.87, 51.03, 37.00, 33.75, 28.84, 21.02; MS (ESI) m/z calcd for $C_{21}H_{20}N_4O_3$ [M+H]$^+$ 377.16, m/z found 377.20.

RLX-16

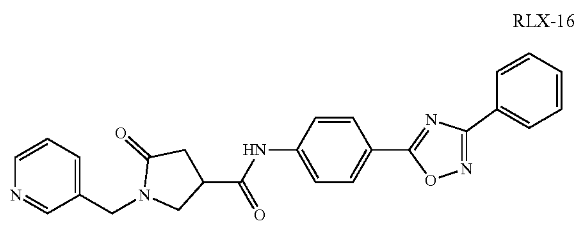 [SMILES: O=C(Nc1ccc(-c2nc(-c3ccccc3)no2)cc1)C1CC(=O)N(Cc2cccnc2)C1]

5-Oxo-N-[4-(3-phenyl-1,2,4-oxadiazol-5-yl)phenyl]-1-[(pyridin-3-yl)methyl]-pyrrolidine-3-carboxamide (RLX-16). The procedure for RLX-1 was followed using 5-oxo-1-[(pyridin-3-yl)methyl]pyrrolidine-3-carboxylic acid and 4-(3-phenyl-1,2,4-oxadizaol-5-yl)aniline to give the target compound RLX-16 (52% yield) as a pale brown powder. $^1$H NMR (300 MHz, DMSO-$d_6$) δ 10.56; (s, 1H), 8.53; (br s, 2H), 8.16; (d, J=9.0 Hz, 2H), 8.10-8.05; (m, 2H), 7.88; (d, J=9.0 Hz, 2H), 7.72; (d, J=9.0 Hz, 1H), 7.65-7.55; (m, 3H), 7.46-7.35; (m, 1H), 4.47; (s, 2H), 3.64-3.54; (m, 1H), 3.48-3.35; (m, 2H), 2.75-2.55; (m, 2H); $^{13}$C NMR (75 MHz, DMSO-$d_6$) δ 175.08, 172.27, 171.92, 168.11, 148.62, 148.25, 143.33, 135.70, 131.53, 129.19, 128.96, 127.02, 126.22, 119.39, 117.83, 48.82, 42.92, 37.12, 33.73; HRMS (ESI) m/z calcd for $C_{25}H_{21}N_5O_3$ [M+H]+440.1717, m/z found 440.1736.

RLX-17

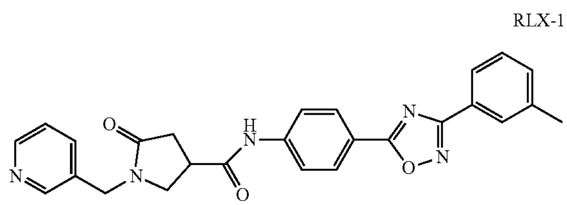

N-{4-[3-(3-Methylphenyl)-1,2,4-oxadiazol-5-yl]phenyl}-5-oxo-1-[(pyridin-3-yl)methyl]-pyrrolidine-3-carboxamide (RLX-17). The procedure for RLX-1 was followed using 5-oxo-1-[(pyridin-3-yl)methyl]pyrrolidine-3-carboxylic acid and 4-[3-(3-methylphenyl)-1,2,4-oxadizaol-5-yl] aniline to give the target compound RLX-17 (46% yield) as a pale brown powder. $^1$H NMR (300 MHz, $CDCl_3$) δ 9.63; (s, 1H), 8.58-8.52; (m, 2H), 8.10; (d, J=9.0 Hz, 2H), 7.95-7.88; (m, 2H), 7.76; (d, J=9.0 Hz, 2H), 7.68-7.63; (m, 1H), 7.40-7.27; (m, 3H), 4.59; (d, J=15.0 Hz, 1H), 4.43; (d, J=15.0 Hz, 1H), 3.70; (dd, J=9.0, 6.0 Hz, 1H), 3.51; (t, J=9.0 Hz, 1H), 3.42-3.28; (m, 1H), 2.88; (dd, J=16.5, 7.5 Hz, 1H), 2.69; (dd, J=16.5, 10.5 Hz, 1H), 2.41; (s, 3H); $^{13}$C NMR (75 MHZ, $CDCl_3$) δ 174.98, 172.88, 170.73, 168.96, 148.87, 148.77, 142.11, 138.58, 136.29, 131.94, 129.17, 128.69, 127.95, 126.67, 124.52, 124.10, 119.86, 119.68, 49.17, 44.10, 38.15, 34.76, 21.26; HRMS (ESI) m/z calcd for $C_{26}H_{23}N_5O_3$ $[M+H]^+$ 454.1874, m/z found 454.1896.

RLX-18

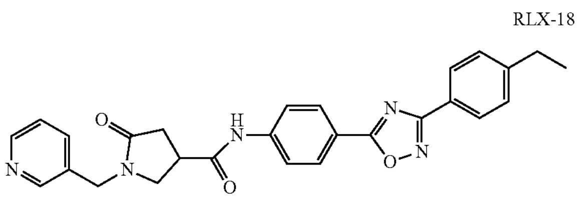 [SMILES: CCc1ccc(-c2noc(-c3ccc(NC(=O)C4CC(=O)N(Cc5cccnc5)C4)cc3)n2)cc1]

N-{4-[3-(4-Ethylphenyl)-1,2,4-oxadiazol-5-yl]phenyl}-5-oxo-1-[(pyridin-3-yl)methyl]-pyrrolidine-3-carboxamide (RLX-18). The procedure for RLX-1 was followed using 5-oxo-1-[(pyridin-3-yl)methyl]pyrrolidine-3-carboxylic acid and 4-[3-(4-ethylphenyl)-1,2,4-oxadizaol-5-yl]aniline to give the target compound RLX-18 (49% yield) as a pale brown powder. $^1$H NMR (300 MHz, DMSO-$d_6$) δ 10.57; (s, 1H), 8.65-8.45; (m, 2H), 8.15; (d, J=9.0 Hz, 2H), 8.00; (d, J=6.0 Hz, 2H), 7.87; (d, J=9.0 Hz, 2H), 7.74; (d, J=9.0 Hz, 1H), 7.45-7.28; (m, 3H), 4.47; (s, 2H), 3.64-3.53; (m, 1H), 4.48-3.35; (m, 2H), 2.75-2.55; (m, 4H), 1.23; (t, J=7.5 Hz, 3H); $^{13}$C NMR (75 MHZ, $CDCl_3$) δ 174.92, 172.29, 171.92, 168.08, 148.42, 148.07, 147.59, 143.28, 135.94, 132.62, 128.94, 128.55, 127.07, 123.81, 123.69, 119.39, 117.89, 48.83, 42.90, 37.12, 33.73, 28.06, 15.13; HRMS (ESI) m/z calcd for $C_{27}H_{25}N_5O_3$ $[M+H]^+$ 468.2030, m/z found 468.2050.

RLX-19

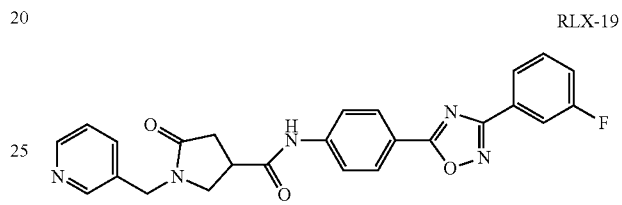

N-{4-[3-(3-Fluorophenyl)-1,2,4-oxadiazol-5-yl]phenyl}-5-oxo-1-(3-pyridinylmethyl) pyrrolidine-3-carboxamide (RLX-19). The procedure for RLX-1 was followed using 5-oxo-1-[(pyridin-3-yl)methyl]pyrrolidine-3-carboxylic acid and 4-[3-(3-fluorophenyl)-1,2,4-oxadizaol-5-yl]aniline to give the target compound RLX-19 (49% yield) as a white powder. $^1$H NMR (300 MHz, $CDCl_3$ with 20 μL $CD_3OD$) δ 9.91; (s, 1H), 8.52; (dd, J=4.9, 1.6 Hz, 1H), 8.48; (d, J=2.2 Hz, 1H), 8.15; (d, J=8.6 Hz, 2H), 7.95; (dt, J=7.8, 1.3 Hz, 1H), 7.85; (ddd, J=9.5, 2.7, 1.5 Hz, 1H), 7.79; (d, J=8.6 Hz, 2H), 7.71; (dt, J=8.0, 1.9 Hz, 1H), 7.49; (td, J=8.0, 5.7 Hz, 1H), 7.37; (dd, J=7.9, 4.9 Hz, 1H), 7.23; (tdd, J=8.4, 2.6, 1.1 Hz, 1H), 4.61; (d, J=15.1 Hz, 1H), 4.46; (d, J=15.1 Hz, 1H), 3.68; (dd, J=9.7, 6.6 Hz, 1H), 3.53; (t, J=9.2 Hz, 1H), 3.44-3.28; (m, 1H), 2.95-2.69; (m, 2H); $^{13}$C NMR (75 MHz, $CDCl_3$ with 20 μL $CD_3OD$) & 175.55, 173.41, 171.03, 167.97, 162.85; (d, $J_{C-F}$=246.7 Hz), 148.72, 148.68, 142.56, 136.47, 130.55; (d, $J_{C-F}$=8.1 Hz), 129.19, 128.93, 124.10, 123.13; (d, $J_{C-F}$=3.0 Hz), 119.72, 119.64, 119.30, 118.12; (d, $J_{C-F}$=21.2 Hz), 114.45; (d, $J_{C-F}$=23.7 Hz), 49.01, 44.01, 37.86, 34.61; MS (ESI) m/z calcd for $C_{25}H_{20}FN_5O_3$ $[M+H]^+$ 458.16, m/z found 458.20.

RLX-20

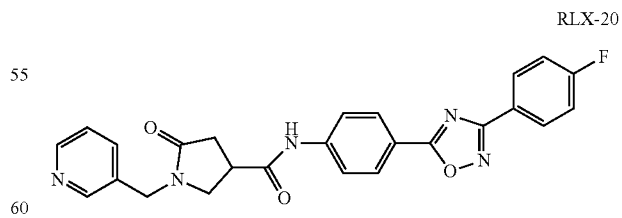

N-{4-[3-(4-Fluorophenyl)-1,2,4-oxadiazol-5-yl]phenyl}-5-oxo-1-[(pyridin-3-yl)methyl]-pyrrolidine-3-carboxamide (RLX-20). The procedure for RLX-1 was followed using 5-oxo-1-[(pyridin-3-yl)methyl]pyrrolidine-3-carboxylic acid and 4-[3-(4-fluorophenyl)-1,2,4-oxadizaol-5-yl]aniline to give the target compound RLX-20 (50% yield) as a pale yellow powder. $^1$H NMR (300 MHz, DMSO-$d_6$) δ 10.53; (s, 1H), 8.53-8.48; (m, 2H), 8.17-8.08; (m, 4H), 7.86; (d, J=9.0 Hz, 2H), 7.71-7.64; (m, 1H), 7.48-7.36; (m, 3H), 4.46; (s, 2H), 3.62-3.52; (m, 1H), 3.47-3.33; (m, 2H), 2.74-2.55; (m, 2H); $^{13}$C NMR (75 MHz, DMSO-$d_6$) δ 175.16, 172.25, 171.92, 167.32, 163.93; (d, $J_{C-F}$=247.5 Hz). 148.84, 148.44, 143.37, 135.46, 132.38, 129.57; (d, $J_{C-F}$=9.8 Hz), 128.98, 123.64, 122.80; (d, $J_{C-F}$=3.8 Hz), 119.39, 117.74, 116.36; (d, $J_{C-F}$=22.5 Hz), 48.81, 42.93, 37.12, 33.73; HRMS (ESI) m/z calcd for $C_{25}H_{20}FN_5O_3$ [M+H]$^+$ 458.1623, m/z found 458.1642.

RLX-21

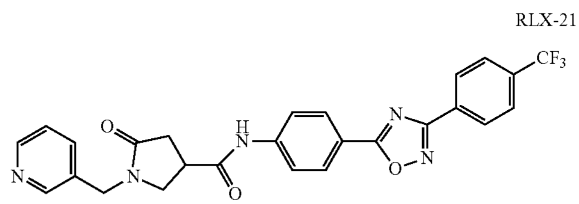 [SMILES: O=C(Nc1ccc(-c2nc(-c3ccc(C(F)(F)F)cc3)no2)cc1)C1CC(=O)N(Cc2cccnc2)C1]

5-Oxo-1-[(pyridin-3-yl)methyl]-N-(4-{3-[4-(trifluoromethyl)phenyl]-1,2,4-oxadiazol-5-yl}phenyl)-pyrrolidine-3-carboxamide (RLX-21). The procedure for RLX-1 was followed using 5-oxo-1-[(pyridin-3-yl)methyl]pyrrolidine-3-carboxylic acid and 4-{3-[4-(trifluoromethyl)phenyl]-1,2,4-oxadizaol-5-yl}aniline to give the target compound RLX-21 (49% yield) as a pale yellow powder. $^1$H NMR (300 MHz, DMSO-$d_6$) δ 10.55 (s, 1H), 8.54-8.49; (m, 2H), 8.29; (d, J=9.0 Hz, 2H), 8.16; (d. J=9.0 Hz, 2H), 7.97; (d. J=9.0 Hz, 2H), 7.87; (d. J=9.0 Hz, 2H), 7.73-7.66; (m, 1H), 7.45-7.38; (m, 1H). 4.46; (s, 2H), 3.63-3.52; (m, 1H), 3.48-3.34; (m, 2H), 2.75-2.54 (m, 2H); $^{13}$C NMR (75 MHz, DMSO-$d_6$) δ 175.54, 172.26, 171.95, 167.16, 148.66, 148.29, 143.50, 135.67, 132.48, 131.57, 131.15, 130.09; (q. $J_{C-F}$=1.5 Hz), 129.07, 127.90, 126.18; (q. $J_{C-F}$=4.0 Hz), 123.71, 119.41, 117.58, 48.81, 42.92, 37.13, 33.73; HRMS (ESI) m/z calcd for $C_{26}H_{20}F_3N_5O_3$ [M+H]$^+$ 508.1591, m/z found 508.1613.

RLX-22

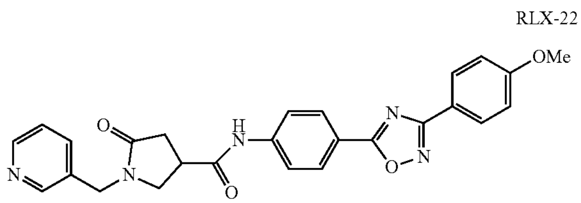 [SMILES: COc1ccc(-c2noc(-c3ccc(NC(=O)C4CC(=O)N(Cc5cccnc5)C4)cc3)n2)cc1]

N-{4-[3-(4-Methoxyphenyl)-1,2,4-oxadiazol-5-yl]phenyl}-5-oxo-1-[(pyridin-3-yl)methyl]-pyrrolidine-3-carboxamide (RLX-22). The procedure for RLX-1 was followed using 5-oxo-1-[(pyridin-3-yl)methyl]pyrrolidine-3-carboxylic acid and 4-[3-(4-methoxyphenyl)-1,2,4-oxadizaol-5-yl]aniline to give the target compound RLX-22 (49% yield) as a pale brown powder. $^1$H NMR (300 MHz, $CDCl_3$) δ 9.49; (s, 1H), 8.54; (br s, 2H), 8.10; (d, J=9.0 Hz, 2H), 8.06; (d, J=9.0 Hz, 2H), 7.78-7.65; (m, 3H), 7.38-7.30; (m, 1H), 6.98; (d, J=9.0 Hz, 2H), 4.61; (d, J=15.0 Hz, 1H), 4.43; (d, J=15.0 Hz, 1H), 3.86; (s, 3H), 3.70; (dd, J=9.0, 6.0 Hz, 1H), 3.51; (t, J=9.0 Hz, 1H), 3.38-3.26; (m, 1H), 2.90; (dd, J=16.5, 7.5 Hz, 1H), 2.69; (dd, J=16.5, 10.5 Hz, 1H); $^{13}$C NMR (75 MHz, $CDCl_3$) δ 174.78, 172.79, 170.63, 168.58, 161.93, 148.96, 148.84, 141.98, 136.27, 129.17, 129.03, 120.02, 119.68, 119.31, 114.22, 55.33, 49.13, 44.13, 38.25, 34.78; HRMS (ESI) m/z calcd for $C_{26}H_{23}N_5O_4$ [M+H]$^+$ 470.1823, m/z found 470.1841.

RLX-23

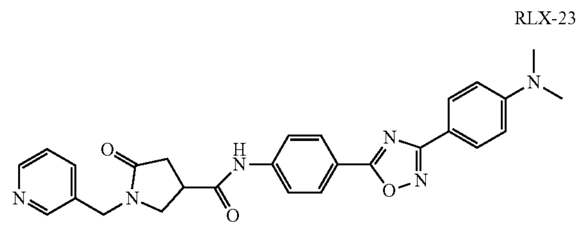 [SMILES: CN(C)c1ccc(-c2noc(-c3ccc(NC(=O)C4CC(=O)N(Cc5cccnc5)C4)cc3)n2)cc1]

N-(4-{3-[4-(Dimethylamino)phenyl]-1,2,4-oxadiazol-5-yl}phenyl)-5-oxo-1-[(pyridin-3-yl)methyl]-pyrrolidine-3-carboxamide (RLX-23). The procedure for RLX-1 was followed using 5-oxo-1-[(pyridin-3-yl)methyl]pyrrolidine-3-carboxylic acid and 4-{3-[4-(dimethylamino)phenyl]-1,2,4-oxadizaol-5-yl}aniline to give the target compound RLX-23 (50% yield) as a pale brown powder. $^1$H NMR (300 MHz, $CDCl_3$) δ 9.47; (s, 1H). 8.55-8.48; (m, 2H), 8.08; (d, J=9.0 Hz, 2H), 7.96; (d, J=9.0 Hz, 2H), 7.73; (d, J=9.0 Hz, 2H), 7.65-7.60; (m, 1H), 7.31; (dd, J=7.5, 4.5 Hz, 1H), 6.73; (d, J=9.0 Hz, 2H), 4.57; (d, J=15.0 Hz, 1H), 4.41; (d, J=15.0 Hz, 1H), 3.67; (dd, J=9.0, 6.0 Hz, 1H), 3.48; (t, J=9.0 Hz, 1H), 3.36-3.24; (m, 1H), 3.01; (s, 6H), 2.89; (dd, J=18.0, 6.0 Hz, 1H), 2.67; (dd, J=18.0, 10.5 Hz, 1H); $^{13}$C NMR (75 MHz, $CDCl_3$) δ 174.40, 172.79, 170.64, 169.03, 152.19, 149.03, 148.95, 141.87, 136.13, 131.85, 129.12, 128.61, 124.03, 120.17, 119.66, 113.88, 111.63, 49.13, 44.10, 40.06, 38.20, 34.74; HRMS (ESI) m/z calcd for $C_{27}H_{26}N_6O_3$ [M+H]$^+$ 483.2139, m/z found 483.2154.

RLX-24

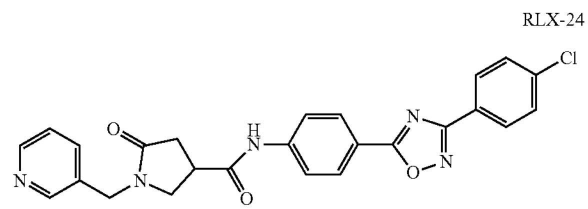 [SMILES: O=C(Nc1ccc(-c2nc(-c3ccc(Cl)cc3)no2)cc1)C1CC(=O)N(Cc2cccnc2)C1]

N-{4-[3-(4-Chlorophenyl)-1,2,4-oxadiazol-5-yl]phenyl}-5-oxo-1-[(pyridin-3-yl)methyl]-pyrrolidine-3-carboxamide (RLX-24). The procedure for RLX-1 was followed using 5-oxo-1-[(pyridin-3-yl)methyl]pyrrolidine-3-carboxylic acid and 4-[3-(4-chlorophenyl]-1,2,4-oxadizaol-5-yl)aniline to give the target compound RLX-24 (53% yield) as a pale yellow powder. $^1$H NMR (300 MHz, DMSO-$d_6$) δ 10.56; (s, 1H), 8.53; (d, J=3.0 Hz, 2H), 8.14; (d, J=9.0 Hz, 2H), 8.09; (d, J=9.0 Hz, 2H), 7.87; (d, J=9.0 Hz, 2H), 7.74-7.63; (m, 3H), 7.43; (dd, J=7.5, 4.5 Hz, 1H), 4.47; (s, 2H), 3.64-3.53; (m, 1H), 3.50-3.35; (m, 2H), 2.75-2.55; (m, 2H); $^{13}$C NMR (75 MHZ, $CDCl_3$) δ 175.26, 172.27, 171.94, 167.32, 148.65, 148.29, 143.42, 136.26, 135.68, 132.49, 129.37, 129.00, 128.81, 125.08, 123.73, 119.38, 117.68, 48.82, 42.92, 37.13, 33.74; HRMS (ESI) m/z calcd for $C_{25}H_{20}ClN_5O_3$ [M+H]$^+$ 474.1327, m/z found 474.1348.

RLX-25

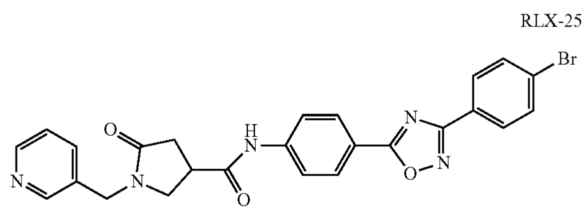

N-{4-[3-(4-Bromophenyl)-1,2,4-oxadiazol-5-yl]phenyl}-5-oxo-1-[(pyridin-3-yl)methyl]-pyrrolidine-3-carboxamide (RLX-25). The procedure for RLX-1 was followed using 5-oxo-1-[(pyridin-3-yl)methyl]pyrrolidine-3-carboxylic acid and 4-[3-(4-bromophenyl]-1,2,4-oxadizaol-5-yl)aniline to give the target compound RLX-25 (52% yield) as a pale brown powder. $^1$H NMR (300 MHz, DMSO-$d_6$) δ 10.58; (s, 1H), 8.56-8.51; (m, 2H), 8.14; (d, J=9.0 Hz, 2H), 8.02; (d, J=9.0 Hz, 2H), 7.87; (d, J=9.0 Hz, 2H), 7.81; (d, J=9.0 Hz, 2H), 7.77-7.70; (m, 1H), 7.46; (dd, J=9.0, 6.0 Hz, 1H), 4.48; (s, 2H), 3.64-3.54; (m, 1H), 3.48-3.36; (m, 2H), 2.75-2.55; (m, 2H); $^{13}$C NMR (75 MHz, $CDCl_3$) δ 175.27, 172.30, 171.94, 167.43, 148.29, 147.94, 143.42, 136.10, 132.70, 132.29, 129.00, 128.96, 125.42, 125.10, 123.86, 119.38, 117.66, 48.83, 42.89, 37.12, 33.73; HRMS (ESI) m/z calcd for $C_{25}H_{20}BrN_5O_3$ $[M+H]^+$ 518.0822, m/z found 518.0846.

RLX-26

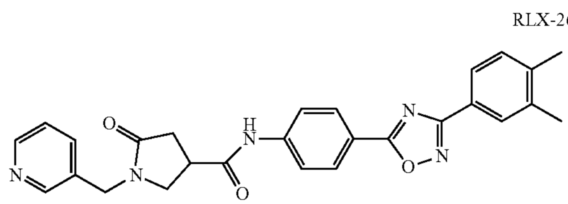

N-{4-[3-(3,4-Dimethylphenyl)-1,2,4-oxadiazol-5-yl]phenyl}-5-oxo-1-[(pyridin-3-yl)methyl]-pyrrolidine-3-carboxamide (RLX-26). The procedure for RLX-1 was followed using 5-oxo-1-[(pyridin-3-yl)methyl]pyrrolidine-3-carboxylic acid and 4-[3-(3,4-dimethylphenyl]-1,2,4-oxadizaol-5-yl)aniline to give the target compound RLX-26 (58% yield) as a pale brown powder. $^1$H NMR (300 MHz, $CDCl_3$) δ 9.58; (s, 1H), 8.55-8.50; (m, 2H), 8.10; (d, J=9.0 Hz, 2H), 7.90-7.82; (m, 2H), 7.75; (d, J=9.0 Hz, 2H), 7.68-7.62; (m, 1H), 7.36-7.30; (m, 1H), 7.23; (d, J=9.0 Hz, 1H), 4.60; (d, J=15.0 Hz, 1H), 4.42; (d, J=15.0 Hz, 1H), 3.70; (dd, J=9.0, 6.0 Hz, 1H), 3.50; (t, J=9.0 Hz, 1H), 3.38-3.26; (m, 1H), 2.89; (dd, J=16.5, 7.5 Hz, 1H), 2.69; (dd, J=16.5, 9.0 Hz, 1H), 2.31; (s, 6H); $^{13}$C NMR (75 MHz, $CDCl_3$) δ 174.40, 172.79, 170.64, 169.03, 152.19, 149.03, 148.95, 141.87, 136.13, 131.85, 129.12, 128.61, 124.03, 120.17, 119.66, 113.88, 111.63, 49.13, 44.10, 40.06, 38.20, 34.74; HRMS (ESI) m/z calcd for $C_{27}H_{25}N_5O_3$ $[M+H]^+$ 468.2030, m/z found 468.2049.

RLX-27

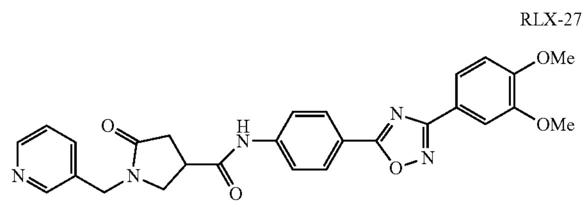 [SMILES: COc1ccc(-c2noc(-c3ccc(NC(=O)C4CC(=O)N(Cc5cccnc5)C4)cc3)n2)cc1OC]

N-{4-[3-(3,4-Dimethoxyphenyl)-1,2,4-oxadiazol-5-yl]phenyl}-5-oxo-1-[(pyridin-3-yl)methyl]-pyrrolidine-3-carboxamide (RLX-27). The procedure for RLX-1 was followed using 5-oxo-1-[(pyridin-3-yl)methyl]pyrrolidine-3-carboxylic acid and 4-[3-(3,4-dimethoxyphenyl]-1,2,4-oxadizaol-5-yl)aniline to give the target compound RLX-27 (56% yield) as a pale brown powder. $^1$H NMR (300 MHz, $CDCl_3$) δ 9.54-9.44; (m, 1H), 8.58-8.52; (m, 2H), 8.12; (d, J=9.0 Hz, 2H), 7.78-7.72; (m, 3H), 7.68-7.62; (m, 2H), 7.34; (dd, J=9.0, 6.0 Hz, 1H), 6.96; (d, J=9.0 Hz, 1H), 4.62; (d, J=15.0 Hz, 1H), 4.43; (d, J=15.0 Hz, 1H), 3.72; (dd, J=10.5, 7.5 Hz, 1H), 3.51; (t, J=9.0 Hz, 1H), 3.38-3.26; (m, 1H), 2.91; (dd, J=16.5, 7.5 Hz, 1H), 2.70; (dd, J=16.5, 9.0 Hz, 1H); $^{13}$C NMR (75 MHz, $CDCl_3$) δ 174.82, 172.77, 170.63, 168.62, 151.49, 149.12, 149.02, 148.89, 142.03, 136.21, 131.87, 129.21, 124.07, 120.90, 119.95, 119.65, 119.45, 111.07, 109.99, 56.01, 55.91, 49.09, 44.13, 38.27, 34.78; HRMS (ESI) m/z calcd for $C_{27}H_{25}N_5O_5$ $[M+H]^+$ 500.1928, m/z found 500.1946.

RLX-28

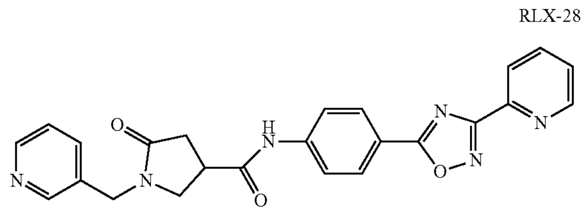 [SMILES: O=C(Nc1ccc(-c2nc(-c3ccccn3)no2)cc1)C1CC(=O)N(Cc2cccnc2)C1]

5-Oxo-N-{4-[3-(pyridin-2-yl)-1,2,4-oxadiazol-5-yl]phenyl}-1-[(pyridin-3-yl)methyl]-pyrrolidine-3-carboxamide (RLX-28). The procedure for RLX-1 was followed using 5-oxo-1-[(pyridin-3-yl)methyl]pyrrolidine-3-carboxylic acid and 4-[3-(pyridin-2-yl)-1,2,4-oxadiazol-5-yl]aniline to give the target compound RLX-28 (48% yield) as a pale yellow powder. $^1$H NMR (300 MHz, $CD_3OD$) δ 8.60-8.55; (m, 1H), 8.41; (d, J=3.0 Hz, 1H), 8.36; (dd, J=6.0, 3.0 Hz, 1H), 8.05; (d, J=6.0 Hz, 1H), 7.98-7.91; (m, 2H), 7.90-7.82; (m, 1H), 7.71-7.60; (m, 3H), 7.46-7.40; (m, 1H), 7.32; (dd, J=7.5, 4.5 Hz, 1H), 4.49; (d, J=15.0 Hz, 1H), 4.41; (d, J=15.0 Hz, 1H), 3.59-3.44; (m, 2H), 3.34-3.22; (m, 1H), 2.67; (d, J=6.0 Hz, 2H); $^{13}$C NMR (75 MHz, $CD_3OD$) δ 177.51, 175.73, 173.59, 169.66, 151.16, 149.90, 149.56, 147.43, 144.64, 139.25, 138.01, 134.23, 130.31, 127.43, 125.55, 124.80, 120.98, 120.22, 50.92, 44.88, 39.04, 35.61; HRMS (ESI) m/z calcd for $C_{24}H_{20}N_6O_3$ $[M+H]^+$ 441.167, m/z found 441.1688.

RLX-29

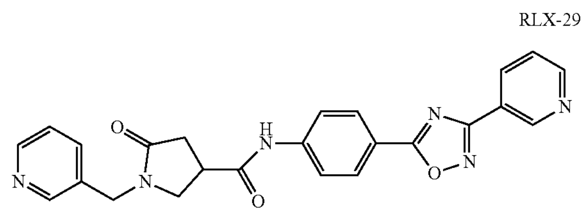 [SMILES: O=C(Nc1ccc(-c2nc(-c3cccnc3)no2)cc1)C1CC(=O)N(Cc2cccnc2)C1]

5-Oxo-N-{4-[3-(pyridin-3-yl)-1,2,4-oxadiazol-5-yl]phenyl}-1-[(pyridin-3-yl)methyl]-pyrrolidine-3-carboxamide (RLX-29). The procedure for RLX-1 was followed using 5-oxo-1-[(pyridin-3-yl)methyl]pyrrolidine-3-carboxylic acid and 4-[3-(pyridin-3-yl)-1,2,4-oxadiazol-5-yl]aniline to give the target compound RLX-29 (46% yield) as a pale yellow powder. $^1$H NMR (300 MHz, $CD_3OD$) δ 9.18-9.13;

(m, 1H), 8.66; (dd, J=6.0, 3.0 Hz, 1H), 8.54-8.37; (m, 3H), 8.03; (d, J=9.0 Hz, 2H), 7.83-7.69; (m, 3H), 7.58-7.50; (m, 1H), 7.46-7.38; (m, 1H), 4.60; (d, J=15.0 Hz, 1H), 4.52; (d, J=15.0 Hz, 1H), 3.70-3.55; (m, 2H), 3.45-3.33; (m, 1H), 2.79; (d, J=9.0 Hz, 2H); $^{13}C$ NMR (75 MHZ, $CD_3OD$) δ 177.36, 175.74, 173.61, 167.97, 152.70, 149.91, 149.57, 148.94, 144.65, 138.03, 136.65, 134.25, 130.30, 125.68, 125.55, 125.16, 120.98, 120.19, 50.92, 44.89, 39.04, 35.63; HRMS (ESI) m/z calcd for $C_{24}H_{20}N_6O_3$ $[M+H]^+$ 441.167, m/z found 441.1688.

RLX-30

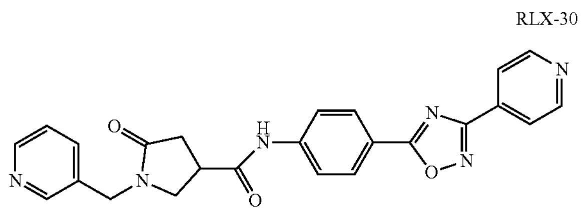 [SMILES: O=C(Nc1ccc(-c2nc(-c3ccncc3)no2)cc1)C1CC(=O)N(Cc2cccnc2)C1]

5-Oxo-N-{4-[3-(pyridin-4-yl)-1,2,4-oxadiazol-5-yl]phenyl}-1-[(pyridin-3-yl)methyl]-pyrrolidine-3-carboxamide (RLX-30). The procedure for RLX-1 was followed using 5-oxo-1-[(pyridin-3-yl)methyl]pyrrolidine-3-carboxylic acid and 4-[3-(pyridin-4-yl)-1,2,4-oxadiazol-5-yl]aniline to give the target compound RLX-30 (52% yield) as a pale yellow powder. $^1H$ NMR (300 MHz, $CD_3OD$) δ 8.75-8.69; (m, 2H), 8.54-8.45; (m, 2H), 8.14-8.04; (m, 4H), 7.84-7.76; (m, 3H), 7.48-7.41; (m, 1H), 4.62; (d, J=15.0 Hz, 1H), 4.53; (d, J=15.0 Hz, 1H), 3.72-3.56; (m, 2H), 3.46-3.36; (m, 1H), 2.79; (d, J=9.0 Hz, 2H); $^{13}C$ NMR (75 MHZ, $CD_3OD$) δ 177.81, 175.78, 173.72, 168.51, 151.41, 149.91, 149.57, 144.79, 138.06, 136.76, 134.26, 130.35, 125.57, 122.95, 121.08, 120.19, 50.94, 44.89, 39.06, 35.63; HRMS (ESI) m/z calcd for $C_{24}H_{20}N_6O_3$ $[M+H]^+$ 441.167, m/z found 441.1688.

RLX-31

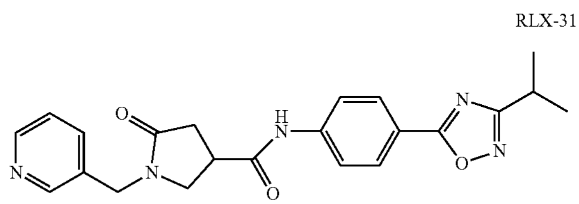 [SMILES: CC(C)c1noc(-c2ccc(NC(=O)C3CC(=O)N(Cc4cccnc4)C3)cc2)n1]

5-Oxo-N-{4-[3-(propan-2-yl)-1,2,4-oxadiazol-5-yl]phenyl}-1-[(pyridin-3-yl)methyl]-pyrrolidine-3-carboxamide (RLX-31). The procedure for RLX-1 was followed using 5-oxo-1-[(pyridin-3-yl)methyl]pyrrolidine-3-carboxylic acid and 4-[3-(propan-2-yl)-1,2,4-oxadiazol-5-yl]aniline to give the target compound RLX-31 (47% yield) as a yellow powder. $^1H$ NMR (300 MHz, $CDCl_3$) δ 9.76; (s, 1H), 8.56; (br s. 2H), 8.02; (d, J=9.0 Hz, 2H), 7.80-7.67; (m, 3H), 7.37; (dd, J=7.5, 4.5 Hz, 1H), 4.58; (d, J=15.0 Hz, 1H), 4.47; (d, J=15.0 Hz, 1H), 3.70; (dd, J=9.0, 6.0 Hz, 1H), 3.54; (t, J=9.0 Hz, 1H), 3.48-3.34; (m, 1H), 3.21-3.06; (m, 1H), 2.88; (dd, J=18.0, 6.0 Hz, 1H), 2.71; (dd, J=18.0, 9.0 Hz, 1H), 1.38; (d, J=6.0 Hz, 6H); $^{13}C$ NMR (75 MHz, $CD_3OD$) δ 175.66, 174.62, 172.97, 170.82, 148.33, 148.27, 141.96, 136.80, 132.30, 129.02, 124.27, 120.04, 119.64, 49.26, 44.04, 38.08, 34.73, 26.78, 20.48; HRMS (ESI) m/z calcd for $C_{22}H_{23}N_5O_3$ $[M+H]^+$ 406.1874, m/z found 406.1891.

RLX-32

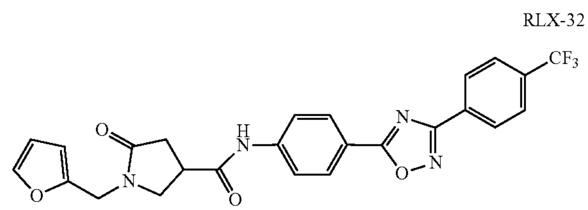 [SMILES: O=C(Nc1ccc(-c2nc(-c3ccc(C(F)(F)F)cc3)no2)cc1)C1CC(=O)N(Cc2ccco2)C1]

1-[(Furan-2-yl)methyl]-5-oxo-N-(4-{3-[4-(trifluoromethyl)phenyl]-1,2,4-oxadiazol-5-yl}phenyl)pyrrolidine-3-carboxamide (RLX-32). The procedure for RLX-1 was followed using 1-[(furan-2-yl)methyl]-5-oxopyrrolidine-3-carboxylic acid and 4-{3-[4-(trifluoromethyl)phenyl]-1,2,4-oxadizaol-5-yl}aniline to give the target compound RLX-32 (75% yield) as a white powder. $^1H$ NMR (300 MHz, DMSO-$d_6$) δ 10.54; (s, 1H), 8.30; (d, J=9.0 Hz, 2H), 8.17; (d, J=9.0 Hz, 2H), 7.98; (d, J=9.0 Hz, 2H), 7.89; (d, J=9.0 Hz, 2H), 7.64-7.60; (m, 1H), 6.45-6.41; (m, 1H), 6.38-6.35; (m, 1H), 4.46; (d, J=15.0 Hz, 1H), 4.39; (d, J=15.0 Hz, 1H), 3.60; (t, J=9.0 Hz, 1H), 3.49-3.34; (m, 2H), 2.65-2.55; (m, 2H); $^{13}C$ NMR (75 MHz, DMSO-$d_6$) δ 175.53, 171.74, 171.66, 167.17, 149.94, 143.50, 142.74, 130.08, 129.07, 127.89, 126.19, 126.14, 119.40, 117.58, 110.42, 108.12, 48.81, 38.43, 37.05, 33.67; HRMS (ESI) m/z calcd for $C_{25}H_{19}F_3N_4O_4$ $[M+H]^+$ 497.1431, m/z found 497.1454.

RLX-33

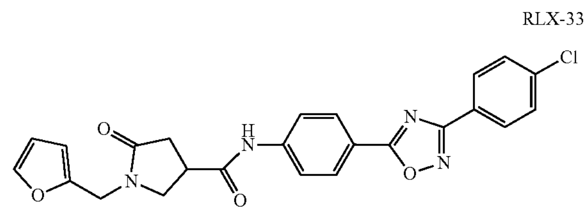 [SMILES: O=C(Nc1ccc(-c2nc(-c3ccc(Cl)cc3)no2)cc1)C1CC(=O)N(Cc2ccco2)C1]

N-{4-[3-(4-Chlorophenyl)-1,2,4-oxadiazol-5-yl]phenyl}-1-[(furan-2-yl)methyl]-5-oxopyrrolidine-3-carboxamide (RLX-33). The procedure for RLX-1 was followed using 1-[(furan-2-yl)methyl]-5-oxopyrrolidine-3-carboxylic acid and 4-[3-(4-chlorophenyl)-1,2,4-oxadiazol-5-yl]aniline to give the target compound RLX-33 (67% yield) as a white powder. $^1H$ NMR (300 MHz, DMSO-$d_6$) δ 10.53; (s, 1H), 8.13; (d, J=9.0 Hz, 2H), 8.10; (d, J=9.0 Hz, 2H), 7.87; (d, J=9.0 Hz, 2H), 7.68; (d, J=9.0 Hz, 2H), 7.64-7.60; (m, 1H), 6.45-6.41; (m, 1H), 6.38-6.35; (m, 1H), 4.46; (d, J=16.5 Hz, 1H), 4.38; (d, J=16.5 Hz, 1H), 3.59; (t, J=9.0 Hz, 1H), 3.49-3.33; (m, 2H), 2.63-2.57; (m, 2H); $^{13}C$ NMR (75 MHz, DMSO-$d_6$) δ 175.28, 171.74, 171.67, 167.33, 149.95, 143.42, 142.75, 136.27, 129.38, 129.02, 128.82, 125.08, 119.39, 117.69, 110.43, 108.13, 48.82, 38.43, 37.05, 33.68; HRMS (ESI) m/z calcd for $C_{24}H_{19}ClN_4O_4$ $[M+H]^+$ 463.1168, m/z found 463.1184.

RLX-34

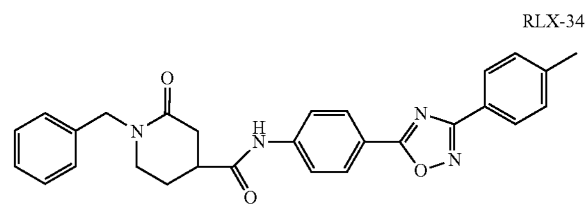 [SMILES: Cc1ccc(-c2noc(-c3ccc(NC(=O)C4CCN(Cc5ccccc5)C(=O)C4)cc3)n2)cc1]

1-Benzyl-N-{4-[3-(4-methylphenyl)-1,2,4-oxadiazol-5-yl]phenyl}-2-oxopiperidine-4-carboxamide (RLX-34). The procedure for RLX-1 was followed using 1-benzyl-2-oxopiperidine-4-carboxylic acid and 4-[3-(4-methylphenyl)-1,2,4-oxadizaol-5-yl]aniline to give the target compound RLX-34 (52% yield) as an off-white powder. $^1$H NMR (300 MHz, DMSO-$d_6$) δ 10.45; (s, 1H), 8.14; (d, J=9.0 Hz, 2H), 7.98; (d, J=9.0 Hz, 2H), 7.88; (d, J=9.0 Hz, 2H), 7.41; (d, J=9.0 Hz, 2H), 7.35; (d, J=9.0 Hz, 2H), 7.32-7.22; (m, 3H), 4.55; (m, 2H), 3.30-3.20; (m, 2H), 3.05-2.92; (m, 1H), 2.60-2.50; (m, 2H), 2.40; (s, 3H), 2.15-2.02; (m, 1H), 1.98-1.82; (m, 1H); $^{13}$C NMR (75 MHZ, DMSO-$d_6$) δ 174.94, 172.47, 168.07, 167.57, 143.44, 141.46, 137.43, 129.73, 128.94, 128.39, 127.39, 126.96, 123.46, 119.25, 117.73, 48.92, 45.27, 39.57, 33.94, 25.85, 21.03; HRMS (ESI) m/z calcd for $C_{28}H_{26}N_4O_3$ [M+H]$^+$ 467.2078, m/z found 467.2095.

RLX-35

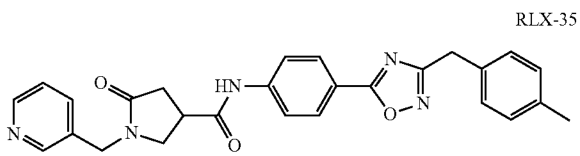 [SMILES: Cc1ccc(Cc2noc(-c3ccc(NC(=O)C4CC(=O)N(Cc5cccnc5)C4)cc3)n2)cc1]

N-(4-{3-[(4-Methylphenyl)methyl]-1,2,4-oxadiazol-5-yl}phenyl)-5-oxo-1-[(pyridin-3-yl)methyl]-pyrrolidine-3-carboxamide (RLX-35). The procedure for RLX-1 was followed using 5-oxo-1-[(pyridin-3-yl)methyl]pyrrolidine-3-carboxylic acid and 4-{3-[(4-methylphenyl)methyl]-1,2,4-oxadiazol-5-yl}aniline to give the target compound RLX-35 (53% yield) as a pale brown powder. $^1$H NMR (300 MHz, $CDCl_3$) δ 9.53; (s, 1H). 8.55-8.46; (m, 2H), 7.99; (d, J=9.0 Hz, 2H), 7.68; (d, J=9.0 Hz, 2H), 7.78-7.72; (m, 1H), 7.64-7.58; (m, 1H), 7.32-7.26; (m, 1H), 7.24; (d, J=9.0 Hz, 1H), 7.11; (d, J=6.0 Hz, 2H), 4.57 (d, J=15.0 Hz, 1H), 4.38; (d, J=15.0 Hz, 1H), 4.06; (s, 2H), 3.65; (dd, J=10.5, 7.5 Hz, 1H), 3.45; (t, J=9.0 Hz, 1H), 3.32-3.18; (m, 1H), 2.85; (dd, J=16.5, 7.5 Hz, 1H), 2.64; (dd, J=16.5, 10.5 Hz, 1H), 2.30; (s, 3H); $^{13}$C NMR (75 MHz, $CDCl_3$) δ 175.07, 172.77, 170.61, 170.20, 149.01, 148.88, 142.04, 136.68, 136.14, 132.34, 131.79, 129.31, 129.13, 128.80, 124.02, 119.76, 119.57, 49.07, 44.08, 38.12, 34.71, 31.96, 20.95; HRMS (ESI) m/z calcd for $C_{27}H_{25}N_5O_3$ [M+H]$^+$ 468.2030, m/z found 468.2049.

RLX-36

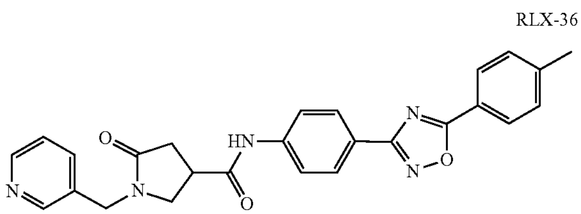 [SMILES: Cc1ccc(-c2nc(-c3ccc(NC(=O)C4CC(=O)N(Cc5cccnc5)C4)cc3)no2)cc1]

N-{4-[5-(4-Methylphenyl)-1,2,4-oxadiazol-3-yl]phenyl}-5-oxo-1-[(pyridin-3-yl)methyl]-pyrrolidine-3-carboxamide (RLX-36). The procedure for RLX-1 was followed using 5-oxo-1-[(pyridin-3-yl)methyl]pyrrolidine-3-carboxylic acid and 4-[5-(4-methylphenyl)-1,2,4-oxadiazol-3-yl]aniline to give the target compound RLX-36 (57% yield) as a white powder. $^1$H NMR (300 MHz, $CDCl_3$) δ 9.19; (s, 1H), 8.55-8.00; (m, 2H), 8.08; (d, J=6.0 Hz, 2H), 8.05; (d, J=6.0 Hz, 2H), 7.72-7.62; (m, 3H), 7.35-7.25; (m, 3H). 4.60; (d, J=15.0 Hz, 1H), 4.41; (d, J=15.0 Hz, 1H), 3.68 (dd, J=10.5, 7.5 Hz, 1H), 3.49; (t, J=9.0 Hz, 1H), 3.36-3.22; (m, 1H), 2.90; (dd, J=16.5, 7.5 Hz, 1H), 2.71; (dd, J=16.5, 9.0 Hz, 1H), 2.43; (s, 3H); $^{13}$C NMR (75 MHz, $CDCl_3$) δ 175.76, 172.80, 170.45, 168.25, 149.09, 149.04, 143.50, 140.51, 136.12, 131.84, 129.76, 128.38, 128.06, 124.01, 122.95, 121.44, 119.77, 49.14, 44.11, 38.27, 34.78, 21.68; HRMS (ESI) m/z calcd for $C_{26}H_{23}N_5O_3$ [M+H]$^+$ 454.1874, m/z found 454.1894.

RLX-37

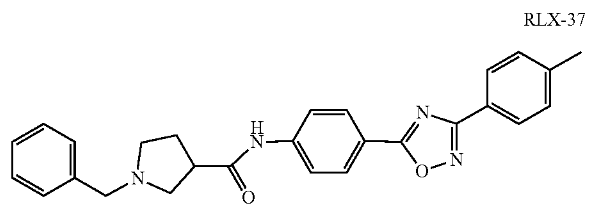 [SMILES: Cc1ccc(-c2noc(-c3ccc(NC(=O)C4CCN(Cc5ccccc5)C4)cc3)n2)cc1]

1-Benyl-N-{4-[3-(4-methylphenyl)-1,2,4-oxadiazol-5-yl]phenyl}-pyrrolidine-3-carboxamide (RLX-37). The procedure for RLX-1 was followed using 1-benzylpyrrolidine-3-carboxylic acid and 4-[5-(4-methylphenyl)-1,2,4-oxadiazol-3-yl]aniline to give the target compound RLX-37 (57% yield) as an off-white powder. $^1$H NMR (300 MHz, $CDCl_3$) δ 9.90; (s, 1H), 8.16; (d, J=9.0 Hz, 2H), 8.06; (d, J=9.0 Hz, 2H), 7.69; (d, J=9.0 Hz, 2H), 7.45-7.23; (m, 7H), 3.88-3.64; (m, 2H), 3.24-3.14; (m, 2H), 3.08-2.96; (m, 1H), 2.53-2.28; (m, 6H), 2.20-2.02; (m, 1H; $^{13}$C NMR (75 MHz, $CDCl_3$) δ 175.23, 174.87, 168.88, 142.77, 141.36, 129.51, 129.23, 128.81, 128.73, 127.79, 127.43, 124.28, 119.31, 119.21, 59.37, 56.96, 52.45, 45.28, 28.71, 21.55; MS (ESI) m/z calcd for $C_{27}H_{26}N_4O_2$ [M+H]$^+$ 439.21, m/z found 439.20.

RLX-38

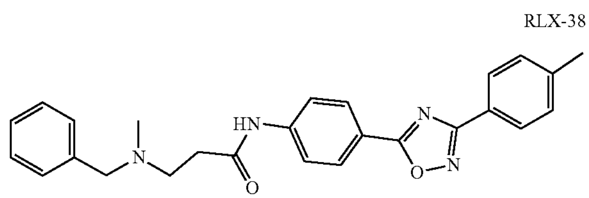 [SMILES: Cc1ccc(-c2noc(-c3ccc(NC(=O)CCN(C)Cc4ccccc4)cc3)n2)cc1]

3-[Benzyl(methyl)amino]-N-{4-[3-(4-methylphenyl)-1,2,4-oxadiazol-5-yl]phenyl}propanamide (RLX-38). To a solution of 3-[benzyl(methyl)amino]-propanoic acid (39 mg, 0.2 mmol) and DIPEA (198 μL, 1.2 mmol) in 5 mL $CH_2Cl_2$ were added 4-[3-(4-methylphenyl)-1,2,4-oxadizaol-5-yl]aniline (60 mg, 0.24 mmol) and T3P$^@$ (50% DMF solution, 255 mg, 0.4 mmol). After stirring at room temperature overnight, the mixture was concentrated under reduced pressure. Flash column chromatography of the crude product on silica gel using 0-5% MeOH in $CH_2Cl_2$ gave the target compound RLX-38 (30 mg, 35% yield) as an off-white powder. $^1$H NMR (300 MHz, $CDCl_3$) δ 10.91; (s, 1H), 8.15; (d, J=8.7 Hz, 2H), 8.06; (d, J=8.0 Hz, 2H), 7.73; (d, J=8.7 Hz, 2H), 7.41-7.34; (m, 5H), 7.31; (d, J=8.0 Hz, 2H), 3.78; (s, 2H), 2.99; (t, J=6.1 Hz, 2H), 2.77; (t, J=6.1 Hz, 2H), 2.43; (s, 3H), 2.09; (s, 3H); $^{13}$C NMR (75 MHZ, $CDCl_3$) δ 175.25, 170.56, 168.89, 142.58, 141.39, 135.26, 129.77, 129.52, 129.22, 128.84, 128.35, 127.45, 124.27, 119.69, 119.42, 61.46, 52.80, 40.62, 33.38, 21.56; MS (ESI) m/z calcd for $C_{26}H_{26}N_4O_2$ [M+H]$^+$ 427.21, m/z found 427.20.

RLX-39

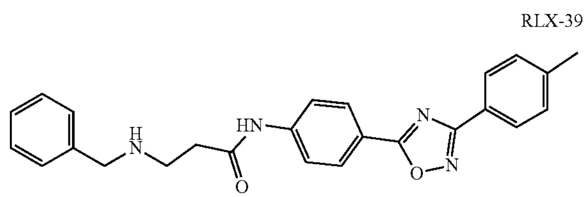 [SMILES: Cc1ccc(-c2noc(-c3ccc(NC(=O)CCNCc4ccccc4)cc3)n2)cc1]

3-[Benzylamino]-N-{4-[3-(4-methylphenyl)-1,2,4-oxadiazol-5-yl]phenyl}propanamide (RLX-39). The procedure for RLX-38 was followed using 3-{benzyl[(tert-butoxy)carbonyl]amino}propanoic acid and 4-[5-(4-methylphenyl)-1,2,4-oxadiazol-3-yl]aniline to afford the corresponding tert-butyloxycarbonyl (Boc)-protected amide intermediate. Removal of the Boc protecting group with trifluoroacidic acid (TFA) in $CH_2Cl_2$ gave the target compound RLX-39 (35% yield over two steps) as an off-white powder. $^1$H NMR (300 MHz, $CDCl_3$) δ 8.15; (d, J=8.5 Hz, 2H), 8.04; (d, J=7.9 Hz, 2H), 7.72; (d, J=8.5 Hz, 2H), 7.44-7.23; (m, 7H), 3.87; (s, 2H), 3.04; (t, J=5.9 Hz, 2H), 2.58; (t, J=5.9 Hz, 2H), 2.43; (s, 3H); $^{13}$C NMR (75 MHz, $CDCl_3$) δ 175.28, 171.28, 168.86, 142.50, 141.46, 138.73, 129.52, 129.21, 128.76, 128.23, 127.61, 127.40, 124.13, 119.51, 119.25, 53.45, 44.64, 36.10, 21.50; MS (ESI) m/z calcd for $C_{25}H_{24}N_4O_2$ $[M+H]^+$ 413.20, m/z found 413.20.

Example 2

Activity of RXFP3 Antagonists

CAMP assay: A stable CHO human RXFP3 (ES-656-C) cell line was purchased from PerkinElmer (Waltham. Massachusetts. United States of America) and used with the LANCE® Ultra kit (TRF0262; PerkinElmer, Waltham, Massachusetts. United States of America) to detect cAMP accumulation in 96-well plates. The assay is based on the competition between a europium chelate-labeled cAMP tracer and unlabeled cAMP produced by cells. Increases in cAMP accumulation result in a decrease in the TR-FRET signal detected at 665 nm. RXFP3 is a $G\alpha_{i/o}$-coupled receptor; therefore, the agonist relaxin-3 potently inhibits forskolin-stimulated CAMP accumulation. In cAMP accumulation assays, the $IC_{50}$ of the test compounds was calculated from concentration response curves of the test compound run in the presence of relaxin-3. CHO human RXFP3 cells were cultured in F12 media supplemented with 10% FBS, 100 units/mL penicillin, 100 μg/mL streptomycin, and 400 μg/mL geneticin. Stimulation buffer containing 1×HBSS, 5 mM HEPES (pH 7.4), 0.1% BSA stabilizer, and 0.5 mM IBMX was prepared. A concentration response curve of each test compound was prepared at 4 times the desired final concentration in 4% DMSO/stimulation buffer, and 5 μL was added to the assay plate. A single concentration of the agonist relaxin-3 was prepared at 4 times the desired final concentration in stimulation buffer (0.6 nM), and 5 μL was added to the assay plate. Forskolin (1 μM) was prepared at 4 times the desired concentration in stimulation buffer, and 5 μL was added to the assay plate. Cells were lifted from flasks with versene and spun at 270 g for 5 min. The cell pellet was resuspended in stimulation buffer and 5000 cells (5 μL) were added to each well. After incubating for 30 min at room temperature, Eu cAMP tracer and uLIGHT-anti-cAMP working solutions were added per the manufacturer's instructions. After 1 h, the TR-FRET signal (ex 337 nm) was read on a CLARIOstar multimode plate reader (BMG Biotech. Cary, North Carolina, United States of America). Fluorescence values at 665 nm were plotted against the log of compound concentration and nonlinear regression analysis (3-parameter) was used to generate $IC_{50}$ values (GraphPad Prism, GraphPad Software, Inc., San Diego, California, United States of America). FIG. 1 displays the concentration-response curves of representative compounds (RLX-1, RLX-24, and RLX-33) for inhibition of relaxin-3 activity in RXFP3 cAMP accumulation assays. $IC_{50}$ values of select RLX compounds are shown below in Table 1.

TABLE 1

Biological data for select RLX compounds.

| Compound # | Structure | $IC_{50}$ (nM)$^b$ |
|---|---|---|
| RLX-1 | 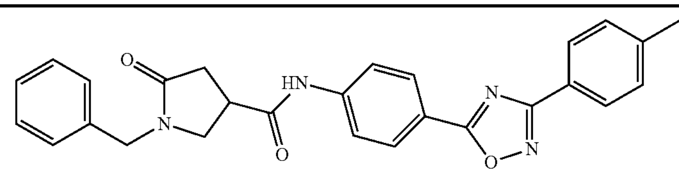 | 5308 ± 574 |
| RLX-2 | 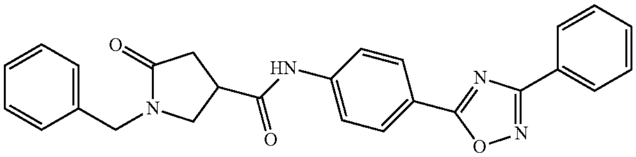 [SMILES: O=C(Nc1ccc(-c2nc(-c3ccccc3)no2)cc1)C1CC(=O)N(Cc2ccccc2)C1] | 7525 ± 998 |
| RLX-4 | 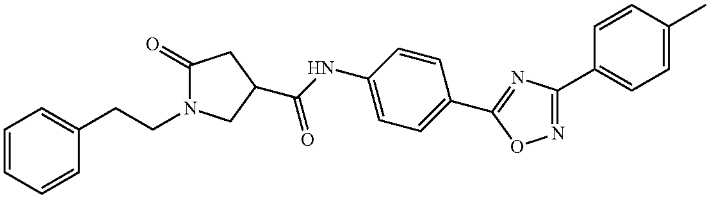 [SMILES: Cc1ccc(-c2noc(-c3ccc(NC(=O)C4CC(=O)N(CCc5ccccc5)C4)cc3)n2)cc1] | >10,000 |

TABLE 1-continued
| Biological data for select RLX compounds. | | |
|---|---|---|
| Compound # | Structure | $IC_{50}$ (nM)[b] |
| RLX-5 | 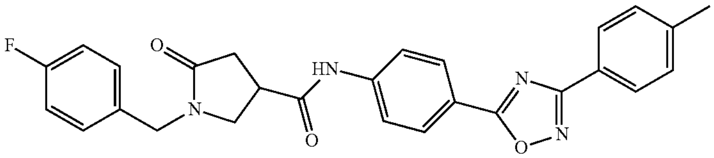 [SMILES: Cc1ccc(-c2noc(-c3ccc(NC(=O)C4CC(=O)N(Cc5ccc(F)cc5)C4)cc3)n2)cc1] | 7436 ± 654 |
| RLX-6 | 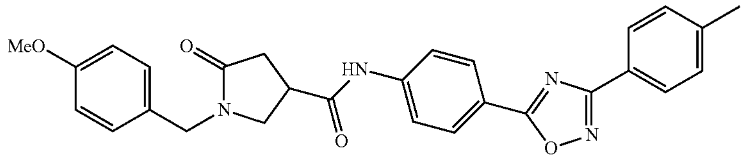 [SMILES: COc1ccc(CN2CC(C(=O)Nc3ccc(-c4nc(-c5ccc(C)cc5)no4)cc3)CC2=O)cc1] | >10,000 |
| RLX-7 | 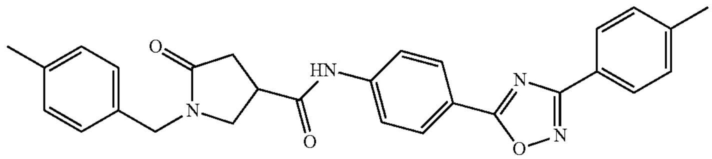 | >10,000 |
| RLX-8 | 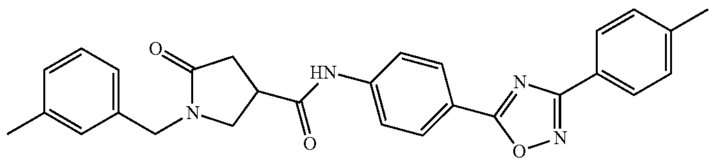 | >10,000 |
| RLX-9 | 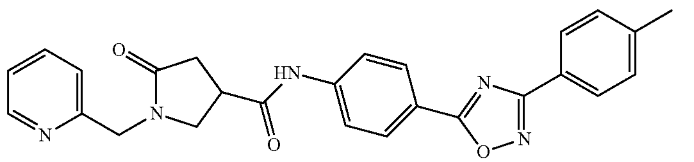 [SMILES: Cc1ccc(-c2noc(-c3ccc(NC(=O)C4CC(=O)N(Cc5ccccn5)C4)cc3)n2)cc1] | 4807 ± 682 |
| RLX-10[a] | 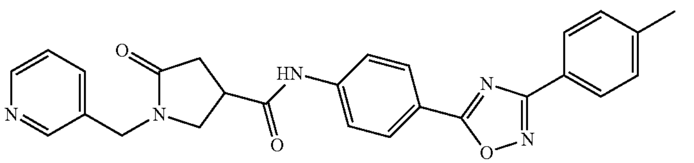 [SMILES: Cc1ccc(-c2noc(-c3ccc(NC(=O)C4CC(=O)N(Cc5cccnc5)C4)cc3)n2)cc1] | 2355 ± 248 |
| RLX-12 | 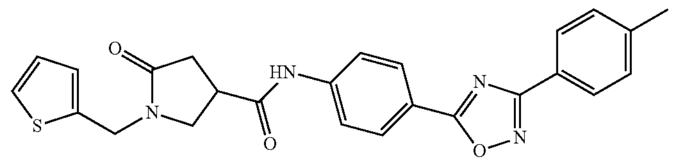 | 4761 ± 364 |
| RLX-13 | 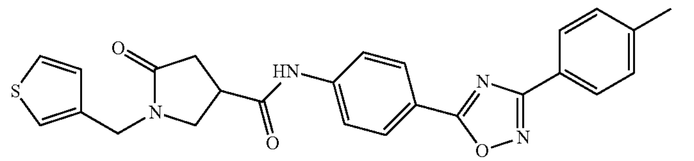 | 4802 ± 324 |
| RLX-14 | 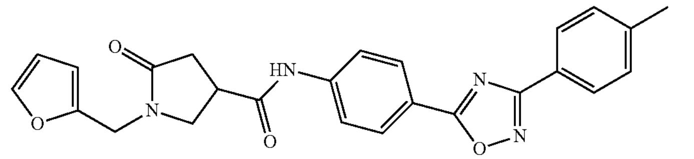 [SMILES: Cc1ccc(-c2noc(-c3ccc(NC(=O)C4CC(=O)N(Cc5cccs5)C4)cc3)n2)cc1] | 4497 ± 692 |

TABLE 1-continued
| Biological data for select RLX compounds. | | |
|---|---|---|
| Compound # | Structure | $IC_{50}$ (nM)[b] |
| RLX-15 | 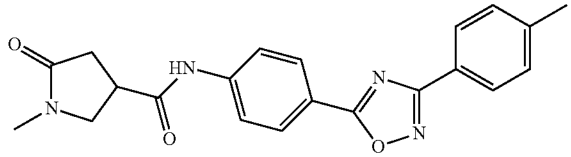 | 2718 ± 384 |
| RLX-16 | 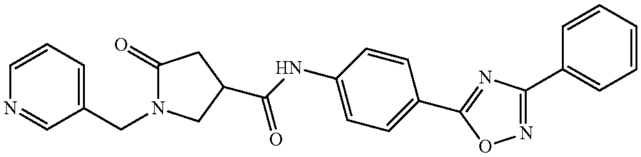 [SMILES: O=C(Nc1ccc(-c2nc(-c3ccccc3)no2)cc1)C1CC(=O)N(Cc2cccnc2)C1] | 6610 ± 909 |
| RLX-17 | 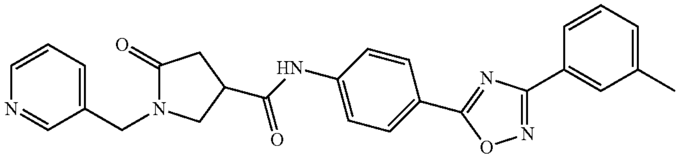 [SMILES: Cc1cccc(-c2noc(-c3ccc(NC(=O)C4CC(=O)N(Cc5cccnc5)C4)cc3)n2)c1] | 5351 ± 1338 |
| RLX-18 | 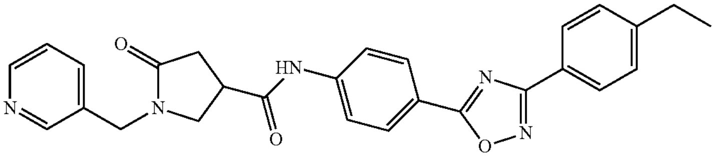 [SMILES: CCc1ccc(-c2noc(-c3ccc(NC(=O)C4CC(=O)N(Cc5cccnc5)C4)cc3)n2)cc1] | 5015 ± 669 |
| RLX-19[a] | 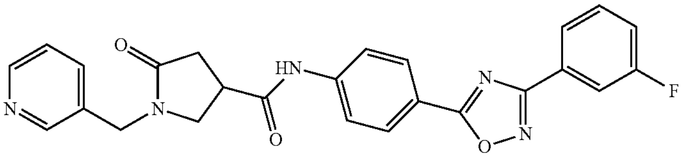 [SMILES: O=C(Nc1ccc(-c2nc(-c3cccc(F)c3)no2)cc1)C1CC(=O)N(Cc2cccnc2)C1] | 1344 ± 226 |
| RLX-20[a] | 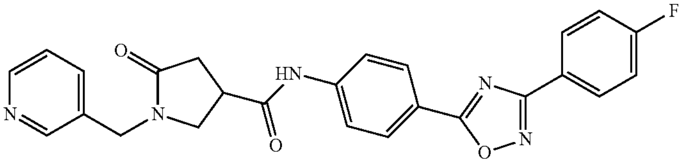 [SMILES: O=C(Nc1ccc(-c2nc(-c3ccc(F)cc3)no2)cc1)C1CC(=O)N(Cc2cccnc2)C1] | 1911 ± 367 |
| RLX-21 | 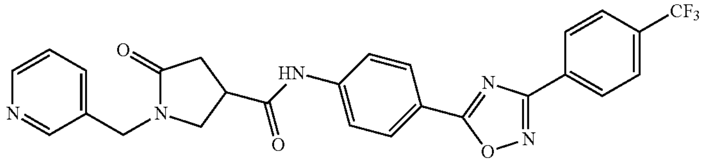 [SMILES: O=C(Nc1ccc(-c2nc(-c3ccc(C(F)(F)F)cc3)no2)cc1)C1CC(=O)N(Cc2cccnc2)C1] | 2501 ± 97 |
| RLX-22 | 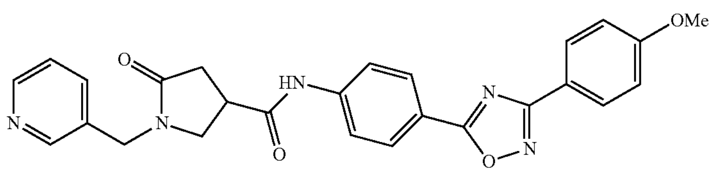 [SMILES: COc1ccc(-c2noc(-c3ccc(NC(=O)C4CC(=O)N(Cc5cccnc5)C4)cc3)n2)cc1] | Not active |
| RLX-24 | 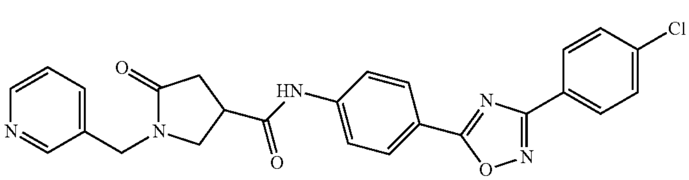 [SMILES: O=C(Nc1ccc(-c2nc(-c3ccc(Cl)cc3)no2)cc1)C1CC(=O)N(Cc2cccnc2)C1] | 1253 ± 219 |

TABLE 1-continued

| Biological data for select RLX compounds. | | |
|---|---|---|
| Compound # | Structure | $IC_{50}$ (nM)[b] |
| RLX-25 | 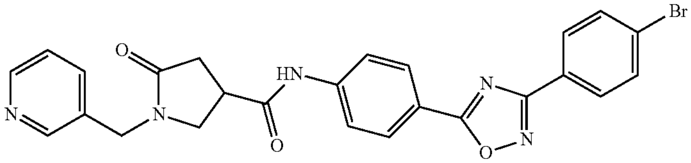 [SMILES: O=C(Nc1ccc(-c2nc(-c3ccc(Br)cc3)no2)cc1)C1CC(=O)N(Cc2cccnc2)C1] | 2893 ± 193 |
| RLX-32 | 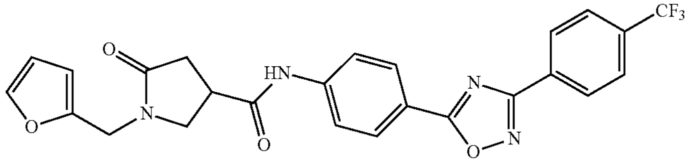 [SMILES: O=C(Nc1ccc(-c2nc(-c3ccc(C(F)(F)F)cc3)no2)cc1)C1CC(=O)N(Cc2ccco2)C1] | 6684 ± 349 |
| RLX-33 | 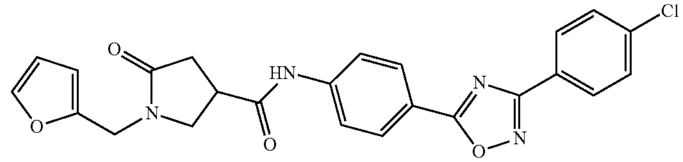 [SMILES: O=C(Nc1ccc(-c2nc(-c3ccc(Cl)cc3)no2)cc1)C1CC(=O)N(Cc2ccco2)C1] | 2880 ± 321 |
| RLX-37 | 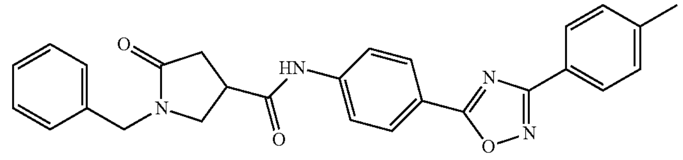 [SMILES: Cc1ccc(-c2noc(-c3ccc(NC(=O)C4CC(=O)N(Cc5ccccc5)C4)cc3)n2)cc1] | >10,000 |
| RLX-39 | 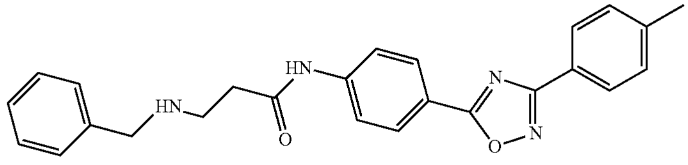 [SMILES: Cc1ccc(-c2noc(-c3ccc(NC(=O)CCNCc4ccccc4)cc3)n2)cc1] | 5595 ± 623 |

[a]The compound was tested as the HCl salt.
[b]$IC_{50}$ values are the mean ± SEM of at least three independent experiments in duplicate.

Figure 2:
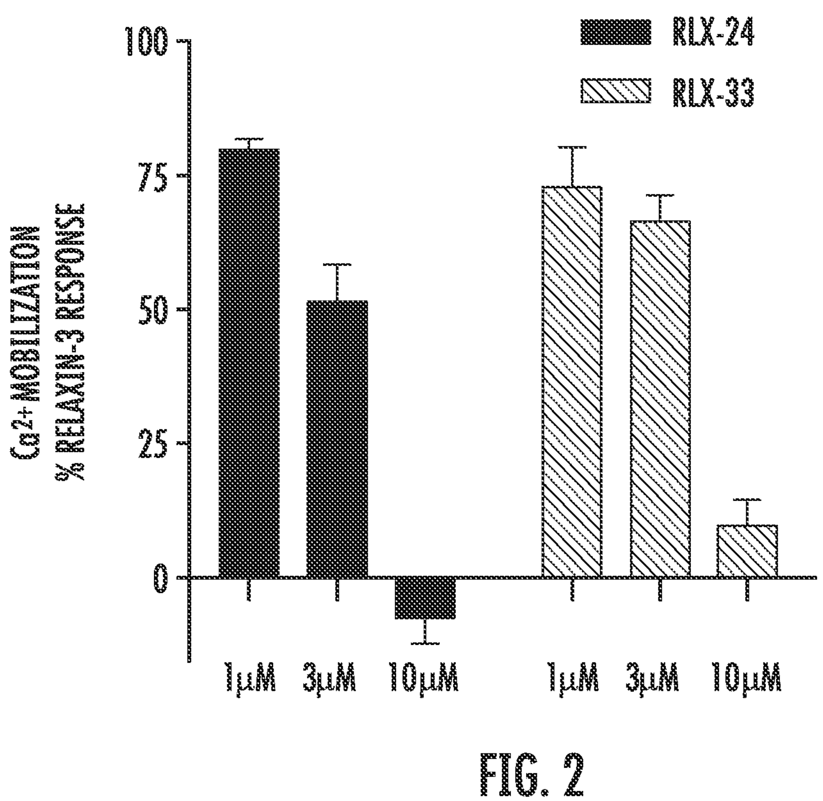
FIG. 2 displays the inhibition of relaxin-3 activity by representative compounds (RLX-24 and RLX-33) in the calcium mobilization assays.

Calcium mobiolization assay: The promiscuous $G\alpha_{q16}$ has been reported to be able to shift the signal transduction of RXFP3 from cAMP inhibition to calcium mobilization. See Liu et al., J. Biol. Chem. 2003, 278, 50765. Relaxin-3 potently stimulated calcium mobilization with an $EC_{50}$ value ~5 nM in the HEK293 cells that coexpressed RXFP3 and $G\alpha_{q16}$. To study the antagonist activity of RLX compounds, we have developed functional calcium mobilization assays using CHO cells simultaneously overexpressing human RXFP3 and $G\alpha_{q16}$. Briefly. CHO-$G\alpha_{q16}$ cells (RD-HGA16. Molecular Devices) were cultured in F12 media supplemented with 10% FBS, 100 units/mL penicillin, 100 μg/mL streptomycin, and 200 μg/mL hygromycin. CHO-$G\alpha_{q16}$ cells were transiently transfected with pcDNA 3.1(+) containing N-terminal HA-tagged human RXFP3 (Genscript) using Lipofectamine Plus reagent. After 24 hrs. cells were plated into 96-well black-walled assay plates at 30K cells/well in growth medium without selection antibiotics. Cells were incubated overnight at 37° C., 5% $CO_2$. The FLIPR Calcium 5 assay kit (Molecular Devices) was used according to the manufacturer's instructions with minor modifications. Briefly, reconstituted dye was diluted in pre-warmed assay buffer (HBSS, 20 mM HEPES, 2.5 mM probenecid, pH 7.4 at 37° C.). Growth medium was removed, and the cells were gently washed with assay buffer. Calcium 5 dye was added to the cells and the plate was incubated for 45 min at 37° C. 5% $CO_2$. Various concentrations of test antagonist were prepared at 10× the desired final concentration. Cells were pretreated with the test compound or vehicle in a final concentration of 0.25% BSA/1% DMSO for 15 min at 37° C. Assay plates were read with a FLIPR Tetra instrument (excitation at 485 nm, detection at 525 nm. Molecular Devices). Calcium-mediated changes in fluorescence were monitored over a 90 s time period. Relaxin-3 peptide (10 nM) was added during the read and the maximum response in relative fluorescent units (RFU) was measured. Data were normalized across experiments to the relaxin-3 peptide response at 10 nM. FIG. 2 displays the inhibition of relaxin-3 activity by representative compounds (RLX-24 and RLX-33) in the calcium mobilization assays.

Figure 3:
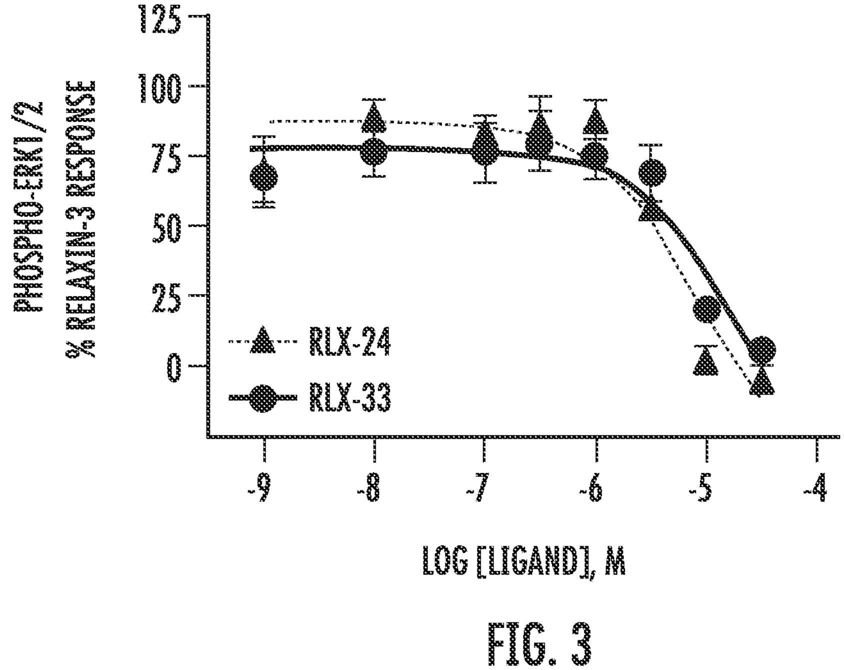
FIG. 3 displays the concentration-response curves of representative compounds (RLX-24 and RLX-33) for inhibition of relaxin-3 activity in RXFP3 ERK1/2 phosphorylation assays.

ERK1/2 phosphorylation assay: RXFP3 is known to stimulate extracellular signal-regulated kinase (ERK) 1/2 phosphorylation in a $G\alpha_{i/o}$-dependent manner. See van der Westhuizen et al., Mol. Pharmacol. 2007, 71, 1618. Here, we also investigated the antagonist activity of RLX compounds on ERK signaling pathway. In brief, CHO human RXFP3 cells (Perkin Elmer, ES-656-C) were plated at 30K cells/well in 96-well plate format. The next day growth media was removed and replaced with F-12 media without any supplements. Cells were serum starved for 4 hrs. Cells were then exposed to various concentrations of test compound or vehicle for 15 min with a final concentration of 1% DMSO/0.1% BSA. Next cells were exposed to relaxin-3 peptide (1 nM) for 5 min, followed by removal of the media and addition of lysis buffer. Cell lysates were then incubated with an Eu-labeled anti-phospho-ERK1/2 (T202-Y204) antibody and a ULight-labeled anti-ERK1/2 antibody according to the manufacturer's instructions (Perkin Elmer, Phosphorylated ERK1/2 (T202-Y204) LANCE Ultra Cellular Detection Kit). After 20 hrs., the TR-FRET signal (ex 337 nm) was read on a CLARIOstar multimode plate reader (BMG Biotech, Cary, North Carolina, United States of America). Fluorescence values at 665 nm were normalized to percent response of relaxin-3 peptide (1 nM) and compound concentration response curves were generated using nonlinear regression analysis (3-parameter) (GraphPad Prism, GraphPad Software, Inc., San Diego, California, United States of America). FIG. 3 displays the concentration-response curves of representative compounds (RLX-24 and RLX-33) for inhibition of relaxin-3 activity in RXFP3 ERK1/2 phosphorylation assays.

It will be understood that various details of the presently disclosed subject matter can be changed without departing from the scope of the presently disclosed subject matter. Furthermore, the foregoing description is for the purpose of illustration only, and not for the purpose of limitation.

What is claimed is:

1. A compound having inhibitory activity for the relaxin family peptide 3 receptor (RXFP3), optionally wherein the compound has a half maximal inhibitory concentration $IC_{50}$ for RXFP3 in the presence of relaxin-3 of about 10 micromolar (μM) or less, wherein the compound has a structure of Formula (I):

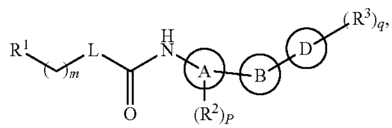

wherein:

L is

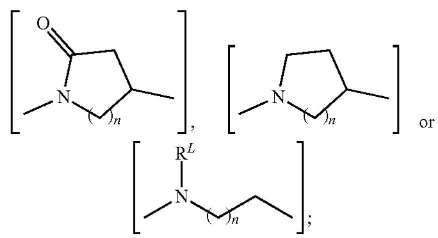

n is an integer between 1 and 3;

$R^L$ is selected from the group comprising hydrogen, C1-C6 substituted or unsubstituted alkyl, C2-C6 substituted or unsubstituted alkenyl, C3-C6 substituted or unsubstituted cycloalkyl, substituted or unsubstituted heterocyclo, substituted or unsubstituted aryl, and substituted or unsubstituted heteroaryl;

m is an integer between 0 and 3;

p is an integer between 0 and 3;

q is an integer between 0 and 3;

A is selected from phenyl and pyridinyl;

B is a five-membered heterocyclic group;

D is selected from substituted or unsubstituted aryl and substituted or unsubstituted heteroaryl;

$R^1$ is selected from the group consisting of hydrogen, C1-C6 substituted or unsubstituted alkyl, C2-C6 substituted or unsubstituted alkenyl, C3-C6 substituted or unsubstituted cycloalkyl, substituted or unsubstituted heterocyclo, substituted or unsubstituted aryl, and substituted or unsubstituted 5- or 6-membered heteroaryl;

each $R^2$ is independently selected from the group consisting of substituted or unsubstituted C1-C6 alkyl, substituted or unsubstituted C3-C6 alkenyl, C1-C6 substituted or unsubstituted cycloalkyl, C1-C6 alkoxy; substituted or unsubstituted heterocyclo, halo, nitro, cyano, amino, alkylsulfonyl, ester and amide; and each $R^3$ is independently selected from C1-C6 substituted or unsubstituted alkyl, C2-C6 substituted or unsubstituted alkenyl, C3-C6 substituted or unsubstituted cycloalkyl, C1-C6 alkoxy, substituted or unsubstituted heterocyclo, halo, nitro, cyano, amino, alkylsulfonyl, ester, and amide; or a pharmaceutically acceptable salt thereof.

2. The compound of claim 1, wherein B is 1,2,4-oxadiazole.

3. The compound of claim 1, wherein m is 1, 2, or 3; and wherein $R^1$ is selected from a substituted or unsubstituted phenyl, a substituted or unsubstituted five-membered heteroaryl, and a substituted or unsubstituted six-membered heteroaryl.

4. The compound of claim 3, wherein $R^1$ is phenyl, a five-membered heteroaryl, or a six-membered heteroaryl, and wherein said phenyl, five-membered heteroaryl, or six-membered heteroaryl is substituted with one or more of the group consisting of C1-C6 alkyl, C2-C6 alkenyl, C1-C6 alkoxy, C3-C6 cycloalkyl, heterocyclo, halo, nitro, cyano, amino, alkylsulfonyl, ester, and amide.

5. The compound of claim 1, wherein n is 2.

6. The compound of claim 5, wherein the compound is:

RLX-34

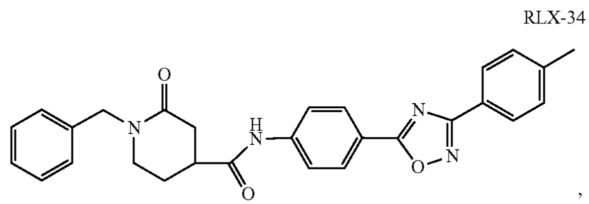 [SMILES: Cc1ccc(-c2noc(-c3ccc(NC(=O)C4CCN(Cc5ccccc5)C(=O)C4)cc3)n2)cc1]

or a pharmaceutically acceptable salt thereof.

7. The compound of claim 1, wherein n is 1.

8. The compound of claim 7, wherein the compound is:

RLX-36

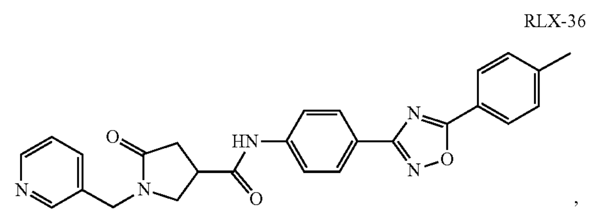 [SMILES: Cc1ccc(-c2nc(-c3ccc(NC(=O)C4CC(=O)N(Cc5cccnc5)C4)cc3)no2)cc1]

or a pharmaceutically acceptable salt thereof.

9. The compound of claim 7, wherein the compound has a structure of Formula (II):

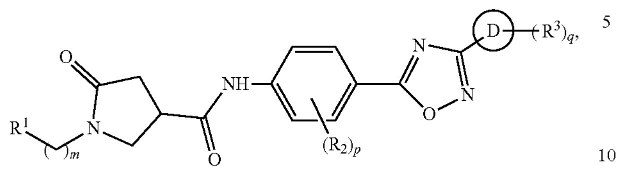

wherein:

m is an integer between 0 and 3;

p is an integer between 0 and 3;

q is an integer between 0 and 3;

D is selected from substituted or unsubstituted aryl and substituted or unsubstituted heteroaryl;

$R^1$ is selected from the group consisting of hydrogen, C1-C6 substituted or unsubstituted alkyl, C2-C6 substituted or unsubstituted alkenyl, C3-C6 substituted or unsubstituted cycloalkyl, substituted or unsubstituted heterocyclo, substituted or unsubstituted aryl, and substituted or unsubstituted heteroaryl;

each $R^2$ is independently selected from the group consisting of substituted or unsubstituted C1-C6 alkyl, substituted or unsubstituted C3-C6 alkenyl, C3-C6 substituted or unsubstituted cycloalkyl, C1-C6 alkoxy; substituted or unsubstituted heterocyclo, halo, nitro, cyano, amino, alkylsulfonyl, ester and amide; and each $R^3$ is independently selected from C1-C6 substituted or unsubstituted alkyl, C2-C6 substituted or unsubstituted alkenyl, C3-C6 substituted or unsubstituted cycloalkyl, C1-C6 alkoxy, substituted or unsubstituted heterocyclo, halo, nitro, cyano, amino, alkylsulfonyl, ester, and amide; or a pharmaceutically acceptable salt thereof.

10. The compound of claim 9, wherein D is selected from the group consisting of phenyl and pyridinyl.

11. The compound of claim 10, wherein $R^1$ is selected from the group consisting of methyl, phenyl, substituted phenyl, pyridinyl, thiophenyl, and furanyl.

12. The compound of claim 9, wherein the compound is selected from:

RLX-28

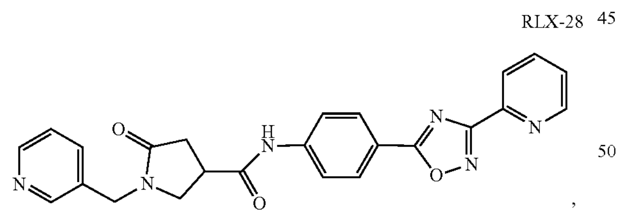

,

-continued

RLX-29

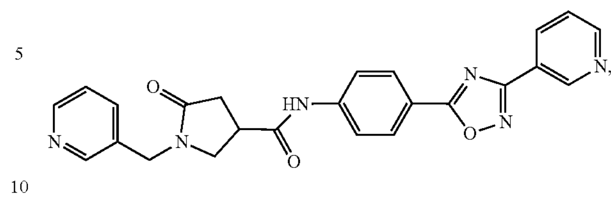

RLX-30

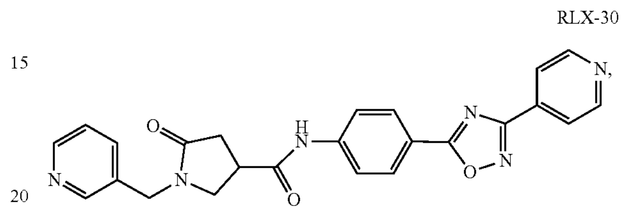

and pharmaceutically acceptable salts thereof.

13. A pharmaceutical composition comprising a compound of claim 1 and a pharmaceutically acceptable carrier.

14. A method of treating a disease or condition associated with aberrant expression and/or activity of relaxin-3 or associated with aberrant expression and/or activity of the RXFP3 receptor in a subject in need thereof, the method comprising administering to said subject an effective amount of a compound of claim 2 or of a pharmaceutical composition of claim 13.

15. The method of claim 14, wherein the disease or condition is selected from obesity, antipsychotic drug-induced weight gain, hyperphagia associated with depression, alcoholism, and other substance abuse and/or addiction-related disorders.

16. A method for the prevention or inhibition of substance abuse and/or addiction, addictive behavior, or of a symptom, behavior, or condition associated with substance abuse and/or addiction, wherein the behavior associated with substance abuse and/or addiction comprises substance use (self-administration) and/or substance seeking behavior;

the method comprising administering to a subject in need thereof an effective amount of a compound of claim 1 or a pharmaceutical composition of claim 13.

* * * * *